(12) United States Patent
McTigue et al.

(10) Patent No.: US 6,794,146 B2
(45) Date of Patent: Sep. 21, 2004

(54) MODIFICATIONS OF THE VEGF RECEPTOR-2 PROTEIN AND METHODS OF USE

(75) Inventors: Michele A. McTigue, Encinitas, CA (US); Chris Pinko, San Diego, CA (US); Camran V. Parast, San Diego, CA (US); Michael R. Gehring, Ramona, CA (US); Chen-Chen Kan, Del Mare, CA (US); Krzysztof Appelt, Poway, CA (US); John A. Wickersham, Escondido, CA (US); Richard E. Showalter, Lakeside, CA (US); Anna M. Tempcyzk-Russell, San Diego, CA (US); Barbara Mroczkowski, Encinitas, CA (US); Jesus E. Villafranca, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 325 days.

(21) Appl. No.: 09/939,832

(22) Filed: Aug. 28, 2001

(65) Prior Publication Data

US 2002/0127538 A1 Sep. 12, 2002

Related U.S. Application Data

(62) Division of application No. 09/390,326, filed on Sep. 7, 1999, now Pat. No. 6,316,603.
(60) Provisional application No. 60/099,503, filed on Sep. 8, 1998.

(51) Int. Cl.[7] .................. G01N 33/53; A61K 38/00; C07K 1/00; C07K 14/00; C07H 21/02

(52) U.S. Cl. .................. 435/7.1; 530/300; 530/350; 530/402; 536/23.1

(58) Field of Search .................. 435/7.1, 6, 320.1, 435/252.3, 183, 70.1; 530/300, 350, 402; 536/23.1

(56) References Cited

U.S. PATENT DOCUMENTS

| | | | |
|---|---|---|---|
| 4,966,849 A | 10/1990 | Valee et al. | |
| 5,217,999 A | 6/1993 | Levitzki et al. | |
| 5,302,606 A | 4/1994 | Spada et al. | |
| 5,330,992 A | 7/1994 | Eissenstat et al. | |
| 6,043,211 A | * 3/2000 | Williams et al. | 514/2 |

FOREIGN PATENT DOCUMENTS

| | | |
|---|---|---|
| WO | WO91/15495 | 10/1991 |
| WO | Wo92/20642 | 11/1992 |
| WO | WO92/21660 | 12/1992 |
| WO | WO94/03427 | 2/1994 |
| WO | WO94/10202 | 5/1994 |
| WO | WO 98/49300 | 11/1998 |

OTHER PUBLICATIONS

Adamis et al., *Arch. Ophthalmol.*, 114:66–71 (1996).
Agouron Pharmaceuticals, Inc. "Agouron Solves Structure of Key Target for Drugs to Block Angiogenesis: Human VEGF Receptor 2 Kinase", Mar. 4, 1999.
Bazenet et al., *Mol. Cell. Biol.*, 16:6926–6936 (1996).
Borgström et al, *Cancer Res.*, 56:4032–4039 (1996).
Bourne, H.R., et al., *Basic & Clinical Pharmacology*, 3rd Edition (Katzung et al., eds), Chapter 3, pp. 9–22 (1987).
Choudhury et al., *FEBS Letters*, 282(2):351–354 (May, 1991).
Dvorak et al., *Am. J. Path.*, 146:1029–1039 (1995).
DeVries et al., *Science*, 255:989–991 (1992).
Dougher–Vermazen et al., *Biochem. Biophys. Res. Comm.*, 205:728–738 (1994).
Ferrara & Henzel, *Biochem. Biophys. Res. Comm*, 161:851–858 (1989)—Abstract only.
Ferrara N. and Davis–Smyth, *Endocrine Rev.*, 18:4–25 (1997).
Folkham, *J. Natl., Cancer Inst.*, 82:4–6 (1991).
Folkman et al., *J. Biol. Chem.*, 267:10931–10934 (1992).
Heidaran et al., *Mol. Cell. Biol.*, 11:134–142 (1991).
Hori et al., *Cancer Res.*, 51:6180–9184 (1991).
Houck, et al., *J. Biol. Chem.*, 267:26031–26037 (1992).
Hubbard, *EMBO J.*, 16:5572–5581 (FGFR1) (1997).
Hubbard, et al., *Nature*, 372:746–754 (1994).
Jellinek, et al., *Biochemistry*, 3:10450–56 (1994).
Johnson et al., *Cell*, 85:149–158 (1996).
Kazlauskas et al., *Mol. Cell. Biol.*, 12:2534–2544 (1992).
Kim et al., *Nature*, 362:841–843 (1993).
Kinsella, et al., *Exp. Cell Res.*, 199:56–62 (1992).
Klagsburn & Soker, *Current Biology*, 3:699–702 (1993).
Knighton et al., *Science*, 253:407–413 (1991).
Kumar and Fidler *In Vivo*, 18:27–34 (1998)—Abstract only.
Lev et al., *Proc. Natl. Acad. Sci. USA*, 89:678–682 (1992).
Matsui,T., et al., *Science*, 243:800–804 (1989).
McLeskey et al., *Cancer Res.*, 53:2168–2177 (1993).

(List continued on next page.)

Primary Examiner—Kenneth R. Horlick
Assistant Examiner—Young J. Kim
(74) Attorney, Agent, or Firm—Stephen D. Prodnuk; Bryan C. Zielinski; Peter Richardson

(57) ABSTRACT

A 2.4 Å crystal structure of a protein construct containing the catalytic kinase domain of vascular endothelial growth factor receptor 2 (VEGFR2/KDR), a key enzyme in angiogenesis, has been determined in an unliganded, phosphorylated state. This protein construct, contains a modified catalytic linker and has comparable in vitro kinase activity to constructs containing the entire KID. The resulting construct retains comparable in vitro kinase activity to that of the wild-type KID, and more importantly, allows complete crystallization of the protein such that it may be characterized by X-ray crystallography. The present invention further discloses the use of ray crystallographic data for identification and construction of possible therapeutic compounds in the treatment of various disease conditions.

2 Claims, 67 Drawing Sheets

OTHER PUBLICATIONS

McRee et al., *J. Struct. Biol.,* 125 (2–3):156–165 (1999)—Abstract only.
Mohammadi et al., *Cell,* 86:577–87 (1996).
Mohammadi et al., *Science,* 276:955–960 (1997).
Mullis, et al., *Biotechnology,* 24:17–27 (1992)—Abstract Only.
Parast et al., Biochemistry, 37(47):16788–16801 (Nov. 5, 1998).
Pepper, M.S., *Vasc. Med.,* 1:259–266 (1996)—Abstract Only.
Reedjik, et al., *EMBO J.,* 11:1365–1372 (1992).
Risau, W., *FASEB J.,* 9:926–933 (1995).
Schuchter, et al., *Cancer Res.,* 51:682–687 (1991).
Seetharm, et al., *Oncogene,* 10:135–147 (1995).
Severinsson et al., *Mol. Cell. Biol.,* 10:801–809 (1990).
Shalaby et al., *Nature,* 376:576–579 (1995).
Shibuya, et al., *Oncogene,* 5:519–524 (1990).
Szekanecz, et al., *J. Investig. Med.,* 46:27–41 (1998).
Takano, et al., *Mol. Bio. Cell,* 4:358A, (1993).
Taylor, et al., *EMBO Journal,* 8(7):2029–2037 (1989).
Terman et al., *Biochem Biophys. Res. Commun.,* 187:1579–8 (1992).
Thomas, K., *J. Biol Chem,* 271(2):603–606 (1996)—Abstract only.
Thomas & Kendall, *Proc. Natl. Acad. Sci.,* 90:10705–09, (1994).
Tolentino and Adamis, *Int. Ophthalmol. Clin.* 38:77–94, (1988).
Vaisman et al., *J. Biol. Chem.,* 265:19461–19566, (1990).
van der Geer et al., *Ann. Rev. Cell Biol,* 10:251–337, (1994)—Abstract only.
Waltenberger et al., *J. Biol. Chem.,* 269:26988–26995, (1994).
Wei et al., *J. Biol. Chem.,* 270:8122–8130, (1995).
Weidner, et al., *New Engl. J. Med.,* 324:1–5, (1991).
Yamaguchi and Hendrickson, *Nature,* 384:484–489 (1996).
Yu et al., *Mol. Cell. Biol.,* 11:3780–3785 (1991).
McTigue, et al. "Crystal Structure of the Kinase Domain of Human Vascular Endothelial Growth Factor Receptor 2: A Key Enzyme in Angiogenesis," Structure 1999; 7:319–330.
Al–Obeidi, et al., "Protein Tyrosine Kinases: Structure, Substrate Specificity, and Drug Discovery," Biopolymers (Peptide Science), vol. 47, 197–223 (1998).
Wei, et al., "Expression, Characterization, and Crystallization of the Catalytic Core of the Human Insulin Receptor Protein–tyrosine Kinase Domain," J. Biol. Chem. 1995; 270(14): 8122–8130.
Hubbard, et al., "Crystal Structure of the Tyrosine Kinase Domain of the Human Insulin Receptor," Nature 1994; 372:746–759.
SCOPES, "Protein Purification: Principles and Practice," Second Ed., 1987, pp. 297–301.
Mohammadi, et al., "Structure of the Tyrosine Kinase Domain of Fibroblast Growth Receptor in Complex with Inhibitors," Science 997; 276: 955–960.
McDonald, et al., "The First Structure of a Receptor Tyrosine Kinase Domain: A Further Step in Understanding the Molecular Basis of Insulin Action," Structure 1995; 3:1–6.
Singh, et al., Structure–Based Design of a Potent, Selective, and Irreversible Inhibitor of the Catalytic Domain of the erbB Receptor Subfamily of Protein Tyrosine Kinases, J. Med. Chem. 1997; 40: 1130–1135.

* cited by examiner

FIG. 1a

```
                                        ┌─ nucleotide-binding
                                        │       loop
                                           αB            β1            β2
                                        ─────────       ────          ────
VEGF-R2   806  MDPDELPLDEHCERLPYDASKWEFPRDRLKLGKPLGRGAFGQVEADAFGIDKTATCR--    863
FGFR1     456  ---MLAGVSEY--ELP-EDPRWELPRDRLVLGKPLGEGCFGQVLAEAIGLDKDKPNRVT    509
IRK       978  ------VFPCSVYVPDEWEVSREKITLLRELGQGSFGMVEGNARDIIKGEAE--T       1025
VEGF-R1   799  MDPDEVPLDEQCERLPYDASKWEFARERLKLGKSLGRGAFGKVQASAFGIKKSPTCR--   856
PDGFRα    576  ------DPMQLPYD-SRWEFPRDGLVLGRVLGSGAFGKVEGTAYGLSRSQPVM-        622

αC
                       β3                     ──────────────────────
VEGF-R2   864  TVAVKMLKEGATHSEHRALMSELKILIHIGHHLNVVNLLGACTKPGGPLMVIVEFCKFGN  923
FGFR1     510  KVAVKMLKSDATEKDLSDLISEMEMMKMIGKHKNIINLLGACT-QDGPLYVIVEYASKGN  568
IRK      1026  RVAVKTVNESASLRERIEFLNEASVMKGFTCH-HVVRLLGVVSK-GQPTLVVMELMAHGD 1083
VEGF-R1   857  TVAVKMLKEGATASEYKALMTELKILTHIGHHLNVVNLLGACTKQGGPLMVIVEYCKYGN  916
PDGFRα    623  KVAVKMLKPTARSSEKQALMSELKIMTHLGPHLNIVNLLGACTK-SGPIYIITEYCFYGD  681

αD                  ┌─── kinase insert domain
                ──────────────────
VEGF-R2   924  LSTYLRSKRNEFVPYKTKGARFRQGKDYVG------------------------------  953
FGFR1     569  LREYLQARRPPGLEYCYN----------------------------------------    586
IRK      1084  LKSYLRSLRPEA----------------------------------------------   1095
VEGF-R1   917  LSNYLKSKRDLFFLNKDAALHMEPKKEKME----------------------------    946
PDGFRα    682  LVNYLHKNRDSFLSHHPEKPKKELDIFGLNPADESTRSYVILSFENNGDYMDMKQADTTQ  741

αE
                                                                ─────────
VEGF-R2   954  ---AIPVDLKRRLDSITSSQSSASSGFVEEKSLSDVEEEEAPEDLYKDFLTLEHLICYSF 1010
FGFR1     587  ---------------------------------------PSHNPEEQLSSKDLVSCAY    605
IRK      1096  --------------------------------------ENNPGRPPPTLQEMIQMAA    1114
VEGF-R1   947  --PGLEQGKKPRLDSVTSSESFASSGFQEDKSLSDVEEEDSDGFYKEPITMEDLISYSF  1004
PDGFRα    742  YVPMLERKEVSKYSDIQRSLYDRPASYKK-KSMLDSEVKNLLSDDNSEGLTLLDLLSFTY  800
```

FIG. 1b

```
                    catalytic loop   β7              β8                    activation loop
VEGF-R2  1011  QVAKGMEFDLASRKCIHRDLAARNILLSEKNVVKICDFGLARDIYKDPDYVRKGDARLPLK  1070
FGFR1     606  QVARGMEYSLASKKCIHRDLAARNVLVTEDNVMKIADFGLARDIHHIDYYKKTTNGRLPVK   665
IRK      1115  EIADGMEY-LNAKKFVHRDLAARNCMVAHDFTVKIGDFGMTRDIYETDYYRKGGKGLLPVR  1174
VEGF-R1  1005  QVARGMEFDLSSRKCIHRDLAARNILLSENNVVKIDDFGLARDIYKNPDYVRKGDTRLPLK  1064
PDGFRα    801  QVARGMEF-LASKKCIHRDLAARNVLLAQGKIVKIDDFGLARDIMHDSNYVSKGSTFLPVK   860

αEF            αF
VEGF-R2  1071  WMAPETIFDRVYTIQSDVWSFGVLLWEIFSLGASPYPGVKIDEEFCRRLKEGTRMRRAPDY  1130
FGFR1     666  WMAPEALFDRIYTHQSDVWSFGVLLWEIFTLGGSPYPGVPVEELFKLLKEGHRMDRKPSN   923
IRK      1175  WMAPESLKDGVFTTSSDMWSFGVV WEITSLAEQPYQGLSNEQVL-KFVMDGGYLDLQPDN  1083
VEGF-R1  1065  WMAPESIFDKIYSTKSDVWSYGVLLWEIFSLGGSPYPGVQMDEDFCSRLREGMRMRRAPEY   916
PDGFRα    861  WMAPESIFDNLYTTLSDVWSYGILLWEIFSLGGTPYPGMMVDSTFYNKIKSGYRMAFKPDH   681

αH                                  αI
VEGF-R2  1131  TTPEMYQTMLDCWHGEPSQRPTFSELVEHLGNLLQANAQQD                      1171
FGFR1     725  CTNELYMMMRDCWHAVPSQRPTFKQLVEDLDRIVALTSNQE                       765
IRK      1234  CPERVTDLMRMCWQFNPNMRPTFLEIVNLLKDDLHPSFPEV                      1274
VEGF-R1  1125  STPEIYQIMLDCWHRDPKERPRFAELVEKLGDLLQANVQQD                      1165
PDGFRα    921  ATSEVYEIMVKCWNSEPEKRPSFYHLSEIVENLLPGQYKKS                       961
```

VEGFR2D50P

FGFR1

IRKP

FIG. 7(1)

| | | | | | | | | |
|---|---|---|---|---|---|---|---|---|
| ATOM | 1 | CB | LEU | 820 | 49.908 | 45.905 | 17.938 | 1.00 48.95 |
| ATOM | 2 | CG | LEU | 820 | 50.568 | 45.069 | 16.833 | 1.00 43.57 |
| ATOM | 3 | CD1 | LEU | 820 | 50.004 | 45.358 | 15.456 | 1.00 43.59 |
| ATOM | 4 | CD2 | LEU | 820 | 52.066 | 45.345 | 16.886 | 1.00 47.45 |
| ATOM | 5 | C | LEU | 820 | 49.216 | 48.321 | 17.530 | 1.00 48.14 |
| ATOM | 6 | O | LEU | 820 | 48.196 | 48.587 | 18.187 | 1.00 52.58 |
| ATOM | 9 | N | LEU | 820 | 50.481 | 47.725 | 19.581 | 1.00 53.68 |
| ATOM | 11 | CA | LEU | 820 | 50.302 | 47.387 | 18.117 | 1.00 50.63 |
| ATOM | 12 | N | PRO | 821 | 49.435 | 48.842 | 16.306 | 1.00 41.32 |
| ATOM | 13 | CD | PRO | 821 | 50.680 | 48.870 | 15.520 | 1.00 45.54 |
| ATOM | 14 | CA | PRO | 821 | 48.465 | 49.733 | 15.700 | 1.00 31.06 |
| ATOM | 15 | CB | PRO | 821 | 49.067 | 49.985 | 14.352 | 1.00 28.89 |
| ATOM | 16 | CG | PRO | 821 | 50.509 | 50.148 | 14.734 | 1.00 43.44 |
| ATOM | 17 | C | PRO | 821 | 47.123 | 49.165 | 15.569 | 1.00 26.14 |
| ATOM | 18 | O | PRO | 821 | 46.948 | 47.970 | 15.374 | 1.00 26.03 |
| ATOM | 19 | N | TYR | 822 | 46.154 | 50.024 | 15.776 | 1.00 16.25 |
| ATOM | 21 | CA | TYR | 822 | 44.799 | 49.643 | 15.582 | 1.00 18.88 |
| ATOM | 22 | CB | TYR | 822 | 44.061 | 49.519 | 16.916 | 1.00 17.42 |
| ATOM | 23 | CG | TYR | 822 | 42.584 | 49.316 | 16.728 | 1.00 18.46 |
| ATOM | 24 | CD1 | TYR | 822 | 41.674 | 50.341 | 17.047 | 1.00 21.12 |
| ATOM | 25 | CE1 | TYR | 822 | 40.314 | 50.206 | 16.812 | 1.00 13.80 |
| ATOM | 26 | CD2 | TYR | 822 | 42.086 | 48.144 | 16.175 | 1.00 12.24 |
| ATOM | 27 | CE2 | TYR | 822 | 40.714 | 47.997 | 15.951 | 1.00 13.44 |
| ATOM | 28 | CZ | TYR | 822 | 39.838 | 49.028 | 16.268 | 1.00 14.38 |
| ATOM | 29 | OH | TYR | 822 | 38.480 | 48.887 | 16.073 | 1.00 19.73 |
| ATOM | 31 | C | TYR | 822 | 44.253 | 50.760 | 14.705 | 1.00 16.93 |
| ATOM | 32 | O | TYR | 822 | 44.172 | 51.904 | 15.112 | 1.00 20.70 |
| ATOM | 33 | N | ASP | 823 | 44.054 | 50.456 | 13.439 | 1.00 15.20 |
| ATOM | 35 | CA | ASP | 823 | 43.509 | 51.418 | 12.506 | 1.00 13.55 |
| ATOM | 36 | CB | ASP | 823 | 43.856 | 50.945 | 11.091 | 1.00 11.37 |
| ATOM | 37 | CG | ASP | 823 | 43.456 | 51.933 | 10.016 | 1.00 16.45 |
| ATOM | 38 | OD1 | ASP | 823 | 42.546 | 52.754 | 10.258 | 1.00 21.86 |
| ATOM | 39 | OD2 | ASP | 823 | 44.022 | 51.854 | 8.904 | 1.00 12.33 |
| ATOM | 40 | C | ASP | 823 | 41.983 | 51.489 | 12.738 | 1.00 14.14 |
| ATOM | 41 | O | ASP | 823 | 41.224 | 50.722 | 12.172 | 1.00 19.73 |
| ATOM | 42 | N | ALA | 824 | 41.539 | 52.415 | 13.572 | 1.00 11.88 |
| ATOM | 44 | CA | ALA | 824 | 40.126 | 52.554 | 13.876 | 1.00 14.80 |
| ATOM | 45 | CB | ALA | 824 | 39.928 | 53.610 | 14.973 | 1.00 12.02 |
| ATOM | 46 | C | ALA | 824 | 39.259 | 52.893 | 12.658 | 1.00 19.09 |
| ATOM | 47 | O | ALA | 824 | 38.062 | 52.610 | 12.641 | 1.00 23.54 |

FIG. 7(2)

| | | | | | | | | |
|---|---|---|---|---|---|---|---|---|
| ATOM | 48 | N | SER | 825 | 39.857 | 53.496 | 11.635 | 1.00 18.25 |
| ATOM | 50 | CA | SER | 825 | 39.118 | 53.867 | 10.450 | 1.00 12.65 |
| ATOM | 51 | CB | SER | 825 | 40.023 | 54.678 | 9.543 | 1.00 11.88 |
| ATOM | 52 | OG | SER | 825 | 39.315 | 55.003 | 8.370 | 1.00 20.94 |
| ATOM | 54 | C | SER | 825 | 38.669 | 52.594 | 9.746 | 1.00 12.30 |
| ATOM | 55 | O | SER | 825 | 37.543 | 52.461 | 9.317 | 1.00 14.94 |
| ATOM | 56 | N | LYS | 826 | 39.557 | 51.633 | 9.642 | 1.00 14.98 |
| ATOM | 58 | CA | LYS | 826 | 39.188 | 50.396 | 8.988 | 1.00 22.45 |
| ATOM | 59 | CB | LYS | 826 | 40.445 | 49.660 | 8.483 | 1.00 16.46 |
| ATOM | 60 | CG | LYS | 826 | 40.091 | 48.370 | 7.820 | 1.00 23.00 |
| ATOM | 61 | CD | LYS | 826 | 40.962 | 48.071 | 6.657 | 1.00 26.19 |
| ATOM | 62 | CE | LYS | 826 | 42.391 | 48.041 | 7.092 | 1.00 35.70 |
| ATOM | 63 | NZ | LYS | 826 | 43.272 | 48.003 | 5.891 | 1.00 40.17 |
| ATOM | 67 | C | LYS | 826 | 38.324 | 49.437 | 9.839 | 1.00 21.47 |
| ATOM | 68 | O | LYS | 826 | 37.363 | 48.850 | 9.336 | 1.00 22.56 |
| ATOM | 69 | N | TRP | 827 | 38.589 | 49.376 | 11.144 | 1.00 20.96 |
| ATOM | 71 | CA | TRP | 827 | 37.917 | 48.406 | 11.996 | 1.00 16.87 |
| ATOM | 72 | CB | TRP | 827 | 38.974 | 47.620 | 12.785 | 1.00 18.53 |
| ATOM | 73 | CG | TRP | 827 | 39.942 | 46.898 | 11.910 | 1.00 12.95 |
| ATOM | 74 | CD2 | TRP | 827 | 39.643 | 45.810 | 11.029 | 1.00 9.73 |
| ATOM | 75 | CE2 | TRP | 827 | 40.795 | 45.562 | 10.274 | 1.00 9.36 |
| ATOM | 76 | CE3 | TRP | 827 | 38.505 | 45.038 | 10.801 | 1.00 11.54 |
| ATOM | 77 | CD1 | TRP | 827 | 41.233 | 47.231 | 11.684 | 1.00 12.87 |
| ATOM | 78 | NE1 | TRP | 827 | 41.753 | 46.440 | 10.689 | 1.00 10.49 |
| ATOM | 80 | CZ2 | TRP | 827 | 40.848 | 44.565 | 9.299 | 1.00 12.36 |
| ATOM | 81 | CZ3 | TRP | 827 | 38.556 | 44.053 | 9.826 | 1.00 10.55 |
| ATOM | 82 | CH2 | TRP | 827 | 39.718 | 43.830 | 9.087 | 1.00 11.88 |
| ATOM | 83 | C | TRP | 827 | 36.830 | 48.795 | 12.953 | 1.00 17.75 |
| ATOM | 84 | O | TRP | 827 | 35.985 | 47.951 | 13.271 | 1.00 15.08 |
| ATOM | 85 | N | GLU | 828 | 36.855 | 50.043 | 13.416 | 1.00 16.92 |
| ATOM | 87 | CA | GLU | 828 | 35.908 | 50.518 | 14.413 | 1.00 19.52 |
| ATOM | 88 | CB | GLU | 828 | 36.289 | 51.920 | 14.885 | 1.00 17.10 |
| ATOM | 89 | CG | GLU | 828 | 35.581 | 52.363 | 16.148 | 1.00 12.70 |
| ATOM | 90 | CD | GLU | 828 | 36.106 | 51.707 | 17.400 | 1.00 21.57 |
| ATOM | 91 | OE1 | GLU | 828 | 37.219 | 51.118 | 17.386 | 1.00 21.15 |
| ATOM | 92 | OE2 | GLU | 828 | 35.402 | 51.819 | 18.426 | 1.00 22.43 |
| ATOM | 93 | C | GLU | 828 | 34.494 | 50.510 | 13.910 | 1.00 20.94 |
| ATOM | 94 | O | GLU | 828 | 34.245 | 51.024 | 12.818 | 1.00 26.92 |
| ATOM | 95 | N | PHE | 829 | 33.569 | 49.990 | 14.734 | 1.00 21.12 |
| ATOM | 97 | CA | PHE | 829 | 32.138 | 49.880 | 14.391 | 1.00 17.93 |
| ATOM | 98 | CB | PHE | 829 | 31.791 | 48.400 | 14.160 | 1.00 16.42 |
| ATOM | 99 | CG | PHE | 829 | 30.384 | 48.164 | 13.669 | 1.00 20.17 |

FIG. 7(3)

| | | | | | | | | |
|---|---|---|---|---|---|---|---|---|
| ATOM | 100 | CD1 | PHE | 829 | 30.020 | 48.484 | 12.363 | 1.00 21.31 |
| ATOM | 101 | CD2 | PHE | 829 | 29.415 | 47.612 | 14.516 | 1.00 23.04 |
| ATOM | 102 | CE1 | PHE | 829 | 28.712 | 48.254 | 11.921 | 1.00 18.76 |
| ATOM | 103 | CE2 | PHE | 829 | 28.093 | 47.375 | 14.071 | 1.00 15.20 |
| ATOM | 104 | CZ | PHE | 829 | 27.750 | 47.692 | 12.792 | 1.00 17.17 |
| ATOM | 105 | C | PHE | 829 | 31.310 | 50.495 | 15.533 | 1.00 14.65 |
| ATOM | 106 | O | PHE | 829 | 31.574 | 50.211 | 16.686 | 1.00 16.15 |
| ATOM | 107 | N | PRO | 830 | 30.270 | 51.298 | 15.224 | 1.00 13.29 |
| ATOM | 108 | CD | PRO | 830 | 29.707 | 51.633 | 13.901 | 1.00 11.63 |
| ATOM | 109 | CA | PRO | 830 | 29.481 | 51.918 | 16.292 | 1.00 14.76 |
| ATOM | 110 | CB | PRO | 830 | 28.636 | 52.948 | 15.565 | 1.00 13.82 |
| ATOM | 111 | CG | PRO | 830 | 28.414 | 52.364 | 14.252 | 1.00 14.42 |
| ATOM | 112 | C | PRO | 830 | 28.629 | 51.005 | 17.098 | 1.00 19.79 |
| ATOM | 113 | O | PRO | 830 | 27.750 | 50.339 | 16.562 | 1.00 26.60 |
| ATOM | 114 | N | ARG | 831 | 28.830 | 51.060 | 18.410 | 1.00 18.39 |
| ATOM | 116 | CA | ARG | 831 | 28.085 | 50.246 | 19.335 | 1.00 14.56 |
| ATOM | 117 | CB | ARG | 831 | 28.469 | 50.580 | 20.743 | 1.00 11.53 |
| ATOM | 118 | CG | ARG | 831 | 29.808 | 50.050 | 21.092 | 1.00 12.65 |
| ATOM | 119 | CD | ARG | 831 | 30.117 | 50.265 | 22.554 | 1.00 12.46 |
| ATOM | 120 | NE | ARG | 831 | 31.261 | 51.148 | 22.584 | 1.00 20.55 |
| ATOM | 122 | CZ | ARG | 831 | 32.469 | 50.756 | 22.885 | 1.00 12.04 |
| ATOM | 123 | NH1 | ARG | 831 | 32.688 | 49.518 | 23.234 | 1.00 23.80 |
| ATOM | 126 | NH2 | ARG | 831 | 33.467 | 51.501 | 22.526 | 1.00 23.84 |
| ATOM | 129 | C | ARG | 831 | 26.625 | 50.415 | 19.174 | 1.00 18.55 |
| ATOM | 130 | O | ARG | 831 | 25.852 | 49.561 | 19.607 | 1.00 25.61 |
| ATOM | 131 | N | ASP | 832 | 26.221 | 51.517 | 18.552 | 1.00 25.32 |
| ATOM | 133 | CA | ASP | 832 | 24.794 | 51.734 | 18.354 | 1.00 29.47 |
| ATOM | 134 | CB | ASP | 832 | 24.393 | 53.230 | 18.408 | 1.00 34.15 |
| ATOM | 135 | CG | ASP | 832 | 24.817 | 54.036 | 17.174 | 1.00 33.50 |
| ATOM | 136 | OD1 | ASP | 832 | 25.519 | 53.528 | 16.280 | 1.00 34.09 |
| ATOM | 137 | OD2 | ASP | 832 | 24.422 | 55.216 | 17.110 | 1.00 41.48 |
| ATOM | 138 | C | ASP | 832 | 24.230 | 51.000 | 17.139 | 1.00 27.13 |
| ATOM | 139 | O | ASP | 832 | 23.023 | 50.905 | 16.991 | 1.00 28.08 |
| ATOM | 140 | N | ARG | 833 | 25.104 | 50.466 | 16.290 | 1.00 24.18 |
| ATOM | 142 | CA | ARG | 833 | 24.684 | 49.695 | 15.134 | 1.00 19.93 |
| ATOM | 143 | CB | ARG | 833 | 25.661 | 49.902 | 14.011 | 1.00 25.94 |
| ATOM | 144 | CG | ARG | 833 | 25.313 | 51.073 | 13.158 | 1.00 38.97 |
| ATOM | 145 | CD | ARG | 833 | 25.929 | 50.901 | 11.766 | 1.00 53.19 |
| ATOM | 146 | NE | ARG | 833 | 25.525 | 51.930 | 10.807 | 1.00 63.47 |
| ATOM | 148 | CZ | ARG | 833 | 25.419 | 53.229 | 11.087 | 1.00 70.42 |
| ATOM | 149 | NH1 | ARG | 833 | 25.040 | 54.080 | 10.139 | 1.00 74.08 |
| ATOM | 152 | NH2 | ARG | 833 | 25.695 | 53.690 | 12.306 | 1.00 72.08 |
| ATOM | 155 | C | ARG | 833 | 24.656 | 48.218 | 15.498 | 1.00 18.62 |

FIG. 7(4)

| | | | | | | | | |
|---|---|---|---|---|---|---|---|---|
| ATOM | 156 | O   | ARG  | 833 | 24.289 | 47.370 | 14.690 | 1.00 18.27 |
| ATOM | 157 | N   | LEU  | 834 | 25.013 | 47.943 | 16.747 | 1.00 18.35 |
| ATOM | 159 | CA  | LEU  | 834 | 25.089 | 46.600 | 17.329 | 1.00 22.59 |
| ATOM | 160 | CB  | LEU  | 834 | 26.488 | 46.398 | 17.946 | 1.00 25.91 |
| ATOM | 161 | CG  | LEU  | 834 | 27.073 | 45.003 | 18.139 | 1.00 24.64 |
| ATOM | 162 | CD1 | LEU  | 834 | 27.185 | 44.327 | 16.805 | 1.00 21.77 |
| ATOM | 163 | CD2 | LEU  | 834 | 28.428 | 45.085 | 18.785 | 1.00 17.43 |
| ATOM | 164 | C   | LEU  | 834 | 23.988 | 46.326 | 18.387 | 1.00 24.77 |
| ATOM | 165 | O   | LEU  | 834 | 23.886 | 46.973 | 19.433 | 1.00 24.03 |
| ATOM | 166 | N   | LYS  | 835 | 23.173 | 45.335 | 18.087 | 1.00 28.94 |
| ATOM | 168 | CA  | LYS  | 835 | 22.072 | 44.942 | 18.940 | 1.00 32.84 |
| ATOM | 169 | CB  | LYS  | 835 | 20.794 | 44.913 | 18.081 | 1.00 31.34 |
| ATOM | 170 | CG  | LYS  | 835 | 19.529 | 44.697 | 18.839 | 1.00 36.63 |
| ATOM | 171 | CD  | LYS  | 835 | 18.359 | 44.407 | 17.940 | 1.00 39.31 |
| ATOM | 172 | CE  | LYS  | 835 | 17.074 | 44.414 | 18.783 | 1.00 48.99 |
| ATOM | 173 | NZ  | LYS  | 835 | 17.074 | 43.448 | 19.950 | 1.00 48.86 |
| ATOM | 177 | C   | LYS  | 835 | 22.431 | 43.532 | 19.420 | 1.00 31.79 |
| ATOM | 178 | O   | LYS  | 835 | 22.408 | 42.609 | 18.616 | 1.00 34.57 |
| ATOM | 179 | N   | LEU  | 836 | 22.854 | 43.395 | 20.680 | 1.00 33.17 |
| ATOM | 181 | CA  | LEU  | 836 | 23.229 | 42.101 | 21.277 | 1.00 34.01 |
| ATOM | 182 | CB  | LEU  | 836 | 23.970 | 42.292 | 22.593 | 1.00 33.96 |
| ATOM | 183 | CG  | LEU  | 836 | 25.400 | 42.796 | 22.462 | 1.00 42.50 |
| ATOM | 184 | CD1 | LEU  | 836 | 26.082 | 42.858 | 23.854 | 1.00 41.15 |
| ATOM | 185 | CD2 | LEU  | 836 | 26.153 | 41.860 | 21.501 | 1.00 40.93 |
| ATOM | 186 | C   | LEU  | 836 | 22.053 | 41.181 | 21.547 | 1.00 33.27 |
| ATOM | 187 | O   | LEU  | 836 | 21.017 | 41.631 | 22.025 | 1.00 31.15 |
| ATOM | 188 | N   | GLY  | 837 | 22.268 | 39.882 | 21.330 | 1.00 36.34 |
| ATOM | 190 | CA  | GLY  | 837 | 21.228 | 38.881 | 21.536 | 1.00 34.95 |
| ATOM | 191 | C   | GLY  | 837 | 21.603 | 37.761 | 22.497 | 1.00 35.64 |
| ATOM | 192 | O   | GLY  | 837 | 22.203 | 37.980 | 23.554 | 1.00 39.23 |
| ATOM | 193 | N   | LYS  | 838 | 21.254 | 36.541 | 22.126 | 1.00 35.31 |
| ATOM | 195 | CA  | LYS  | 838 | 21.531 | 35.375 | 22.962 | 1.00 37.86 |
| ATOM | 196 | CB  | LYS  | 838 | 20.647 | 34.192 | 22.539 | 1.00 41.52 |
| ATOM | 197 | C   | LYS  | 838 | 22.991 | 34.935 | 22.989 | 1.00 35.93 |
| ATOM | 198 | O   | LYS  | 838 | 23.650 | 34.851 | 21.946 | 1.00 34.37 |
| ATOM | 199 | N   | PRO  | 839 | 23.499 | 34.608 | 24.187 | 1.00 33.68 |
| ATOM | 200 | CD  | PRO  | 839 | 22.820 | 34.757 | 25.486 | 1.00 34.48 |
| ATOM | 201 | CA  | PRO  | 839 | 24.880 | 34.158 | 24.363 | 1.00 37.11 |
| ATOM | 202 | CB  | PRO  | 839 | 24.927 | 33.750 | 25.833 | 1.00 37.46 |
| ATOM | 203 | CG  | PRO  | 839 | 23.970 | 34.710 | 26.472 | 1.00 37.04 |
| ATOM | 204 | C   | PRO  | 839 | 25.148 | 32.963 | 23.474 | 1.00 39.09 |
| ATOM | 205 | O   | PRO  | 839 | 24.303 | 32.085 | 23.327 | 1.00 38.13 |
| ATOM | 206 | N   | LEU  | 840 | 26.261 | 33.013 | 22.767 | 1.00 43.08 |

FIG. 7(5)

| | | | | | | | |
|---|---|---|---|---|---|---|---|
| ATOM | 208 | CA | LEU | 840 | 26.646 | 31.915 | 21.917 1.00 47.73 |
| ATOM | 209 | CB | LEU | 840 | 27.396 | 32.426 | 20.692 1.00 41.83 |
| ATOM | 210 | CG | LEU | 840 | 26.386 | 32.957 | 19.697 1.00 39.60 |
| ATOM | 211 | CD1 | LEU | 840 | 27.080 | 33.697 | 18.595 1.00 42.69 |
| ATOM | 212 | CD2 | LEU | 840 | 25.582 | 31.795 | 19.156 1.00 38.40 |
| ATOM | 213 | C | LEU | 840 | 27.523 | 30.987 | 22.747 1.00 54.84 |
| ATOM | 214 | O | LEU | 840 | 27.479 | 29.768 | 22.577 1.00 59.76 |
| ATOM | 215 | N | GLY | 841 | 28.248 | 31.563 | 23.706 1.00 60.51 |
| ATOM | 217 | CA | GLY | 841 | 29.140 | 30.781 | 24.547 1.00 60.96 |
| ATOM | 218 | C | GLY | 841 | 29.660 | 31.544 | 25.750 1.00 63.95 |
| ATOM | 219 | O | GLY | 841 | 29.497 | 32.764 | 25.857 1.00 64.35 |
| ATOM | 220 | N | ARG | 842 | 30.279 | 30.809 | 26.668 1.00 65.26 |
| ATOM | 222 | CA | ARG | 842 | 30.823 | 31.388 | 27.887 1.00 65.12 |
| ATOM | 223 | CB | ARG | 842 | 30.027 | 30.897 | 29.091 1.00 61.50 |
| ATOM | 224 | C | ARG | 842 | 32.300 | 30.995 | 28.004 1.00 64.23 |
| ATOM | 225 | O | ARG | 842 | 32.957 | 30.720 | 26.986 1.00 68.80 |
| ATOM | 226 | N | GLY | 843 | 32.822 | 31.003 | 29.226 1.00 60.14 |
| ATOM | 228 | CA | GLY | 843 | 34.206 | 30.639 | 29.453 1.00 60.53 |
| ATOM | 229 | C | GLY | 843 | 34.676 | 31.165 | 30.789 1.00 62.56 |
| ATOM | 230 | O | GLY | 843 | 33.902 | 31.764 | 31.535 1.00 61.31 |
| ATOM | 231 | N | ALA | 844 | 35.925 | 30.888 | 31.140 1.00 66.30 |
| ATOM | 233 | CA | ALA | 844 | 36.450 | 31.390 | 32.403 1.00 69.69 |
| ATOM | 234 | CB | ALA | 844 | 37.655 | 30.574 | 32.851 1.00 68.47 |
| ATOM | 235 | C | ALA | 844 | 36.839 | 32.855 | 32.212 1.00 73.15 |
| ATOM | 236 | O | ALA | 844 | 36.723 | 33.667 | 33.144 1.00 75.00 |
| ATOM | 237 | N | PHE | 845 | 37.251 | 33.184 | 30.981 1.00 76.12 |
| ATOM | 239 | CA | PHE | 845 | 37.699 | 34.538 | 30.618 1.00 74.99 |
| ATOM | 240 | CB | PHE | 845 | 39.135 | 34.479 | 30.014 1.00 72.01 |
| ATOM | 241 | C | PHE | 845 | 36.766 | 35.353 | 29.700 1.00 73.81 |
| ATOM | 242 | O | PHE | 845 | 36.404 | 36.499 | 30.020 1.00 76.82 |
| ATOM | 243 | N | GLY | 846 | 36.368 | 34.767 | 28.576 1.00 68.48 |
| ATOM | 245 | CA | GLY | 846 | 35.527 | 35.495 | 27.645 1.00 61.76 |
| ATOM | 246 | C | GLY | 846 | 34.102 | 35.023 | 27.606 1.00 57.98 |
| ATOM | 247 | O | GLY | 846 | 33.658 | 34.305 | 28.491 1.00 59.43 |
| ATOM | 248 | N | GLN | 847 | 33.400 | 35.413 | 26.553 1.00 55.08 |
| ATOM | 250 | CA | GLN | 847 | 32.006 | 35.050 | 26.354 1.00 52.26 |
| ATOM | 251 | CB | GLN | 847 | 31.160 | 35.668 | 27.449 1.00 55.14 |
| ATOM | 252 | CG | GLN | 847 | 29.706 | 35.703 | 27.075 1.00 61.40 |
| ATOM | 253 | CD | GLN | 847 | 28.951 | 36.735 | 27.844 1.00 65.75 |
| ATOM | 254 | OE1 | GLN | 847 | 27.772 | 36.543 | 28.150 1.00 69.74 |
| ATOM | 255 | NE2 | GLN | 847 | 29.614 | 37.852 | 28.166 1.00 68.83 |
| ATOM | 258 | C | GLN | 847 | 31.508 | 35.573 | 25.001 1.00 47.29 |
| ATOM | 259 | O | GLN | 847 | 31.637 | 36.764 | 24.713 1.00 52.89 |

FIG. 7(6)

| | | | | | | | | |
|---|---|---|---|---|---|---|---|---|
| ATOM | 260 | N | VAL | 848 | 30.912 | 34.707 | 24.195 | 1.00 38.17 |
| ATOM | 262 | CA | VAL | 848 | 30.418 | 35.122 | 22.898 | 1.00 30.28 |
| ATOM | 263 | CB | VAL | 848 | 30.792 | 34.137 | 21.833 | 1.00 28.01 |
| ATOM | 264 | CG1 | VAL | 848 | 30.542 | 34.744 | 20.442 | 1.00 23.32 |
| ATOM | 265 | CG2 | VAL | 848 | 32.239 | 33.759 | 22.016 | 1.00 22.18 |
| ATOM | 266 | C | VAL | 848 | 28.920 | 35.262 | 22.939 | 1.00 31.80 |
| ATOM | 267 | O | VAL | 848 | 28.221 | 34.525 | 23.625 | 1.00 32.87 |
| ATOM | 268 | N | ILE | 849 | 28.410 | 36.196 | 22.166 | 1.00 29.87 |
| ATOM | 270 | CA | ILE | 849 | 26.990 | 36.436 | 22.159 | 1.00 25.35 |
| ATOM | 271 | CB | ILE | 849 | 26.602 | 37.448 | 23.328 | 1.00 31.46 |
| ATOM | 272 | CG2 | ILE | 849 | 27.766 | 38.373 | 23.732 | 1.00 32.09 |
| ATOM | 273 | CG1 | ILE | 849 | 25.353 | 38.244 | 23.003 | 1.00 31.00 |
| ATOM | 274 | CD1 | ILE | 849 | 24.895 | 39.035 | 24.199 | 1.00 37.56 |
| ATOM | 275 | C | ILE | 849 | 26.493 | 36.851 | 20.798 | 1.00 23.02 |
| ATOM | 276 | O | ILE | 849 | 27.167 | 37.540 | 20.070 | 1.00 27.56 |
| ATOM | 277 | N | GLU | 850 | 25.376 | 36.294 | 20.390 | 1.00 25.56 |
| ATOM | 279 | CA | GLU | 850 | 24.802 | 36.626 | 19.107 | 1.00 26.63 |
| ATOM | 280 | CB | GLU | 850 | 23.577 | 35.785 | 18.894 | 1.00 27.45 |
| ATOM | 281 | CG | GLU | 850 | 23.414 | 35.361 | 17.487 | 1.00 34.57 |
| ATOM | 282 | CD | GLU | 850 | 22.155 | 34.590 | 17.293 | 1.00 34.46 |
| ATOM | 283 | OE1 | GLU | 850 | 21.602 | 34.655 | 16.184 | 1.00 42.38 |
| ATOM | 284 | OE2 | GLU | 850 | 21.710 | 33.924 | 18.248 | 1.00 40.93 |
| ATOM | 285 | C | GLU | 850 | 24.422 | 38.111 | 19.028 | 1.00 27.83 |
| ATOM | 286 | O | GLU | 850 | 24.240 | 38.755 | 20.047 | 1.00 25.02 |
| ATOM | 287 | N | ALA | 851 | 24.291 | 38.640 | 17.814 | 1.00 29.11 |
| ATOM | 289 | CA | ALA | 851 | 23.958 | 40.043 | 17.621 | 1.00 27.32 |
| ATOM | 290 | CB | ALA | 851 | 25.080 | 40.922 | 18.170 | 1.00 18.65 |
| ATOM | 291 | C | ALA | 851 | 23.731 | 40.387 | 16.160 | 1.00 26.61 |
| ATOM | 292 | O | ALA | 851 | 24.328 | 39.785 | 15.283 | 1.00 26.99 |
| ATOM | 293 | N | ASP | 852 | 22.836 | 41.343 | 15.917 | 1.00 30.82 |
| ATOM | 295 | CA | ASP | 852 | 22.538 | 41.862 | 14.566 | 1.00 31.76 |
| ATOM | 296 | CB | ASP | 852 | 21.050 | 42.186 | 14.386 | 1.00 39.33 |
| ATOM | 297 | CG | ASP | 852 | 20.222 | 40.993 | 13.993 | 1.00 47.41 |
| ATOM | 298 | OD1 | ASP | 852 | 19.687 | 40.330 | 14.906 | 1.00 54.12 |
| ATOM | 299 | OD2 | ASP | 852 | 20.066 | 40.754 | 12.775 | 1.00 53.02 |
| ATOM | 300 | C | ASP | 852 | 23.265 | 43.204 | 14.506 | 1.00 25.97 |
| ATOM | 301 | O | ASP | 852 | 23.096 | 44.021 | 15.416 | 1.00 21.64 |
| ATOM | 302 | N | ALA | 853 | 24.099 | 43.411 | 13.495 | 1.00 20.18 |
| ATOM | 304 | CA | ALA | 853 | 24.818 | 44.672 | 13.342 | 1.00 23.55 |
| ATOM | 305 | CB | ALA | 853 | 26.305 | 44.440 | 13.292 | 1.00 23.32 |
| ATOM | 306 | C | ALA | 853 | 24.311 | 45.222 | 12.026 | 1.00 23.89 |
| ATOM | 307 | O | ALA | 853 | 24.079 | 44.439 | 11.108 | 1.00 26.15 |
| ATOM | 308 | N | PHE | 854 | 24.044 | 46.526 | 11.936 | 1.00 22.87 |

FIG. 7(7)

| | | | | | | | |
|---|---|---|---|---|---|---|---|
| ATOM | 310 | CA  | PHE | 854 | 23.529 | 47.059 | 10.680 1.00 16.46 |
| ATOM | 311 | CB  | PHE | 854 | 22.487 | 48.135 | 10.901 1.00 23.71 |
| ATOM | 312 | CG  | PHE | 854 | 22.020 | 48.758 | 9.643 1.00 27.62 |
| ATOM | 313 | CD1 | PHE | 854 | 22.476 | 50.011 | 9.266 1.00 28.26 |
| ATOM | 314 | CD2 | PHE | 854 | 21.205 | 48.052 | 8.771 1.00 31.56 |
| ATOM | 315 | CE1 | PHE | 854 | 22.136 | 50.549 | 8.025 1.00 30.16 |
| ATOM | 316 | CE2 | PHE | 854 | 20.856 | 48.592 | 7.512 1.00 34.04 |
| ATOM | 317 | CZ  | PHE | 854 | 21.328 | 49.838 | 7.145 1.00 28.32 |
| ATOM | 318 | C   | PHE | 854 | 24.618 | 47.569 | 9.794 1.00 14.10 |
| ATOM | 319 | O   | PHE | 854 | 25.493 | 48.299 | 10.209 1.00 17.34 |
| ATOM | 320 | N   | GLY | 855 | 24.556 | 47.163 | 8.553 1.00 17.45 |
| ATOM | 322 | CA  | GLY | 855 | 25.559 | 47.571 | 7.604 1.00 18.50 |
| ATOM | 323 | C   | GLY | 855 | 26.988 | 47.318 | 8.020 1.00 22.65 |
| ATOM | 324 | O   | GLY | 855 | 27.806 | 48.193 | 7.777 1.00 26.82 |
| ATOM | 325 | N   | ILE | 856 | 27.332 | 46.150 | 8.580 1.00 23.51 |
| ATOM | 327 | CA  | ILE | 856 | 28.740 | 45.886 | 8.983 1.00 24.11 |
| ATOM | 328 | CB  | ILE | 856 | 28.868 | 44.692 | 9.980 1.00 27.72 |
| ATOM | 329 | CG2 | ILE | 856 | 28.535 | 43.370 | 9.259 1.00 29.88 |
| ATOM | 330 | CG1 | ILE | 856 | 30.282 | 44.663 | 10.608 1.00 23.26 |
| ATOM | 331 | CD1 | ILE | 856 | 30.371 | 44.079 | 12.034 1.00 21.70 |
| ATOM | 332 | C   | ILE | 856 | 29.704 | 45.665 | 7.805 1.00 24.83 |
| ATOM | 333 | O   | ILE | 856 | 30.918 | 45.721 | 7.950 1.00 28.37 |
| ATOM | 334 | N   | ASP | 857 | 29.145 | 45.460 | 6.626 1.00 27.69 |
| ATOM | 336 | CA  | ASP | 857 | 29.926 | 45.248 | 5.420 1.00 31.23 |
| ATOM | 337 | CB  | ASP | 857 | 29.566 | 43.891 | 4.838 1.00 34.80 |
| ATOM | 338 | CG  | ASP | 857 | 28.074 | 43.658 | 4.811 1.00 40.03 |
| ATOM | 339 | OD1 | ASP | 857 | 27.328 | 44.597 | 4.448 1.00 43.33 |
| ATOM | 340 | OD2 | ASP | 857 | 27.641 | 42.549 | 5.200 1.00 46.87 |
| ATOM | 341 | C   | ASP | 857 | 29.654 | 46.323 | 4.370 1.00 32.81 |
| ATOM | 342 | O   | ASP | 857 | 29.721 | 46.040 | 3.183 1.00 38.59 |
| ATOM | 343 | N   | LYS | 858 | 29.299 | 47.529 | 4.813 1.00 34.74 |
| ATOM | 345 | CA  | LYS | 858 | 28.987 | 48.690 | 3.946 1.00 34.64 |
| ATOM | 346 | CB  | LYS | 858 | 30.061 | 48.947 | 2.889 1.00 31.38 |
| ATOM | 347 | CG  | LYS | 858 | 31.462 | 48.964 | 3.418 1.00 34.36 |
| ATOM | 348 | CD  | LYS | 858 | 31.605 | 49.890 | 4.603 1.00 39.41 |
| ATOM | 349 | CE  | LYS | 858 | 33.005 | 49.791 | 5.228 1.00 39.87 |
| ATOM | 350 | NZ  | LYS | 858 | 34.059 | 50.089 | 4.218 1.00 39.89 |
| ATOM | 354 | C   | LYS | 858 | 27.629 | 48.709 | 3.254 1.00 32.27 |
| ATOM | 355 | O   | LYS | 858 | 27.249 | 49.737 | 2.724 1.00 35.02 |
| ATOM | 356 | N   | THR | 859 | 26.891 | 47.607 | 3.258 1.00 32.20 |
| ATOM | 358 | CA  | THR | 859 | 25.597 | 47.610 | 2.600 1.00 30.11 |
| ATOM | 359 | CB  | THR | 859 | 25.355 | 46.332 | 1.785 1.00 30.38 |
| ATOM | 360 | OG1 | THR | 859 | 25.365 | 45.187 | 2.641 1.00 32.29 |

FIG. 7(8)

| | | | | | | | |
|---|---|---|---|---|---|---|---|
| ATOM | 362 | CG2 | THR | 859 | 26.437 | 46.179 | 0.757 | 1.00 | 32.22 |
| ATOM | 363 | C | THR | 859 | 24.450 | 47.839 | 3.546 | 1.00 | 28.71 |
| ATOM | 364 | O | THR | 859 | 24.577 | 47.647 | 4.750 | 1.00 | 30.55 |
| ATOM | 365 | N | ALA | 860 | 23.303 | 48.201 | 2.989 | 1.00 | 30.07 |
| ATOM | 367 | CA | ALA | 860 | 22.123 | 48.474 | 3.784 | 1.00 | 28.01 |
| ATOM | 368 | CB | ALA | 860 | 21.141 | 49.253 | 2.928 | 1.00 | 23.78 |
| ATOM | 369 | C | ALA | 860 | 21.461 | 47.222 | 4.394 | 1.00 | 28.00 |
| ATOM | 370 | O | ALA | 860 | 20.251 | 47.100 | 4.373 | 1.00 | 31.77 |
| ATOM | 371 | N | THR | 861 | 22.228 | 46.325 | 5.008 | 1.00 | 29.99 |
| ATOM | 373 | CA | THR | 861 | 21.663 | 45.078 | 5.577 | 1.00 | 27.77 |
| ATOM | 374 | CB | THR | 861 | 22.186 | 43.857 | 4.808 | 1.00 | 20.97 |
| ATOM | 375 | OG1 | THR | 861 | 23.614 | 43.926 | 4.687 | 1.00 | 27.23 |
| ATOM | 377 | CG2 | THR | 861 | 21.608 | 43.794 | 3.449 | 1.00 | 29.39 |
| ATOM | 378 | C | THR | 861 | 21.986 | 44.790 | 7.055 | 1.00 | 31.89 |
| ATOM | 379 | O | THR | 861 | 23.095 | 45.077 | 7.532 | 1.00 | 34.73 |
| ATOM | 380 | N | CYS | 862 | 21.037 | 44.183 | 7.770 | 1.00 | 34.09 |
| ATOM | 382 | CA | CYS | 862 | 21.250 | 43.805 | 9.178 | 1.00 | 31.63 |
| ATOM | 383 | CB | CYS | 862 | 19.922 | 43.756 | 9.943 | 1.00 | 27.50 |
| ATOM | 384 | SG | CYS | 862 | 19.863 | 44.908 | 11.327 | 1.00 | 41.79 |
| ATOM | 385 | C | CYS | 862 | 21.876 | 42.424 | 9.146 | 1.00 | 25.51 |
| ATOM | 386 | O | CYS | 862 | 21.241 | 41.492 | 8.700 | 1.00 | 30.38 |
| ATOM | 387 | N | ARG | 863 | 23.136 | 42.307 | 9.541 | 1.00 | 27.68 |
| ATOM | 389 | CA | ARG | 863 | 23.839 | 41.025 | 9.532 | 1.00 | 28.29 |
| ATOM | 390 | CB | ARG | 863 | 25.211 | 41.210 | 8.882 | 1.00 | 36.18 |
| ATOM | 391 | CG | ARG | 863 | 25.775 | 39.945 | 8.275 | 1.00 | 48.71 |
| ATOM | 392 | CD | ARG | 863 | 27.282 | 40.034 | 7.943 | 1.00 | 58.46 |
| ATOM | 393 | NE | ARG | 863 | 27.824 | 38.721 | 7.550 | 1.00 | 65.04 |
| ATOM | 395 | CZ | ARG | 863 | 29.112 | 38.452 | 7.330 | 1.00 | 65.66 |
| ATOM | 396 | NH1 | ARG | 863 | 29.482 | 37.219 | 6.985 | 1.00 | 67.60 |
| ATOM | 399 | NH2 | ARG | 863 | 30.030 | 39.409 | 7.421 | 1.00 | 66.49 |
| ATOM | 402 | C | ARG | 863 | 24.006 | 40.409 | 10.943 | 1.00 | 28.34 |
| ATOM | 403 | O | ARG | 863 | 24.337 | 41.125 | 11.904 | 1.00 | 24.64 |
| ATOM | 404 | N | THR | 864 | 23.735 | 39.100 | 11.078 | 1.00 | 23.23 |
| ATOM | 406 | CA | THR | 864 | 23.900 | 38.426 | 12.364 | 1.00 | 18.91 |
| ATOM | 407 | CB | THR | 864 | 23.062 | 37.099 | 12.489 | 1.00 | 19.40 |
| ATOM | 408 | OG1 | THR | 864 | 21.672 | 37.435 | 12.547 | 1.00 | 24.20 |
| ATOM | 410 | CG2 | THR | 864 | 23.371 | 36.351 | 13.793 | 1.00 | 8.83 |
| ATOM | 411 | C | THR | 864 | 25.385 | 38.148 | 12.462 | 1.00 | 20.93 |
| ATOM | 412 | O | THR | 864 | 26.001 | 37.736 | 11.468 | 1.00 | 20.14 |
| ATOM | 413 | N | VAL | 865 | 25.962 | 38.442 | 13.634 | 1.00 | 16.03 |
| ATOM | 415 | CA | VAL | 865 | 27.381 | 38.254 | 13.897 | 1.00 | 16.69 |
| ATOM | 416 | CB | VAL | 865 | 28.175 | 39.620 | 13.906 | 1.00 | 17.70 |
| ATOM | 417 | CG1 | VAL | 865 | 28.107 | 40.299 | 12.539 | 1.00 | 21.22 |

FIG. 7(9)

| | | | | | | | | |
|---|---|---|---|---|---|---|---|---|
| ATOM | 418 | CG2 | VAL | 865 | 27.625 | 40.554 | 14.979 | 1.00 20.92 |
| ATOM | 419 | C | VAL | 865 | 27.533 | 37.660 | 15.276 | 1.00 15.90 |
| ATOM | 420 | O | VAL | 865 | 26.552 | 37.554 | 15.995 | 1.00 16.43 |
| ATOM | 421 | N | ALA | 866 | 28.775 | 37.295 | 15.612 | 1.00 16.37 |
| ATOM | 423 | CA | ALA | 866 | 29.210 | 36.753 | 16.910 | 1.00 18.08 |
| ATOM | 424 | CB | ALA | 866 | 30.022 | 35.490 | 16.691 | 1.00 7.41 |
| ATOM | 425 | C | ALA | 866 | 30.117 | 37.834 | 17.588 | 1.00 23.87 |
| ATOM | 426 | O | ALA | 866 | 31.121 | 38.261 | 16.998 | 1.00 24.17 |
| ATOM | 427 | N | VAL | 867 | 29.790 | 38.235 | 18.827 | 1.00 26.69 |
| ATOM | 429 | CA | VAL | 867 | 30.534 | 39.268 | 19.554 | 1.00 20.37 |
| ATOM | 430 | CB | VAL | 867 | 29.592 | 40.365 | 20.088 | 1.00 17.71 |
| ATOM | 431 | CG1 | VAL | 867 | 30.361 | 41.586 | 20.519 | 1.00 9.32 |
| ATOM | 432 | CG2 | VAL | 867 | 28.635 | 40.753 | 19.027 | 1.00 14.57 |
| ATOM | 433 | C | VAL | 867 | 31.320 | 38.748 | 20.728 | 1.00 21.67 |
| ATOM | 434 | O | VAL | 867 | 30.784 | 38.085 | 21.606 | 1.00 23.57 |
| ATOM | 435 | N | LYS | 868 | 32.616 | 38.982 | 20.694 | 1.00 21.65 |
| ATOM | 437 | CA | LYS | 868 | 33.471 | 38.593 | 21.782 | 1.00 27.02 |
| ATOM | 438 | CB | LYS | 868 | 34.860 | 38.169 | 21.289 | 1.00 29.71 |
| ATOM | 439 | CG | LYS | 868 | 34.842 | 36.963 | 20.405 | 1.00 37.08 |
| ATOM | 440 | CD | LYS | 868 | 36.151 | 36.810 | 19.666 | 1.00 44.81 |
| ATOM | 441 | CE | LYS | 868 | 36.183 | 35.512 | 18.868 | 1.00 45.52 |
| ATOM | 442 | NZ | LYS | 868 | 37.548 | 35.298 | 18.274 | 1.00 47.28 |
| ATOM | 446 | C | LYS | 868 | 33.585 | 39.842 | 22.647 | 1.00 26.11 |
| ATOM | 447 | O | LYS | 868 | 33.962 | 40.914 | 22.188 | 1.00 24.72 |
| ATOM | 448 | N | MET | 869 | 33.184 | 39.721 | 23.888 | 1.00 29.77 |
| ATOM | 450 | CA | MET | 869 | 33.299 | 40.821 | 24.803 | 1.00 32.95 |
| ATOM | 451 | CB | MET | 869 | 31.958 | 41.491 | 24.996 | 1.00 30.57 |
| ATOM | 452 | CG | MET | 869 | 30.900 | 40.542 | 25.463 | 1.00 32.29 |
| ATOM | 453 | SD | MET | 869 | 29.348 | 41.157 | 24.961 | 1.00 42.68 |
| ATOM | 454 | CE | MET | 869 | 29.251 | 42.663 | 25.919 | 1.00 35.32 |
| ATOM | 455 | C | MET | 869 | 33.778 | 40.205 | 26.095 | 1.00 40.29 |
| ATOM | 456 | O | MET | 869 | 33.921 | 38.967 | 26.216 | 1.00 35.26 |
| ATOM | 457 | N | LEU | 870 | 34.079 | 41.066 | 27.051 | 1.00 46.88 |
| ATOM | 459 | CA | LEU | 870 | 34.521 | 40.576 | 28.337 | 1.00 51.36 |
| ATOM | 460 | CB | LEU | 870 | 35.544 | 41.549 | 28.937 | 1.00 48.55 |
| ATOM | 461 | CG | LEU | 870 | 36.862 | 41.677 | 28.180 | 1.00 44.32 |
| ATOM | 462 | CD1 | LEU | 870 | 37.734 | 42.739 | 28.855 | 1.00 36.89 |
| ATOM | 463 | CD2 | LEU | 870 | 37.535 | 40.306 | 28.149 | 1.00 41.04 |
| ATOM | 464 | C | LEU | 870 | 33.344 | 40.306 | 29.311 | 1.00 53.63 |
| ATOM | 465 | O | LEU | 870 | 32.163 | 40.615 | 29.037 | 1.00 52.68 |
| ATOM | 466 | N | LYS | 871 | 33.675 | 39.644 | 30.412 | 1.00 56.89 |
| ATOM | 468 | CA | LYS | 871 | 32.695 | 39.346 | 31.426 | 1.00 58.53 |
| ATOM | 469 | CB | LYS | 871 | 33.083 | 38.077 | 32.169 | 1.00 59.89 |

FIG. 7(10)

| ATOM | 470 | CG | LYS | 871 | 31.903 | 37.220 | 32.546 | 1.00 | 63.81 |
|---|---|---|---|---|---|---|---|---|---|
| ATOM | 471 | CD | LYS | 871 | 31.912 | 35.965 | 31.719 | 1.00 | 65.43 |
| ATOM | 472 | CE | LYS | 871 | 33.268 | 35.318 | 31.853 | 1.00 | 70.59 |
| ATOM | 473 | NZ | LYS | 871 | 33.318 | 34.051 | 31.135 | 1.00 | 76.57 |
| ATOM | 477 | C | LYS | 871 | 32.649 | 40.518 | 32.404 | 1.00 | 59.44 |
| ATOM | 478 | O | LYS | 871 | 33.582 | 41.342 | 32.464 | 1.00 | 56.75 |
| ATOM | 479 | N | GLU | 872 | 31.566 | 40.571 | 33.177 | 1.00 | 61.50 |
| ATOM | 481 | CA | GLU | 872 | 31.357 | 41.618 | 34.177 | 1.00 | 64.12 |
| ATOM | 482 | CB | GLU | 872 | 29.928 | 41.539 | 34.739 | 1.00 | 66.85 |
| ATOM | 483 | CG | GLU | 872 | 28.846 | 41.903 | 33.729 | 1.00 | 71.27 |
| ATOM | 484 | CD | GLU | 872 | 29.060 | 41.218 | 32.387 | 1.00 | 74.41 |
| ATOM | 485 | OE1 | GLU | 872 | 28.900 | 39.980 | 32.326 | 1.00 | 76.27 |
| ATOM | 486 | OE2 | GLU | 872 | 29.443 | 41.903 | 31.411 | 1.00 | 74.20 |
| ATOM | 487 | C | GLU | 872 | 32.387 | 41.424 | 35.288 | 1.00 | 60.87 |
| ATOM | 488 | O | GLU | 872 | 32.331 | 40.441 | 36.026 | 1.00 | 61.34 |
| ATOM | 489 | N | GLY | 873 | 33.368 | 42.319 | 35.335 | 1.00 | 57.40 |
| ATOM | 491 | CA | GLY | 873 | 34.408 | 42.223 | 36.337 | 1.00 | 53.93 |
| ATOM | 492 | C | GLY | 873 | 35.703 | 41.641 | 35.803 | 1.00 | 52.30 |
| ATOM | 493 | O | GLY | 873 | 36.518 | 41.103 | 36.563 | 1.00 | 51.95 |
| ATOM | 494 | N | ALA | 874 | 35.881 | 41.721 | 34.491 | 1.00 | 51.13 |
| ATOM | 496 | CA | ALA | 874 | 37.090 | 41.217 | 33.862 | 1.00 | 51.21 |
| ATOM | 497 | CB | ALA | 874 | 36.875 | 41.049 | 32.335 | 1.00 | 48.57 |
| ATOM | 498 | C | ALA | 874 | 38.270 | 42.172 | 34.199 | 1.00 | 50.40 |
| ATOM | 499 | O | ALA | 874 | 38.101 | 43.388 | 34.369 | 1.00 | 48.57 |
| ATOM | 500 | N | THR | 875 | 39.465 | 41.609 | 34.245 | 1.00 | 48.33 |
| ATOM | 502 | CA | THR | 875 | 40.657 | 42.334 | 34.617 | 1.00 | 51.59 |
| ATOM | 503 | CB | THR | 875 | 41.572 | 41.428 | 35.447 | 1.00 | 54.42 |
| ATOM | 504 | OG1 | THR | 875 | 42.677 | 42.184 | 35.937 | 1.00 | 60.69 |
| ATOM | 506 | CG2 | THR | 875 | 42.107 | 40.280 | 34.593 | 1.00 | 60.52 |
| ATOM | 507 | C | THR | 875 | 41.455 | 42.830 | 33.448 | 1.00 | 51.15 |
| ATOM | 508 | O | THR | 875 | 41.395 | 42.263 | 32.372 | 1.00 | 52.26 |
| ATOM | 509 | N | HIS | 876 | 42.343 | 43.770 | 33.733 | 1.00 | 53.93 |
| ATOM | 511 | CA | HIS | 876 | 43.215 | 44.392 | 32.737 | 1.00 | 55.68 |
| ATOM | 512 | CB | HIS | 876 | 44.170 | 45.383 | 33.419 | 1.00 | 54.06 |
| ATOM | 513 | CG | HIS | 876 | 45.609 | 44.980 | 33.361 | 1.00 | 56.52 |
| ATOM | 514 | CD2 | HIS | 876 | 46.595 | 45.314 | 32.487 | 1.00 | 56.83 |
| ATOM | 515 | ND1 | HIS | 876 | 46.191 | 44.149 | 34.297 | 1.00 | 60.22 |
| ATOM | 517 | CE1 | HIS | 876 | 47.472 | 43.992 | 34.009 | 1.00 | 62.12 |
| ATOM | 518 | NE2 | HIS | 876 | 47.739 | 44.689 | 32.916 | 1.00 | 59.66 |
| ATOM | 520 | C | HIS | 876 | 44.003 | 43.385 | 31.898 | 1.00 | 54.72 |
| ATOM | 521 | O | HIS | 876 | 44.510 | 43.712 | 30.810 | 1.00 | 54.08 |
| ATOM | 522 | N | SER | 877 | 44.167 | 42.189 | 32.434 | 1.00 | 52.07 |
| ATOM | 524 | CA | SER | 877 | 44.872 | 41.160 | 31.704 | 1.00 | 53.73 |

FIG. 7(11)

| | | | | | | | | |
|---|---|---|---|---|---|---|---|---|
| ATOM | 525 | CB | SER | 877 | 45.622 | 40.256 | 32.669 | 1.00 57.58 |
| ATOM | 526 | OG | SER | 877 | 46.559 | 41.054 | 33.379 | 1.00 63.62 |
| ATOM | 528 | C | SER | 877 | 43.880 | 40.410 | 30.810 | 1.00 51.29 |
| ATOM | 529 | O | SER | 877 | 44.227 | 39.962 | 29.715 | 1.00 50.11 |
| ATOM | 530 | N | GLU | 878 | 42.629 | 40.320 | 31.246 | 1.00 47.72 |
| ATOM | 532 | CA | GLU | 878 | 41.620 | 39.696 | 30.410 | 1.00 45.39 |
| ATOM | 533 | CB | GLU | 878 | 40.335 | 39.483 | 31.201 | 1.00 48.19 |
| ATOM | 534 | CG | GLU | 878 | 40.383 | 38.191 | 32.013 | 1.00 60.86 |
| ATOM | 535 | CD | GLU | 878 | 39.304 | 38.086 | 33.092 | 1.00 68.27 |
| ATOM | 536 | OE1 | GLU | 878 | 38.448 | 37.162 | 33.027 | 1.00 70.85 |
| ATOM | 537 | OE2 | GLU | 878 | 39.336 | 38.911 | 34.029 | 1.00 67.92 |
| ATOM | 538 | C | GLU | 878 | 41.448 | 40.702 | 29.277 | 1.00 40.09 |
| ATOM | 539 | O | GLU | 878 | 41.536 | 40.365 | 28.104 | 1.00 38.92 |
| ATOM | 540 | N | HIS | 879 | 41.393 | 41.966 | 29.659 | 1.00 34.60 |
| ATOM | 542 | CA | HIS | 879 | 41.252 | 43.072 | 28.732 | 1.00 36.68 |
| ATOM | 543 | CB | HIS | 879 | 41.070 | 44.392 | 29.505 | 1.00 44.03 |
| ATOM | 544 | CG | HIS | 879 | 40.637 | 45.547 | 28.652 | 1.00 43.54 |
| ATOM | 545 | CD2 | HIS | 879 | 39.403 | 46.025 | 28.364 | 1.00 40.08 |
| ATOM | 546 | ND1 | HIS | 879 | 41.529 | 46.307 | 27.917 | 1.00 39.08 |
| ATOM | 548 | CE1 | HIS | 879 | 40.860 | 47.192 | 27.202 | 1.00 40.82 |
| ATOM | 549 | NE2 | HIS | 879 | 39.572 | 47.045 | 27.452 | 1.00 49.01 |
| ATOM | 551 | C | HIS | 879 | 42.455 | 43.172 | 27.797 | 1.00 34.17 |
| ATOM | 552 | O | HIS | 879 | 42.293 | 43.494 | 26.626 | 1.00 33.65 |
| ATOM | 553 | N | ARG | 880 | 43.664 | 42.993 | 28.319 | 1.00 33.25 |
| ATOM | 555 | CA | ARG | 880 | 44.838 | 43.033 | 27.470 | 1.00 29.84 |
| ATOM | 556 | CB | ARG | 880 | 46.124 | 42.932 | 28.299 | 1.00 36.53 |
| ATOM | 557 | CG | ARG | 880 | 46.615 | 41.470 | 28.452 | 1.00 50.57 |
| ATOM | 558 | CD | ARG | 880 | 48.121 | 41.276 | 28.649 | 1.00 56.95 |
| ATOM | 559 | NE | ARG | 880 | 48.555 | 41.748 | 29.960 | 1.00 63.99 |
| ATOM | 561 | CZ | ARG | 880 | 49.030 | 42.967 | 30.175 | 1.00 66.67 |
| ATOM | 562 | NH1 | ARG | 880 | 49.391 | 43.327 | 31.397 | 1.00 66.45 |
| ATOM | 565 | NH2 | ARG | 880 | 49.170 | 43.813 | 29.157 | 1.00 66.52 |
| ATOM | 568 | C | ARG | 880 | 44.741 | 41.799 | 26.533 | 1.00 29.72 |
| ATOM | 569 | O | ARG | 880 | 45.246 | 41.808 | 25.401 | 1.00 21.81 |
| ATOM | 570 | N | ALA | 881 | 44.070 | 40.747 | 27.006 | 1.00 28.49 |
| ATOM | 572 | CA | ALA | 881 | 43.942 | 39.514 | 26.227 | 1.00 31.72 |
| ATOM | 573 | CB | ALA | 881 | 43.587 | 38.342 | 27.142 | 1.00 31.57 |
| ATOM | 574 | C | ALA | 881 | 42.978 | 39.592 | 25.044 | 1.00 29.98 |
| ATOM | 575 | O | ALA | 881 | 43.319 | 39.154 | 23.944 | 1.00 31.95 |
| ATOM | 576 | N | LEU | 882 | 41.766 | 40.099 | 25.273 | 1.00 27.12 |
| ATOM | 578 | CA | LEU | 882 | 40.804 | 40.248 | 24.193 | 1.00 27.43 |
| ATOM | 579 | CB | LEU | 882 | 39.493 | 40.784 | 24.728 | 1.00 23.93 |
| ATOM | 580 | CG | LEU | 882 | 38.402 | 40.925 | 23.662 | 1.00 25.91 |

FIG. 7(12)

| | | | | | | | | |
|---|---|---|---|---|---|---|---|---|
| ATOM | 581 | CD1 | LEU | 882 | 38.435 | 39.722 | 22.743 | 1.00 21.91 |
| ATOM | 582 | CD2 | LEU | 882 | 37.013 | 41.102 | 24.325 | 1.00 23.61 |
| ATOM | 583 | C | LEU | 882 | 41.368 | 41.230 | 23.151 | 1.00 30.62 |
| ATOM | 584 | O | LEU | 882 | 41.312 | 40.982 | 21.945 | 1.00 27.61 |
| ATOM | 585 | N | MET | 883 | 41.940 | 42.325 | 23.643 | 1.00 29.74 |
| ATOM | 587 | CA | MET | 883 | 42.548 | 43.364 | 22.808 | 1.00 30.75 |
| ATOM | 588 | CB | MET | 883 | 43.001 | 44.516 | 23.738 | 1.00 27.47 |
| ATOM | 589 | CG | MET | 883 | 43.432 | 45.828 | 23.084 | 1.00 33.64 |
| ATOM | 590 | SD | MET | 883 | 42.313 | 46.592 | 21.882 | 1.00 33.18 |
| ATOM | 591 | CE | MET | 883 | 41.031 | 47.285 | 22.943 | 1.00 33.54 |
| ATOM | 592 | C | MET | 883 | 43.711 | 42.756 | 21.965 | 1.00 29.92 |
| ATOM | 593 | O | MET | 883 | 43.862 | 43.022 | 20.766 | 1.00 28.38 |
| ATOM | 594 | N | SER | 884 | 44.501 | 41.893 | 22.588 | 1.00 29.75 |
| ATOM | 596 | CA | SER | 884 | 45.597 | 41.231 | 21.912 | 1.00 28.29 |
| ATOM | 597 | CB | SER | 884 | 46.343 | 40.391 | 22.923 | 1.00 32.03 |
| ATOM | 598 | OG | SER | 884 | 47.220 | 39.502 | 22.270 | 1.00 44.59 |
| ATOM | 600 | C | SER | 884 | 45.091 | 40.329 | 20.778 | 1.00 29.39 |
| ATOM | 601 | O | SER | 884 | 45.595 | 40.359 | 19.654 | 1.00 28.92 |
| ATOM | 602 | N | GLU | 885 | 44.084 | 39.526 | 21.071 | 1.00 25.33 |
| ATOM | 604 | CA | GLU | 885 | 43.559 | 38.661 | 20.058 | 1.00 27.47 |
| ATOM | 605 | CB | GLU | 885 | 42.563 | 37.692 | 20.661 | 1.00 31.61 |
| ATOM | 606 | CG | GLU | 885 | 41.142 | 38.108 | 20.642 | 1.00 46.01 |
| ATOM | 607 | CD | GLU | 885 | 40.215 | 36.903 | 20.799 | 1.00 55.19 |
| ATOM | 608 | OE1 | GLU | 885 | 40.018 | 36.469 | 21.964 | 1.00 58.80 |
| ATOM | 609 | OE2 | GLU | 885 | 39.715 | 36.379 | 19.762 | 1.00 54.01 |
| ATOM | 610 | C | GLU | 885 | 42.945 | 39.470 | 18.924 | 1.00 28.59 |
| ATOM | 611 | O | GLU | 885 | 42.833 | 38.983 | 17.805 | 1.00 26.67 |
| ATOM | 612 | N | LEU | 886 | 42.560 | 40.712 | 19.211 | 1.00 27.06 |
| ATOM | 614 | CA | LEU | 886 | 41.994 | 41.594 | 18.205 | 1.00 23.75 |
| ATOM | 615 | CB | LEU | 886 | 41.483 | 42.887 | 18.847 | 1.00 22.79 |
| ATOM | 616 | CG | LEU | 886 | 41.122 | 44.033 | 17.905 | 1.00 17.60 |
| ATOM | 617 | CD1 | LEU | 886 | 39.981 | 43.608 | 16.999 | 1.00 11.98 |
| ATOM | 618 | CD2 | LEU | 886 | 40.747 | 45.285 | 18.702 | 1.00 18.31 |
| ATOM | 619 | C | LEU | 886 | 43.049 | 41.936 | 17.147 | 1.00 24.77 |
| ATOM | 620 | O | LEU | 886 | 42.767 | 41.880 | 15.939 | 1.00 22.15 |
| ATOM | 621 | N | LYS | 887 | 44.265 | 42.246 | 17.602 | 1.00 25.08 |
| ATOM | 623 | CA | LYS | 887 | 45.384 | 42.613 | 16.722 | 1.00 24.94 |
| ATOM | 624 | CB | LYS | 887 | 46.517 | 43.227 | 17.544 | 1.00 29.70 |
| ATOM | 625 | CG | LYS | 887 | 46.105 | 44.304 | 18.560 | 1.00 30.67 |
| ATOM | 626 | CD | LYS | 887 | 45.556 | 45.551 | 17.895 | 1.00 28.99 |
| ATOM | 627 | CE | LYS | 887 | 45.170 | 46.645 | 18.923 | 1.00 26.07 |
| ATOM | 628 | NZ | LYS | 887 | 46.354 | 47.216 | 19.621 | 1.00 17.59 |
| ATOM | 632 | C | LYS | 887 | 45.921 | 41.407 | 15.925 | 1.00 25.59 |

FIG. 7(13)

| | | | | | | | |
|---|---|---|---|---|---|---|---|
| ATOM | 633 | O | LYS | 887 | 46.388 | 41.547 | 14.793 1.00 30.23 |
| ATOM | 634 | N | ILE | 888 | 45.917 | 40.235 | 16.542 1.00 20.48 |
| ATOM | 636 | CA | ILE | 888 | 46.347 | 39.028 | 15.859 1.00 21.46 |
| ATOM | 637 | CB | ILE | 888 | 46.306 | 37.795 | 16.816 1.00 22.73 |
| ATOM | 638 | CG2 | ILE | 888 | 46.604 | 36.556 | 16.047 1.00 24.05 |
| ATOM | 639 | CG1 | ILE | 888 | 47.355 | 37.929 | 17.937 1.00 23.32 |
| ATOM | 640 | CD1 | ILE | 888 | 47.092 | 37.058 | 19.190 1.00 18.29 |
| ATOM | 641 | C | ILE | 888 | 45.392 | 38.822 | 14.663 1.00 19.51 |
| ATOM | 642 | O | ILE | 888 | 45.834 | 38.710 | 13.529 1.00 19.15 |
| ATOM | 643 | N | LEU | 889 | 44.088 | 38.828 | 14.922 1.00 15.54 |
| ATOM | 645 | CA | LEU | 889 | 43.078 | 38.677 | 13.872 1.00 20.73 |
| ATOM | 646 | CB | LEU | 889 | 41.658 | 38.818 | 14.446 1.00 19.41 |
| ATOM | 647 | CG | LEU | 889 | 41.204 | 37.652 | 15.372 1.00 22.61 |
| ATOM | 648 | CD1 | LEU | 889 | 39.735 | 37.752 | 15.697 1.00 13.49 |
| ATOM | 649 | CD2 | LEU | 889 | 41.500 | 36.263 | 14.764 1.00 18.87 |
| ATOM | 650 | C | LEU | 889 | 43.308 | 39.678 | 12.762 1.00 24.12 |
| ATOM | 651 | O | LEU | 889 | 43.342 | 39.344 | 11.584 1.00 28.65 |
| ATOM | 652 | N | ILE | 890 | 43.461 | 40.931 | 13.138 1.00 29.62 |
| ATOM | 654 | CA | ILE | 890 | 43.753 | 41.953 | 12.158 1.00 26.41 |
| ATOM | 655 | CB | ILE | 890 | 43.966 | 43.310 | 12.865 1.00 24.45 |
| ATOM | 656 | CG2 | ILE | 890 | 44.555 | 44.333 | 11.888 1.00 30.36 |
| ATOM | 657 | CG1 | ILE | 890 | 42.645 | 43.825 | 13.438 1.00 19.80 |
| ATOM | 658 | CD1 | ILE | 890 | 42.812 | 45.061 | 14.241 1.00 14.93 |
| ATOM | 659 | C | ILE | 890 | 45.053 | 41.519 | 11.415 1.00 28.37 |
| ATOM | 660 | O | ILE | 890 | 45.126 | 41.553 | 10.191 1.00 24.83 |
| ATOM | 661 | N | HIS | 891 | 46.066 | 41.099 | 12.164 1.00 27.37 |
| ATOM | 663 | CA | HIS | 891 | 47.309 | 40.659 | 11.567 1.00 27.76 |
| ATOM | 664 | CB | HIS | 891 | 48.277 | 40.175 | 12.654 1.00 36.80 |
| ATOM | 665 | CG | HIS | 891 | 49.509 | 39.507 | 12.100 1.00 47.58 |
| ATOM | 666 | CD2 | HIS | 891 | 50.811 | 39.869 | 12.147 1.00 46.38 |
| ATOM | 667 | ND1 | HIS | 891 | 49.450 | 38.394 | 11.276 1.00 52.71 |
| ATOM | 669 | CE1 | HIS | 891 | 50.660 | 38.114 | 10.825 1.00 50.46 |
| ATOM | 670 | NE2 | HIS | 891 | 51.505 | 38.993 | 11.340 1.00 54.62 |
| ATOM | 672 | C | HIS | 891 | 47.098 | 39.536 | 10.537 1.00 27.01 |
| ATOM | 673 | O | HIS | 891 | 47.522 | 39.647 | 9.402 1.00 32.82 |
| ATOM | 674 | N | ILE | 892 | 46.580 | 38.403 | 10.995 1.00 24.99 |
| ATOM | 676 | CA | ILE | 892 | 46.300 | 37.216 | 10.181 1.00 23.19 |
| ATOM | 677 | CB | ILE | 892 | 45.233 | 36.282 | 10.907 1.00 24.73 |
| ATOM | 678 | CG2 | ILE | 892 | 44.643 | 35.295 | 9.941 1.00 20.03 |
| ATOM | 679 | CG1 | ILE | 892 | 45.828 | 35.522 | 12.104 1.00 26.32 |
| ATOM | 680 | CD1 | ILE | 892 | 47.015 | 36.222 | 12.787 1.00 36.72 |
| ATOM | 681 | C | ILE | 892 | 45.700 | 37.625 | 8.848 1.00 22.57 |
| ATOM | 682 | O | ILE | 892 | 46.115 | 37.155 | 7.775 1.00 25.20 |

FIG. 7(14)

| ATOM | 683 | N | GLY | 893 | 44.699 | 38.492 | 8.916 | 1.00 | 23.88 |
|---|---|---|---|---|---|---|---|---|---|
| ATOM | 685 | CA | GLY | 893 | 44.034 | 38.910 | 7.702 | 1.00 | 25.37 |
| ATOM | 686 | C | GLY | 893 | 42.794 | 38.080 | 7.403 | 1.00 | 25.54 |
| ATOM | 687 | O | GLY | 893 | 42.303 | 37.326 | 8.224 | 1.00 | 32.60 |
| ATOM | 688 | N | HIS | 894 | 42.327 | 38.149 | 6.176 | 1.00 | 26.97 |
| ATOM | 690 | CA | HIS | 894 | 41.120 | 37.457 | 5.797 | 1.00 | 26.35 |
| ATOM | 691 | CB | HIS | 894 | 40.233 | 38.464 | 5.042 | 1.00 | 31.72 |
| ATOM | 692 | CG | HIS | 894 | 39.114 | 37.833 | 4.274 | 1.00 | 35.68 |
| ATOM | 693 | CD2 | HIS | 894 | 37.818 | 37.609 | 4.608 | 1.00 | 34.18 |
| ATOM | 694 | ND1 | HIS | 894 | 39.271 | 37.346 | 2.989 | 1.00 | 38.36 |
| ATOM | 696 | CE1 | HIS | 894 | 38.121 | 36.854 | 2.568 | 1.00 | 36.24 |
| ATOM | 697 | NE2 | HIS | 894 | 37.224 | 37.004 | 3.527 | 1.00 | 35.86 |
| ATOM | 699 | C | HIS | 894 | 41.253 | 36.182 | 4.958 | 1.00 | 24.38 |
| ATOM | 700 | O | HIS | 894 | 42.045 | 36.108 | 4.007 | 1.00 | 24.24 |
| ATOM | 701 | N | HIS | 895 | 40.426 | 35.202 | 5.280 | 1.00 | 17.00 |
| ATOM | 703 | CA | HIS | 895 | 40.379 | 33.994 | 4.494 | 1.00 | 18.62 |
| ATOM | 704 | CB | HIS | 895 | 41.363 | 32.929 | 4.931 | 1.00 | 15.85 |
| ATOM | 705 | CG | HIS | 895 | 41.446 | 31.814 | 3.943 | 1.00 | 21.47 |
| ATOM | 706 | CD2 | HIS | 895 | 42.076 | 31.737 | 2.745 | 1.00 | 17.93 |
| ATOM | 707 | ND1 | HIS | 895 | 40.675 | 30.676 | 4.042 | 1.00 | 21.96 |
| ATOM | 709 | CE1 | HIS | 895 | 40.819 | 29.956 | 2.938 | 1.00 | 21.22 |
| ATOM | 710 | NE2 | HIS | 895 | 41.663 | 30.578 | 2.137 | 1.00 | 10.16 |
| ATOM | 712 | C | HIS | 895 | 38.979 | 33.467 | 4.626 | 1.00 | 15.66 |
| ATOM | 713 | O | HIS | 895 | 38.396 | 33.656 | 5.663 | 1.00 | 18.76 |
| ATOM | 714 | N | LEU | 896 | 38.419 | 32.865 | 3.567 | 1.00 | 21.74 |
| ATOM | 716 | CA | LEU | 896 | 37.042 | 32.306 | 3.584 | 1.00 | 18.37 |
| ATOM | 717 | CB | LEU | 896 | 36.652 | 31.762 | 2.210 | 1.00 | 17.64 |
| ATOM | 718 | CG | LEU | 896 | 35.297 | 31.068 | 2.218 | 1.00 | 25.15 |
| ATOM | 719 | CD1 | LEU | 896 | 34.218 | 32.077 | 2.454 | 1.00 | 24.41 |
| ATOM | 720 | CD2 | LEU | 896 | 35.042 | 30.342 | 0.934 | 1.00 | 25.59 |
| ATOM | 721 | C | LEU | 896 | 36.867 | 31.172 | 4.569 | 1.00 | 17.58 |
| ATOM | 722 | O | LEU | 896 | 35.783 | 30.937 | 5.068 | 1.00 | 23.11 |
| ATOM | 723 | N | ASN | 897 | 37.952 | 30.475 | 4.849 | 1.00 | 15.99 |
| ATOM | 725 | CA | ASN | 897 | 37.878 | 29.340 | 5.725 | 1.00 | 18.36 |
| ATOM | 726 | CB | ASN | 897 | 38.589 | 28.134 | 5.078 | 1.00 | 20.86 |
| ATOM | 727 | CG | ASN | 897 | 37.928 | 27.689 | 3.747 | 1.00 | 16.88 |
| ATOM | 728 | OD1 | ASN | 897 | 38.567 | 27.692 | 2.694 | 1.00 | 14.51 |
| ATOM | 729 | ND2 | ASN | 897 | 36.639 | 27.346 | 3.799 | 1.00 | 12.11 |
| ATOM | 732 | C | ASN | 897 | 38.293 | 29.541 | 7.188 | 1.00 | 25.65 |
| ATOM | 733 | O | ASN | 897 | 38.648 | 28.556 | 7.858 | 1.00 | 22.22 |
| ATOM | 734 | N | VAL | 898 | 38.357 | 30.800 | 7.660 | 1.00 | 23.53 |
| ATOM | 736 | CA | VAL | 898 | 38.631 | 31.079 | 9.081 | 1.00 | 15.38 |
| ATOM | 737 | CB | VAL | 898 | 40.036 | 31.719 | 9.457 | 1.00 | 11.47 |

FIG. 7(15)

| | | | | | | | | |
|---|---|---|---|---|---|---|---|---|
| ATOM | 738 | CG1 | VAL | 898 | 41.146 | 30.813 | 9.017 | 1.00 14.76 |
| ATOM | 739 | CG2 | VAL | 898 | 40.236 | 33.119 | 8.883 | 1.00 8.71 |
| ATOM | 740 | C | VAL | 898 | 37.475 | 31.959 | 9.477 | 1.00 15.57 |
| ATOM | 741 | O | VAL | 898 | 36.698 | 32.382 | 8.620 | 1.00 17.87 |
| ATOM | 742 | N | VAL | 899 | 37.226 | 32.049 | 10.773 | 1.00 18.55 |
| ATOM | 744 | CA | VAL | 899 | 36.155 | 32.882 | 11.264 | 1.00 20.68 |
| ATOM | 745 | CB | VAL | 899 | 35.757 | 32.487 | 12.720 | 1.00 19.98 |
| ATOM | 746 | CG1 | VAL | 899 | 34.618 | 33.384 | 13.202 | 1.00 18.29 |
| ATOM | 747 | CG2 | VAL | 899 | 35.346 | 31.016 | 12.788 | 1.00 12.67 |
| ATOM | 748 | C | VAL | 899 | 36.807 | 34.272 | 11.244 | 1.00 21.95 |
| ATOM | 749 | O | VAL | 899 | 37.725 | 34.517 | 12.003 | 1.00 21.42 |
| ATOM | 750 | N | ASN | 900 | 36.352 | 35.164 | 10.363 | 1.00 23.43 |
| ATOM | 752 | CA | ASN | 900 | 36.930 | 36.526 | 10.226 | 1.00 23.52 |
| ATOM | 753 | CB | ASN | 900 | 36.737 | 37.061 | 8.803 | 1.00 19.45 |
| ATOM | 754 | CG | ASN | 900 | 37.350 | 36.177 | 7.782 | 1.00 19.58 |
| ATOM | 755 | OD1 | ASN | 900 | 38.578 | 36.087 | 7.667 | 1.00 17.65 |
| ATOM | 756 | ND2 | ASN | 900 | 36.511 | 35.528 | 7.004 | 1.00 20.34 |
| ATOM | 759 | C | ASN | 900 | 36.484 | 37.641 | 11.152 | 1.00 17.00 |
| ATOM | 760 | O | ASN | 900 | 35.343 | 37.704 | 11.598 | 1.00 16.94 |
| ATOM | 761 | N | LEU | 901 | 37.413 | 38.544 | 11.384 | 1.00 17.25 |
| ATOM | 763 | CA | LEU | 901 | 37.167 | 39.733 | 12.160 | 1.00 17.98 |
| ATOM | 764 | CB | LEU | 901 | 38.494 | 40.447 | 12.426 | 1.00 16.80 |
| ATOM | 765 | CG | LEU | 901 | 38.444 | 41.819 | 13.101 | 1.00 14.17 |
| ATOM | 766 | CD1 | LEU | 901 | 38.018 | 41.673 | 14.560 | 1.00 11.71 |
| ATOM | 767 | CD2 | LEU | 901 | 39.782 | 42.435 | 13.008 | 1.00 2.76 |
| ATOM | 768 | C | LEU | 901 | 36.354 | 40.578 | 11.174 | 1.00 20.28 |
| ATOM | 769 | O | LEU | 901 | 36.669 | 40.612 | 9.965 | 1.00 18.06 |
| ATOM | 770 | N | LEU | 902 | 35.280 | 41.180 | 11.686 | 1.00 19.74 |
| ATOM | 772 | CA | LEU | 902 | 34.398 | 42.031 | 10.917 | 1.00 15.84 |
| ATOM | 773 | CB | LEU | 902 | 32.950 | 41.593 | 11.087 | 1.00 11.70 |
| ATOM | 774 | CG | LEU | 902 | 32.615 | 40.230 | 10.473 | 1.00 13.49 |
| ATOM | 775 | CD1 | LEU | 902 | 31.142 | 39.827 | 10.774 | 1.00 13.78 |
| ATOM | 776 | CD2 | LEU | 902 | 32.856 | 40.270 | 8.981 | 1.00 12.15 |
| ATOM | 777 | C | LEU | 902 | 34.566 | 43.486 | 11.345 | 1.00 19.59 |
| ATOM | 778 | O | LEU | 902 | 34.466 | 44.380 | 10.510 | 1.00 23.95 |
| ATOM | 779 | N | GLY | 903 | 34.854 | 43.724 | 12.625 | 1.00 20.15 |
| ATOM | 781 | CA | GLY | 903 | 35.037 | 45.090 | 13.114 | 1.00 21.60 |
| ATOM | 782 | C | GLY | 903 | 35.147 | 45.075 | 14.620 | 1.00 24.02 |
| ATOM | 783 | O | GLY | 903 | 35.070 | 43.991 | 15.194 | 1.00 26.53 |
| ATOM | 784 | N | ALA | 904 | 35.305 | 46.236 | 15.269 | 1.00 25.19 |
| ATOM | 786 | CA | ALA | 904 | 35.411 | 46.293 | 16.740 | 1.00 18.80 |
| ATOM | 787 | CB | ALA | 904 | 36.830 | 46.074 | 17.177 | 1.00 12.62 |
| ATOM | 788 | C | ALA | 904 | 34.886 | 47.559 | 17.386 | 1.00 20.83 |

FIG. 7(16)

| ATOM | 789 | O   | ALA | 904 | 34.789 | 48.616 | 16.765 | 1.00 | 26.12 |
|------|-----|-----|-----|-----|--------|--------|--------|------|-------|
| ATOM | 790 | N   | CYS | 905 | 34.617 | 47.443 | 18.674 | 1.00 | 21.21 |
| ATOM | 792 | CA  | CYS | 905 | 34.128 | 48.530 | 19.493 | 1.00 | 19.91 |
| ATOM | 793 | CB  | CYS | 905 | 32.804 | 48.160 | 20.115 | 1.00 | 16.08 |
| ATOM | 794 | SG  | CYS | 905 | 31.561 | 47.894 | 18.851 | 1.00 | 15.32 |
| ATOM | 795 | C   | CYS | 905 | 35.176 | 48.687 | 20.556 | 1.00 | 23.00 |
| ATOM | 796 | O   | CYS | 905 | 35.245 | 47.890 | 21.486 | 1.00 | 24.21 |
| ATOM | 797 | N   | THR | 906 | 36.042 | 49.674 | 20.361 | 1.00 | 26.02 |
| ATOM | 799 | CA  | THR | 906 | 37.140 | 49.945 | 21.283 | 1.00 | 29.46 |
| ATOM | 800 | CB  | THR | 906 | 38.514 | 49.768 | 20.574 | 1.00 | 26.67 |
| ATOM | 801 | OG1 | THR | 906 | 38.635 | 50.739 | 19.526 | 1.00 | 29.06 |
| ATOM | 803 | CG2 | THR | 906 | 38.648 | 48.363 | 20.001 | 1.00 | 23.13 |
| ATOM | 804 | C   | THR | 906 | 37.130 | 51.346 | 21.928 | 1.00 | 30.07 |
| ATOM | 805 | O   | THR | 906 | 37.642 | 51.522 | 23.036 | 1.00 | 29.29 |
| ATOM | 806 | N   | LYS | 907 | 36.582 | 52.332 | 21.228 | 1.00 | 32.81 |
| ATOM | 808 | CA  | LYS | 907 | 36.554 | 53.686 | 21.745 | 1.00 | 39.38 |
| ATOM | 809 | CB  | LYS | 907 | 35.982 | 54.637 | 20.701 | 1.00 | 41.03 |
| ATOM | 810 | CG  | LYS | 907 | 34.536 | 54.432 | 20.386 | 1.00 | 48.86 |
| ATOM | 811 | CD  | LYS | 907 | 34.071 | 55.528 | 19.427 | 1.00 | 57.25 |
| ATOM | 812 | CE  | LYS | 907 | 33.996 | 56.878 | 20.143 | 1.00 | 63.62 |
| ATOM | 813 | NZ  | LYS | 907 | 33.688 | 58.001 | 19.213 | 1.00 | 68.81 |
| ATOM | 817 | C   | LYS | 907 | 35.796 | 53.779 | 23.070 | 1.00 | 44.43 |
| ATOM | 818 | O   | LYS | 907 | 35.094 | 52.867 | 23.442 | 1.00 | 44.52 |
| ATOM | 819 | N   | PRO | 908 | 36.034 | 54.838 | 23.857 | 1.00 | 49.18 |
| ATOM | 820 | CD  | PRO | 908 | 37.147 | 55.794 | 23.712 | 1.00 | 50.93 |
| ATOM | 821 | CA  | PRO | 908 | 35.358 | 55.022 | 25.149 | 1.00 | 46.86 |
| ATOM | 822 | CB  | PRO | 908 | 35.963 | 56.324 | 25.647 | 1.00 | 49.68 |
| ATOM | 823 | CG  | PRO | 908 | 37.387 | 56.216 | 25.143 | 1.00 | 51.43 |
| ATOM | 824 | C   | PRO | 908 | 33.852 | 55.145 | 25.036 | 1.00 | 44.06 |
| ATOM | 825 | O   | PRO | 908 | 33.345 | 55.600 | 24.008 | 1.00 | 44.40 |
| ATOM | 826 | N   | GLY | 909 | 33.154 | 54.772 | 26.110 | 1.00 | 41.44 |
| ATOM | 828 | CA  | GLY | 909 | 31.698 | 54.842 | 26.135 | 1.00 | 37.38 |
| ATOM | 829 | C   | GLY | 909 | 30.999 | 53.502 | 26.035 | 1.00 | 38.26 |
| ATOM | 830 | O   | GLY | 909 | 29.778 | 53.439 | 25.751 | 1.00 | 40.07 |
| ATOM | 831 | N   | GLY | 910 | 31.753 | 52.424 | 26.264 | 1.00 | 36.39 |
| ATOM | 833 | CA  | GLY | 910 | 31.178 | 51.087 | 26.190 | 1.00 | 34.35 |
| ATOM | 834 | C   | GLY | 910 | 32.180 | 49.961 | 26.360 | 1.00 | 31.85 |
| ATOM | 835 | O   | GLY | 910 | 33.394 | 50.235 | 26.528 | 1.00 | 27.95 |
| ATOM | 836 | N   | PRO | 911 | 31.710 | 48.686 | 26.319 | 1.00 | 27.95 |
| ATOM | 837 | CD  | PRO | 911 | 30.280 | 48.339 | 26.197 | 1.00 | 28.51 |
| ATOM | 838 | CA  | PRO | 911 | 32.511 | 47.463 | 26.467 | 1.00 | 25.21 |
| ATOM | 839 | CB  | PRO | 911 | 31.438 | 46.393 | 26.724 | 1.00 | 27.44 |
| ATOM | 840 | CG  | PRO | 911 | 30.315 | 46.840 | 25.891 | 1.00 | 22.45 |

FIG. 7(17)

| | | | | | | | | |
|---|---|---|---|---|---|---|---|---|
| ATOM | 841 | C | PRO | 911 | 33.340 | 47.118 | 25.234 | 1.00 22.33 |
| ATOM | 842 | O | PRO | 911 | 32.903 | 47.366 | 24.124 | 1.00 23.57 |
| ATOM | 843 | N | LEU | 912 | 34.548 | 46.581 | 25.430 | 1.00 22.75 |
| ATOM | 845 | CA | LEU | 912 | 35.412 | 46.177 | 24.308 | 1.00 23.22 |
| ATOM | 846 | CB | LEU | 912 | 36.778 | 45.685 | 24.812 | 1.00 23.67 |
| ATOM | 847 | CG | LEU | 912 | 38.095 | 45.759 | 24.005 | 1.00 24.34 |
| ATOM | 848 | CD1 | LEU | 912 | 38.988 | 44.618 | 24.490 | 1.00 20.11 |
| ATOM | 849 | CD2 | LEU | 912 | 37.906 | 45.745 | 22.477 | 1.00 12.72 |
| ATOM | 850 | C | LEU | 912 | 34.692 | 45.010 | 23.627 | 1.00 22.56 |
| ATOM | 851 | O | LEU | 912 | 34.342 | 44.029 | 24.283 | 1.00 17.69 |
| ATOM | 852 | N | MET | 913 | 34.417 | 45.142 | 22.334 | 1.00 24.19 |
| ATOM | 854 | CA | MET | 913 | 33.724 | 44.085 | 21.617 | 1.00 21.51 |
| ATOM | 855 | CB | MET | 913 | 32.264 | 44.456 | 21.429 | 1.00 22.09 |
| ATOM | 856 | CG | MET | 913 | 31.489 | 44.461 | 22.728 | 1.00 22.26 |
| ATOM | 857 | SD | MET | 913 | 29.829 | 45.009 | 22.484 | 1.00 24.17 |
| ATOM | 858 | CE | MET | 913 | 30.127 | 46.676 | 22.205 | 1.00 20.40 |
| ATOM | 859 | C | MET | 913 | 34.386 | 43.768 | 20.295 | 1.00 20.42 |
| ATOM | 860 | O | MET | 913 | 34.701 | 44.657 | 19.519 | 1.00 21.08 |
| ATOM | 861 | N | VAL | 914 | 34.703 | 42.491 | 20.102 | 1.00 23.72 |
| ATOM | 863 | CA | VAL | 914 | 35.354 | 42.001 | 18.891 | 1.00 20.24 |
| ATOM | 864 | CB | VAL | 914 | 36.614 | 41.170 | 19.232 | 1.00 16.92 |
| ATOM | 865 | CG1 | VAL | 914 | 37.254 | 40.637 | 17.958 | 1.00 19.36 |
| ATOM | 866 | CG2 | VAL | 914 | 37.629 | 42.055 | 19.972 | 1.00 13.30 |
| ATOM | 867 | C | VAL | 914 | 34.296 | 41.210 | 18.132 | 1.00 19.70 |
| ATOM | 868 | O | VAL | 914 | 33.836 | 40.191 | 18.587 | 1.00 26.45 |
| ATOM | 869 | N | ILE | 915 | 33.844 | 41.775 | 17.026 | 1.00 19.86 |
| ATOM | 871 | CA | ILE | 915 | 32.806 | 41.212 | 16.179 | 1.00 20.42 |
| ATOM | 872 | CB | ILE | 915 | 32.034 | 42.384 | 15.455 | 1.00 18.44 |
| ATOM | 873 | CG2 | ILE | 915 | 30.721 | 41.909 | 14.869 | 1.00 12.35 |
| ATOM | 874 | CG1 | ILE | 915 | 31.756 | 43.531 | 16.426 | 1.00 17.60 |
| ATOM | 875 | CD1 | ILE | 915 | 31.358 | 44.822 | 15.735 | 1.00 15.14 |
| ATOM | 876 | C | ILE | 915 | 33.457 | 40.287 | 15.115 | 1.00 23.98 |
| ATOM | 877 | O | ILE | 915 | 34.361 | 40.722 | 14.373 | 1.00 23.30 |
| ATOM | 878 | N | VAL | 916 | 33.054 | 39.011 | 15.075 | 1.00 20.08 |
| ATOM | 880 | CA | VAL | 916 | 33.594 | 38.089 | 14.077 | 1.00 17.64 |
| ATOM | 881 | CB | VAL | 916 | 34.543 | 37.003 | 14.680 | 1.00 9.09 |
| ATOM | 882 | CG1 | VAL | 916 | 35.703 | 37.685 | 15.350 | 1.00 5.05 |
| ATOM | 883 | CG2 | VAL | 916 | 33.817 | 36.126 | 15.678 | 1.00 10.26 |
| ATOM | 884 | C | VAL | 916 | 32.422 | 37.486 | 13.342 | 1.00 17.74 |
| ATOM | 885 | O | VAL | 916 | 31.275 | 37.790 | 13.664 | 1.00 20.02 |
| ATOM | 886 | N | GLU | 917 | 32.684 | 36.702 | 12.303 | 1.00 14.74 |
| ATOM | 888 | CA | GLU | 917 | 31.589 | 36.073 | 11.577 | 1.00 13.03 |
| ATOM | 889 | CB | GLU | 917 | 32.120 | 35.409 | 10.332 | 1.00 14.06 |

FIG. 7(18)

| ATOM | 890 | CG  | GLU | 917 | 32.946 | 36.348 | 9.464  | 1.00 | 24.11 |
|------|-----|-----|-----|-----|--------|--------|--------|------|-------|
| ATOM | 891 | CD  | GLU | 917 | 33.543 | 35.651 | 8.258  | 1.00 | 26.52 |
| ATOM | 892 | OE1 | GLU | 917 | 33.060 | 35.904 | 7.139  | 1.00 | 27.67 |
| ATOM | 893 | OE2 | GLU | 917 | 34.480 | 34.841 | 8.425  | 1.00 | 28.39 |
| ATOM | 894 | C   | GLU | 917 | 30.853 | 35.051 | 12.434 | 1.00 | 14.78 |
| ATOM | 895 | O   | GLU | 917 | 31.445 | 34.344 | 13.234 | 1.00 | 14.35 |
| ATOM | 896 | N   | PHE | 918 | 29.557 | 34.958 | 12.229 | 1.00 | 19.12 |
| ATOM | 898 | CA  | PHE | 918 | 28.688 | 34.042 | 12.966 | 1.00 | 18.07 |
| ATOM | 899 | CB  | PHE | 918 | 27.334 | 34.721 | 13.168 | 1.00 | 18.48 |
| ATOM | 900 | CG  | PHE | 918 | 26.275 | 33.840 | 13.748 | 1.00 | 17.83 |
| ATOM | 901 | CD1 | PHE | 918 | 26.328 | 33.456 | 15.081 | 1.00 | 18.65 |
| ATOM | 902 | CD2 | PHE | 918 | 25.213 | 33.400 | 12.953 | 1.00 | 21.10 |
| ATOM | 903 | CE1 | PHE | 918 | 25.336 | 32.639 | 15.613 | 1.00 | 18.12 |
| ATOM | 904 | CE2 | PHE | 918 | 24.210 | 32.580 | 13.473 | 1.00 | 14.29 |
| ATOM | 905 | CZ  | PHE | 918 | 24.274 | 32.201 | 14.799 | 1.00 | 17.78 |
| ATOM | 906 | C   | PHE | 918 | 28.487 | 32.805 | 12.113 | 1.00 | 18.83 |
| ATOM | 907 | O   | PHE | 918 | 28.081 | 32.917 | 10.964 | 1.00 | 11.61 |
| ATOM | 908 | N   | CYS | 919 | 28.761 | 31.635 | 12.676 | 1.00 | 19.49 |
| ATOM | 910 | CA  | CYS | 919 | 28.590 | 30.372 | 11.947 | 1.00 | 19.00 |
| ATOM | 911 | CB  | CYS | 919 | 29.855 | 29.566 | 12.069 | 1.00 | 16.78 |
| ATOM | 912 | SG  | CYS | 919 | 31.225 | 30.428 | 11.325 | 1.00 | 16.84 |
| ATOM | 913 | C   | CYS | 919 | 27.383 | 29.659 | 12.556 | 1.00 | 21.18 |
| ATOM | 914 | O   | CYS | 919 | 27.474 | 29.135 | 13.676 | 1.00 | 20.69 |
| ATOM | 915 | N   | LYS | 920 | 26.269 | 29.653 | 11.818 | 1.00 | 18.06 |
| ATOM | 917 | CA  | LYS | 920 | 24.998 | 29.130 | 12.318 | 1.00 | 28.13 |
| ATOM | 918 | CB  | LYS | 920 | 23.799 | 29.581 | 11.459 | 1.00 | 25.17 |
| ATOM | 919 | CG  | LYS | 920 | 23.595 | 28.799 | 10.207 | 1.00 | 33.78 |
| ATOM | 920 | CD  | LYS | 920 | 22.658 | 29.509 | 9.250  | 1.00 | 40.32 |
| ATOM | 921 | CE  | LYS | 920 | 21.261 | 29.706 | 9.829  | 1.00 | 51.94 |
| ATOM | 922 | NZ  | LYS | 920 | 20.343 | 30.396 | 8.845  | 1.00 | 56.09 |
| ATOM | 926 | C   | LYS | 920 | 24.813 | 27.679 | 12.700 | 1.00 | 28.53 |
| ATOM | 927 | O   | LYS | 920 | 24.020 | 27.405 | 13.592 | 1.00 | 31.57 |
| ATOM | 928 | N   | PHE | 921 | 25.533 | 26.757 | 12.078 | 1.00 | 24.89 |
| ATOM | 930 | CA  | PHE | 921 | 25.328 | 25.362 | 12.409 | 1.00 | 21.12 |
| ATOM | 931 | CB  | PHE | 921 | 25.497 | 24.518 | 11.171 | 1.00 | 20.75 |
| ATOM | 932 | CG  | PHE | 921 | 24.588 | 24.917 | 10.084 | 1.00 | 22.95 |
| ATOM | 933 | CD1 | PHE | 921 | 23.224 | 24.734 | 10.219 | 1.00 | 27.55 |
| ATOM | 934 | CD2 | PHE | 921 | 25.077 | 25.564 | 8.975  | 1.00 | 29.40 |
| ATOM | 935 | CE1 | PHE | 921 | 22.362 | 25.205 | 9.269  | 1.00 | 35.42 |
| ATOM | 936 | CE2 | PHE | 921 | 24.237 | 26.041 | 8.013  | 1.00 | 32.24 |
| ATOM | 937 | CZ  | PHE | 921 | 22.869 | 25.870 | 8.154  | 1.00 | 38.81 |
| ATOM | 938 | C   | PHE | 921 | 26.158 | 24.823 | 13.535 | 1.00 | 21.23 |
| ATOM | 939 | O   | PHE | 921 | 26.002 | 23.664 | 13.900 | 1.00 | 22.74 |

FIG. 7(19)

| | | | | | | | | |
|---|---|---|---|---|---|---|---|---|
| ATOM | 940 | N | GLY | 922 | 27.047 | 25.659 | 14.065 | 1.00 18.39 |
| ATOM | 942 | CA | GLY | 922 | 27.906 | 25.257 | 15.172 | 1.00 17.62 |
| ATOM | 943 | C | GLY | 922 | 29.115 | 24.455 | 14.759 | 1.00 18.42 |
| ATOM | 944 | O | GLY | 922 | 29.331 | 24.230 | 13.581 | 1.00 20.81 |
| ATOM | 945 | N | ASN | 923 | 29.903 | 24.011 | 15.729 | 1.00 22.93 |
| ATOM | 947 | CA | ASN | 923 | 31.092 | 23.223 | 15.430 | 1.00 24.85 |
| ATOM | 948 | CB | ASN | 923 | 31.867 | 22.837 | 16.705 | 1.00 29.68 |
| ATOM | 949 | CG | ASN | 923 | 31.212 | 21.710 | 17.493 | 1.00 39.14 |
| ATOM | 950 | OD1 | ASN | 923 | 31.252 | 20.550 | 17.087 | 1.00 41.11 |
| ATOM | 951 | ND2 | ASN | 923 | 30.662 | 22.038 | 18.660 | 1.00 35.87 |
| ATOM | 954 | C | ASN | 923 | 30.818 | 22.019 | 14.523 | 1.00 21.09 |
| ATOM | 955 | O | ASN | 923 | 29.685 | 21.566 | 14.370 | 1.00 20.59 |
| ATOM | 956 | N | LEU | 924 | 31.867 | 21.523 | 13.896 | 1.00 21.13 |
| ATOM | 958 | CA | LEU | 924 | 31.740 | 20.431 | 12.957 | 1.00 22.85 |
| ATOM | 959 | CB | LEU | 924 | 33.019 | 20.377 | 12.126 | 1.00 23.67 |
| ATOM | 960 | CG | LEU | 924 | 33.019 | 19.462 | 10.920 | 1.00 17.22 |
| ATOM | 961 | CD1 | LEU | 924 | 31.776 | 19.699 | 10.125 | 1.00 18.21 |
| ATOM | 962 | CD2 | LEU | 924 | 34.268 | 19.729 | 10.095 | 1.00 23.82 |
| ATOM | 963 | C | LEU | 924 | 31.414 | 19.062 | 13.558 | 1.00 22.65 |
| ATOM | 964 | O | LEU | 924 | 30.601 | 18.326 | 13.013 | 1.00 26.13 |
| ATOM | 965 | N | SER | 925 | 31.035 | 18.742 | 14.687 | 1.00 20.06 |
| ATOM | 967 | CA | SER | 925 | 31.853 | 17.463 | 15.383 | 1.00 25.99 |
| ATOM | 968 | CB | SER | 925 | 32.741 | 17.400 | 16.623 | 1.00 27.28 |
| ATOM | 969 | OG | SER | 925 | 32.426 | 16.272 | 17.416 | 1.00 32.86 |
| ATOM | 971 | C | SER | 925 | 30.432 | 17.217 | 15.812 | 1.00 26.73 |
| ATOM | 972 | O | SER | 925 | 29.863 | 16.148 | 15.552 | 1.00 30.93 |
| ATOM | 973 | N | THR | 926 | 29.892 | 18.190 | 16.534 | 1.00 24.48 |
| ATOM | 975 | CA | THR | 926 | 28.535 | 18.129 | 16.996 | 1.00 19.27 |
| ATOM | 976 | CB | THR | 926 | 28.258 | 19.336 | 17.901 | 1.00 16.05 |
| ATOM | 977 | OG1 | THR | 926 | 29.230 | 19.374 | 18.951 | 1.00 18.42 |
| ATOM | 979 | CG2 | THR | 926 | 26.927 | 19.216 | 18.550 | 1.00 13.93 |
| ATOM | 980 | C | THR | 926 | 27.610 | 18.048 | 15.758 | 1.00 20.47 |
| ATOM | 981 | O | THR | 926 | 26.654 | 17.258 | 15.711 | 1.00 25.12 |
| ATOM | 982 | N | TYR | 927 | 27.961 | 18.760 | 14.701 | 1.00 18.97 |
| ATOM | 984 | CA | TYR | 927 | 27.128 | 18.715 | 13.515 | 1.00 20.97 |
| ATOM | 985 | CB | TYR | 927 | 27.597 | 19.720 | 12.464 | 1.00 18.52 |
| ATOM | 986 | CG | TYR | 927 | 26.708 | 19.683 | 11.230 | 1.00 18.69 |
| ATOM | 987 | CD1 | TYR | 927 | 25.391 | 20.196 | 11.266 | 1.00 14.64 |
| ATOM | 988 | CE1 | TYR | 927 | 24.567 | 20.173 | 10.125 | 1.00 13.73 |
| ATOM | 989 | CD2 | TYR | 927 | 27.173 | 19.138 | 10.031 | 1.00 22.28 |
| ATOM | 990 | CE2 | TYR | 927 | 26.347 | 19.104 | 8.879 | 1.00 24.92 |
| ATOM | 991 | CZ | TYR | 927 | 25.058 | 19.626 | 8.944 | 1.00 16.40 |
| ATOM | 992 | OH | TYR | 927 | 24.285 | 19.600 | 7.819 | 1.00 23.87 |

FIG. 7(20)

| ATOM | 994 | C | TYR | 927 | 27.118 | 17.343 | 12.855 | 1.00 | 23.85 |
|---|---|---|---|---|---|---|---|---|---|
| ATOM | 995 | O | TYR | 927 | 26.078 | 16.860 | 12.428 | 1.00 | 24.11 |
| ATOM | 996 | N | LEU | 928 | 28.313 | 16.793 | 12.665 | 1.00 | 28.91 |
| ATOM | 998 | CA | LEU | 928 | 28.513 | 15.495 | 12.020 | 1.00 | 31.09 |
| ATOM | 999 | CB | LEU | 928 | 30.017 | 15.192 | 11.863 | 1.00 | 27.50 |
| ATOM | 1000 | CG | LEU | 928 | 30.813 | 16.159 | 10.953 | 1.00 | 24.21 |
| ATOM | 1001 | CD1 | LEU | 928 | 32.302 | 15.880 | 11.065 | 1.00 | 24.38 |
| ATOM | 1002 | CD2 | LEU | 928 | 30.343 | 16.097 | 9.514 | 1.00 | 12.63 |
| ATOM | 1003 | C | LEU | 928 | 27.801 | 14.369 | 12.747 | 1.00 | 31.00 |
| ATOM | 1004 | O | LEU | 928 | 27.164 | 13.540 | 12.117 | 1.00 | 31.53 |
| ATOM | 1005 | N | ARG | 929 | 27.883 | 14.351 | 14.067 | 1.00 | 34.05 |
| ATOM | 1007 | CA | ARG | 929 | 27.193 | 13.316 | 14.833 | 1.00 | 40.50 |
| ATOM | 1008 | CB | ARG | 929 | 27.406 | 13.552 | 16.325 | 1.00 | 41.71 |
| ATOM | 1009 | CG | ARG | 929 | 28.358 | 12.605 | 16.969 | 1.00 | 40.42 |
| ATOM | 1010 | CD | ARG | 929 | 29.253 | 13.359 | 17.908 | 1.00 | 49.36 |
| ATOM | 1011 | NE | ARG | 929 | 28.521 | 13.947 | 19.020 | 1.00 | 62.28 |
| ATOM | 1013 | CZ | ARG | 929 | 28.946 | 14.985 | 19.749 | 1.00 | 65.86 |
| ATOM | 1014 | NH1 | ARG | 929 | 28.178 | 15.432 | 20.753 | 1.00 | 66.98 |
| ATOM | 1017 | NH2 | ARG | 929 | 30.122 | 15.573 | 19.492 | 1.00 | 58.39 |
| ATOM | 1020 | C | ARG | 929 | 25.678 | 13.304 | 14.529 | 1.00 | 42.76 |
| ATOM | 1021 | O | ARG | 929 | 25.075 | 12.234 | 14.370 | 1.00 | 44.84 |
| ATOM | 1022 | N | SER | 930 | 25.089 | 14.498 | 14.412 | 1.00 | 41.42 |
| ATOM | 1024 | CA | SER | 930 | 23.663 | 14.677 | 14.150 | 1.00 | 37.04 |
| ATOM | 1025 | CB | SER | 930 | 23.324 | 16.151 | 14.250 | 1.00 | 38.80 |
| ATOM | 1026 | OG | SER | 930 | 23.662 | 16.816 | 13.041 | 1.00 | 37.58 |
| ATOM | 1028 | C | SER | 930 | 23.226 | 14.226 | 12.774 | 1.00 | 38.41 |
| ATOM | 1029 | O | SER | 930 | 22.034 | 14.254 | 12.451 | 1.00 | 43.98 |
| ATOM | 1030 | N | LYS | 931 | 24.179 | 13.865 | 11.936 | 1.00 | 37.60 |
| ATOM | 1032 | CA | LYS | 931 | 23.845 | 13.472 | 10.590 | 1.00 | 38.82 |
| ATOM | 1033 | CB | LYS | 931 | 24.575 | 14.387 | 9.606 | 1.00 | 43.10 |
| ATOM | 1034 | CG | LYS | 931 | 24.388 | 15.864 | 9.884 | 1.00 | 45.62 |
| ATOM | 1035 | CD | LYS | 931 | 22.999 | 16.302 | 9.487 | 1.00 | 49.49 |
| ATOM | 1036 | CE | LYS | 931 | 22.901 | 16.444 | 7.985 | 1.00 | 46.94 |
| ATOM | 1037 | NZ | LYS | 931 | 21.501 | 16.690 | 7.568 | 1.00 | 49.54 |
| ATOM | 1041 | C | LYS | 931 | 24.136 | 12.011 | 10.264 | 1.00 | 39.02 |
| ATOM | 1042 | O | LYS | 931 | 23.991 | 11.615 | 9.111 | 1.00 | 42.79 |
| ATOM | 1043 | N | ARG | 932 | 24.522 | 11.199 | 11.247 | 1.00 | 37.44 |
| ATOM | 1045 | CA | ARG | 932 | 24.793 | 9.776 | 10.971 | 1.00 | 38.33 |
| ATOM | 1046 | CB | ARG | 932 | 25.149 | 9.020 | 12.244 | 1.00 | 33.55 |
| ATOM | 1047 | CG | ARG | 932 | 26.456 | 9.461 | 12.798 | 1.00 | 33.92 |
| ATOM | 1048 | CD | ARG | 932 | 26.812 | 8.729 | 14.043 | 1.00 | 35.88 |
| ATOM | 1049 | NE | ARG | 932 | 28.223 | 8.929 | 14.368 | 1.00 | 43.26 |
| ATOM | 1051 | CZ | ARG | 932 | 28.720 | 8.909 | 15.604 | 1.00 | 45.56 |

FIG. 7(21)

| ATOM | 1052 | NH1 ARG | 932 | 30.018 | 9.098 | 15.809 | 1.00 | 47.32 |
|------|------|---------|-----|--------|-------|--------|------|-------|
| ATOM | 1055 | NH2 ARG | 932 | 27.916 | 8.725 | 16.645 | 1.00 | 53.04 |
| ATOM | 1058 | C   ARG | 932 | 23.621 | 9.087 | 10.273 | 1.00 | 41.54 |
| ATOM | 1059 | O   ARG | 932 | 23.821 | 8.135 | 9.532  | 1.00 | 41.31 |
| ATOM | 1060 | N   ASN | 933 | 22.412 | 9.582 | 10.536 | 1.00 | 44.37 |
| ATOM | 1062 | CA  ASN | 933 | 21.181 | 9.069 | 9.956  | 1.00 | 47.14 |
| ATOM | 1063 | CB  ASN | 933 | 19.974 | 9.453 | 10.824 | 1.00 | 54.55 |
| ATOM | 1064 | CG  ASN | 933 | 19.783 | 8.545 | 12.050 | 1.00 | 57.14 |
| ATOM | 1065 | OD1 ASN | 933 | 20.622 | 7.693 | 12.369 | 1.00 | 54.11 |
| ATOM | 1066 | ND2 ASN | 933 | 18.668 | 8.752 | 12.757 | 1.00 | 57.76 |
| ATOM | 1069 | C   ASN | 933 | 20.974 | 9.680 | 8.589  | 1.00 | 49.60 |
| ATOM | 1070 | O   ASN | 933 | 20.260 | 9.125 | 7.753  | 1.00 | 55.62 |
| ATOM | 1071 | N   GLU | 934 | 21.494 | 10.888| 8.403  | 1.00 | 52.11 |
| ATOM | 1073 | CA  GLU | 934 | 21.365 | 11.580| 7.122  | 1.00 | 52.39 |
| ATOM | 1074 | CB  GLU | 934 | 20.859 | 13.007| 7.323  | 1.00 | 56.14 |
| ATOM | 1075 | CG  GLU | 934 | 19.434 | 13.095| 7.822  | 1.00 | 59.40 |
| ATOM | 1076 | CD  GLU | 934 | 19.332 | 13.686| 9.211  | 1.00 | 63.97 |
| ATOM | 1077 | OE1 GLU | 934 | 18.427 | 13.250| 9.953  | 1.00 | 69.17 |
| ATOM | 1078 | OE2 GLU | 934 | 20.138 | 14.580| 9.563  | 1.00 | 64.27 |
| ATOM | 1079 | C   GLU | 934 | 22.677 | 11.593| 6.332  | 1.00 | 50.45 |
| ATOM | 1080 | O   GLU | 934 | 23.188 | 12.663| 5.961  | 1.00 | 50.70 |
| ATOM | 1081 | N   PHE | 935 | 23.205 | 10.396| 6.070  | 1.00 | 46.25 |
| ATOM | 1083 | CA  PHE | 935 | 24.440 | 10.225| 5.325  | 1.00 | 41.20 |
| ATOM | 1084 | CB  PHE | 935 | 25.638 | 10.121| 6.268  | 1.00 | 40.97 |
| ATOM | 1085 | CG  PHE | 935 | 26.923 | 9.800 | 5.555  | 1.00 | 39.81 |
| ATOM | 1086 | CD1 PHE | 935 | 27.327 | 8.478 | 5.378  | 1.00 | 34.65 |
| ATOM | 1087 | CD2 PHE | 935 | 27.676 | 10.815| 4.970  | 1.00 | 33.02 |
| ATOM | 1088 | CE1 PHE | 935 | 28.455 | 8.180 | 4.617  | 1.00 | 32.30 |
| ATOM | 1089 | CE2 PHE | 935 | 28.793 | 10.515| 4.218  | 1.00 | 29.96 |
| ATOM | 1090 | CZ  PHE | 935 | 29.181 | 9.201 | 4.037  | 1.00 | 29.08 |
| ATOM | 1091 | C   PHE | 935 | 24.474 | 9.006 | 4.412  | 1.00 | 40.49 |
| ATOM | 1092 | O   PHE | 935 | 24.394 | 7.871 | 4.865  | 1.00 | 40.47 |
| ATOM | 1093 | N   VAL | 936 | 24.694 | 9.237 | 3.133  | 1.00 | 38.66 |
| ATOM | 1095 | CA  VAL | 936 | 24.809 | 8.138 | 2.208  | 1.00 | 43.29 |
| ATOM | 1096 | CB  VAL | 936 | 23.663 | 8.113 | 1.221  | 1.00 | 40.39 |
| ATOM | 1097 | CG1 VAL | 936 | 23.739 | 9.312 | 0.280  | 1.00 | 34.50 |
| ATOM | 1098 | CG2 VAL | 936 | 23.720 | 6.841 | 0.444  | 1.00 | 42.47 |
| ATOM | 1099 | C   VAL | 936 | 26.087 | 8.436 | 1.438  | 1.00 | 49.63 |
| ATOM | 1100 | O   VAL | 936 | 26.322 | 9.585 | 1.081  | 1.00 | 55.64 |
| ATOM | 1101 | N   PRO | 937 | 26.960 | 7.433 | 1.222  | 1.00 | 50.29 |
| ATOM | 1102 | CD  PRO | 937 | 26.966 | 6.087 | 1.822  | 1.00 | 49.69 |
| ATOM | 1103 | CA  PRO | 937 | 28.207 | 7.669 | 0.483  | 1.00 | 50.65 |
| ATOM | 1104 | CB  PRO | 937 | 28.676 | 6.260 | 0.177  | 1.00 | 46.68 |

FIG. 7(22)

| | | | | | | | |
|---|---|---|---|---|---|---|---|
| ATOM | 1105 | CG | PRO | 937 | 28.378 | 5.582 | 1.493 1.00 47.42 |
| ATOM | 1106 | C | PRO | 937 | 28.019 | 8.501 | -0.774 1.00 53.83 |
| ATOM | 1107 | O | PRO | 937 | 28.644 | 9.558 | -0.937 1.00 53.64 |
| ATOM | 1108 | N | TYR | 938 | 27.153 | 8.046 | -1.660 1.00 54.91 |
| ATOM | 1110 | CA | TYR | 938 | 26.918 | 8.803 | -2.859 1.00 62.52 |
| ATOM | 1111 | CB | TYR | 938 | 27.580 | 8.161 | -4.080 1.00 67.73 |
| ATOM | 1120 | C | TYR | 938 | 25.443 | 8.800 | -3.059 1.00 67.31 |
| ATOM | 1121 | O | TYR | 938 | 24.722 | 8.082 | -2.361 1.00 66.13 |
| ATOM | 1122 | N | LYS | 939 | 25.027 | 9.601 | -4.038 1.00 75.30 |
| ATOM | 1124 | CA | LYS | 939 | 23.639 | 9.770 | -4.445 1.00 81.21 |
| ATOM | 1125 | CB | LYS | 939 | 23.209 | 11.254 | -4.284 1.00 80.04 |
| ATOM | 1126 | C | LYS | 939 | 23.543 | 9.331 | -5.921 1.00 87.24 |
| ATOM | 1127 | O | LYS | 939 | 24.582 | 9.384 | -6.646 1.00 90.23 |
| ATOM | 1129 | CB | ASP | 998 | 17.986 | 15.692 | 3.023 1.00 53.00 |
| ATOM | 1130 | C | ASP | 998 | 20.489 | 15.723 | 3.377 1.00 55.33 |
| ATOM | 1131 | O | ASP | 998 | 21.051 | 16.058 | 4.426 1.00 56.29 |
| ATOM | 1134 | N | ASP | 998 | 19.408 | 16.931 | 1.400 1.00 54.52 |
| ATOM | 1136 | CA | ASP | 998 | 19.279 | 16.514 | 2.829 1.00 55.12 |
| ATOM | 1137 | N | PHE | 999 | 20.900 | 14.687 | 2.653 1.00 52.90 |
| ATOM | 1139 | CA | PHE | 999 | 21.984 | 13.834 | 3.111 1.00 46.86 |
| ATOM | 1140 | CB | PHE | 999 | 21.841 | 12.420 | 2.528 1.00 51.05 |
| ATOM | 1141 | CG | PHE | 999 | 20.897 | 11.537 | 3.296 1.00 55.62 |
| ATOM | 1142 | CD1 | PHE | 999 | 21.249 | 10.236 | 3.606 1.00 56.12 |
| ATOM | 1143 | CD2 | PHE | 999 | 19.671 | 12.022 | 3.751 1.00 60.98 |
| ATOM | 1144 | CE1 | PHE | 999 | 20.397 | 9.422 | 4.368 1.00 61.93 |
| ATOM | 1145 | CE2 | PHE | 999 | 18.816 | 11.222 | 4.509 1.00 61.09 |
| ATOM | 1146 | CZ | PHE | 999 | 19.183 | 9.917 | 4.820 1.00 60.64 |
| ATOM | 1147 | C | PHE | 999 | 23.373 | 14.302 | 2.837 1.00 41.06 |
| ATOM | 1148 | O | PHE | 999 | 23.632 | 14.937 | 1.820 1.00 36.04 |
| ATOM | 1149 | N | LEU | 1000 | 24.238 | 14.057 | 3.812 1.00 37.57 |
| ATOM | 1151 | CA | LEU | 1000 | 25.651 | 14.326 | 3.652 1.00 36.08 |
| ATOM | 1152 | CB | LEU | 1000 | 26.401 | 14.306 | 4.985 1.00 35.67 |
| ATOM | 1153 | CG | LEU | 1000 | 25.923 | 15.286 | 6.057 1.00 36.23 |
| ATOM | 1154 | CD1 | LEU | 1000 | 26.941 | 15.370 | 7.201 1.00 29.94 |
| ATOM | 1155 | CD2 | LEU | 1000 | 25.707 | 16.654 | 5.435 1.00 38.66 |
| ATOM | 1156 | C | LEU | 1000 | 26.089 | 13.139 | 2.756 1.00 35.16 |
| ATOM | 1157 | O | LEU | 1000 | 25.330 | 12.167 | 2.569 1.00 32.68 |
| ATOM | 1158 | N | THR | 1001 | 27.292 | 13.228 | 2.201 1.00 29.92 |
| ATOM | 1160 | CA | THR | 1001 | 27.803 | 12.236 | 1.285 1.00 25.42 |
| ATOM | 1161 | CB | THR | 1001 | 27.396 | 12.560 | -0.178 1.00 30.10 |

FIG. 7(23)

| | | | | | | | |
|---|---|---|---|---|---|---|---|
| ATOM | 1162 | OG1 | THR | 1001 | 28.055 | 13.771 | -0.605 1.00 33.54 |
| ATOM | 1164 | CG2 | THR | 1001 | 25.878 | 12.741 | -0.326 1.00 29.24 |
| ATOM | 1165 | C | THR | 1001 | 29.303 | 12.388 | 1.338 1.00 27.68 |
| ATOM | 1166 | O | THR | 1001 | 29.805 | 13.303 | 1.985 1.00 28.02 |
| ATOM | 1167 | N | LEU | 1002 | 30.020 | 11.552 | 0.592 1.00 26.85 |
| ATOM | 1169 | CA | LEU | 1002 | 31.454 | 11.636 | 0.572 1.00 24.39 |
| ATOM | 1170 | CB | LEU | 1002 | 32.044 | 10.545 | -0.298 1.00 22.71 |
| ATOM | 1171 | CG | LEU | 1002 | 32.269 | 9.304 | 0.573 1.00 27.80 |
| ATOM | 1172 | CD1 | LEU | 1002 | 32.727 | 8.142 | -0.280 1.00 27.11 |
| ATOM | 1173 | CD2 | LEU | 1002 | 33.295 | 9.592 | 1.670 1.00 24.64 |
| ATOM | 1174 | C | LEU | 1002 | 31.908 | 12.995 | 0.099 1.00 26.97 |
| ATOM | 1175 | O | LEU | 1002 | 32.967 | 13.459 | 0.506 1.00 26.84 |
| ATOM | 1176 | N | GLU | 1003 | 31.063 | 13.682 | -0.666 1.00 27.89 |
| ATOM | 1178 | CA | GLU | 1003 | 31.428 | 15.000 | -1.185 1.00 28.02 |
| ATOM | 1179 | CB | GLU | 1003 | 30.419 | 15.503 | -2.208 1.00 32.50 |
| ATOM | 1180 | CG | GLU | 1003 | 30.988 | 16.624 | -3.077 1.00 37.49 |
| ATOM | 1181 | CD | GLU | 1003 | 31.915 | 16.121 | -4.170 1.00 38.89 |
| ATOM | 1182 | OE1 | GLU | 1003 | 33.065 | 15.743 | -3.886 1.00 43.61 |
| ATOM | 1183 | OE2 | GLU | 1003 | 31.488 | 16.102 | -5.331 1.00 46.97 |
| ATOM | 1184 | C | GLU | 1003 | 31.591 | 16.044 | -0.117 1.00 25.24 |
| ATOM | 1185 | O | GLU | 1003 | 32.485 | 16.885 | -0.211 1.00 26.57 |
| ATOM | 1186 | N | HIS | 1004 | 30.748 | 15.953 | 0.913 1.00 23.16 |
| ATOM | 1188 | CA | HIS | 1004 | 30.746 | 16.884 | 2.040 1.00 19.58 |
| ATOM | 1189 | CB | HIS | 1004 | 29.508 | 16.719 | 2.912 1.00 19.12 |
| ATOM | 1190 | CG | HIS | 1004 | 28.227 | 17.024 | 2.208 1.00 23.47 |
| ATOM | 1191 | CD2 | HIS | 1004 | 27.173 | 17.784 | 2.570 1.00 23.78 |
| ATOM | 1192 | ND1 | HIS | 1004 | 27.911 | 16.508 | 0.964 1.00 27.88 |
| ATOM | 1194 | CE1 | HIS | 1004 | 26.718 | 16.936 | 0.596 1.00 20.57 |
| ATOM | 1195 | NE2 | HIS | 1004 | 26.246 | 17.710 | 1.554 1.00 23.61 |
| ATOM | 1197 | C | HIS | 1004 | 31.940 | 16.631 | 2.885 1.00 21.64 |
| ATOM | 1198 | O | HIS | 1004 | 32.753 | 17.508 | 3.075 1.00 25.00 |
| ATOM | 1199 | N | LEU | 1005 | 32.055 | 15.419 | 3.394 1.00 23.11 |
| ATOM | 1201 | CA | LEU | 1005 | 33.186 | 15.072 | 4.222 1.00 23.79 |
| ATOM | 1202 | CB | LEU | 1005 | 33.131 | 13.581 | 4.589 1.00 24.17 |
| ATOM | 1203 | CG | LEU | 1005 | 32.183 | 13.199 | 5.743 1.00 27.48 |
| ATOM | 1204 | CD1 | LEU | 1005 | 31.030 | 14.150 | 5.821 1.00 25.44 |
| ATOM | 1205 | CD2 | LEU | 1005 | 31.679 | 11.771 | 5.627 1.00 22.50 |
| ATOM | 1206 | C | LEU | 1005 | 34.506 | 15.467 | 3.558 1.00 20.41 |
| ATOM | 1207 | O | LEU | 1005 | 35.361 | 16.034 | 4.206 1.00 21.82 |
| ATOM | 1208 | N | ILE | 1006 | 34.668 | 15.212 | 2.264 1.00 19.50 |

FIG. 7(24)

| ATOM | 1210 | CA  | ILE | 1006 | 35.914 | 15.589 | 1.609  | 1.00 | 18.77 |
|------|------|-----|-----|------|--------|--------|--------|------|-------|
| ATOM | 1211 | CB  | ILE | 1006 | 36.128 | 14.806 | 0.276  | 1.00 | 16.46 |
| ATOM | 1212 | CG2 | ILE | 1006 | 37.602 | 14.777 | -0.103 | 1.00 | 12.82 |
| ATOM | 1213 | CG1 | ILE | 1006 | 35.718 | 13.341 | 0.441  | 1.00 | 20.16 |
| ATOM | 1214 | CD1 | ILE | 1006 | 35.961 | 12.446 | -0.834 | 1.00 | 11.88 |
| ATOM | 1215 | C   | ILE | 1006 | 35.998 | 17.136 | 1.377  | 1.00 | 22.88 |
| ATOM | 1216 | O   | ILE | 1006 | 37.113 | 17.730 | 1.431  | 1.00 | 21.25 |
| ATOM | 1217 | N   | CYS | 1007 | 34.854 | 17.788 | 1.108  | 1.00 | 21.47 |
| ATOM | 1219 | CA  | CYS | 1007 | 34.860 | 19.240 | 0.909  | 1.00 | 21.66 |
| ATOM | 1220 | CB  | CYS | 1007 | 33.522 | 19.825 | 0.431  | 1.00 | 24.87 |
| ATOM | 1221 | SG  | CYS | 1007 | 33.760 | 21.544 | -0.085 | 1.00 | 30.17 |
| ATOM | 1222 | C   | CYS | 1007 | 35.247 | 19.953 | 2.196  | 1.00 | 22.22 |
| ATOM | 1223 | O   | CYS | 1007 | 36.024 | 20.905 | 2.158  | 1.00 | 25.94 |
| ATOM | 1224 | N   | TYR | 1008 | 34.691 | 19.527 | 3.331  | 1.00 | 20.53 |
| ATOM | 1226 | CA  | TYR | 1008 | 35.030 | 20.132 | 4.617  | 1.00 | 17.94 |
| ATOM | 1227 | CB  | TYR | 1008 | 34.248 | 19.493 | 5.758  | 1.00 | 18.61 |
| ATOM | 1228 | CG  | TYR | 1008 | 32.753 | 19.488 | 5.626  | 1.00 | 17.97 |
| ATOM | 1229 | CD1 | TYR | 1008 | 32.019 | 18.455 | 6.175  | 1.00 | 16.67 |
| ATOM | 1230 | CE1 | TYR | 1008 | 30.641 | 18.462 | 6.158  | 1.00 | 22.78 |
| ATOM | 1231 | CD2 | TYR | 1008 | 32.059 | 20.549 | 5.031  | 1.00 | 22.19 |
| ATOM | 1232 | CE2 | TYR | 1008 | 30.646 | 20.569 | 5.011  | 1.00 | 20.60 |
| ATOM | 1233 | CZ  | TYR | 1008 | 29.949 | 19.513 | 5.579  | 1.00 | 23.22 |
| ATOM | 1234 | OH  | TYR | 1008 | 28.574 | 19.454 | 5.551  | 1.00 | 18.30 |
| ATOM | 1236 | C   | TYR | 1008 | 36.537 | 19.945 | 4.883  | 1.00 | 18.55 |
| ATOM | 1237 | O   | TYR | 1008 | 37.217 | 20.917 | 5.256  | 1.00 | 20.35 |
| ATOM | 1238 | N   | SER | 1009 | 37.056 | 18.726 | 4.642  | 1.00 | 14.74 |
| ATOM | 1240 | CA  | SER | 1009 | 38.476 | 18.409 | 4.852  | 1.00 | 13.39 |
| ATOM | 1241 | CB  | SER | 1009 | 38.810 | 16.962 | 4.473  | 1.00 | 17.24 |
| ATOM | 1242 | OG  | SER | 1009 | 38.018 | 16.001 | 5.152  | 1.00 | 26.04 |
| ATOM | 1244 | C   | SER | 1009 | 39.310 | 19.309 | 3.985  | 1.00 | 16.36 |
| ATOM | 1245 | O   | SER | 1009 | 40.317 | 19.864 | 4.446  | 1.00 | 20.21 |
| ATOM | 1246 | N   | PHE | 1010 | 38.953 | 19.375 | 2.699  | 1.00 | 20.97 |
| ATOM | 1248 | CA  | PHE | 1010 | 39.654 | 20.246 | 1.742  | 1.00 | 23.34 |
| ATOM | 1249 | CB  | PHE | 1010 | 38.985 | 20.126 | 0.365  | 1.00 | 18.83 |
| ATOM | 1250 | CG  | PHE | 1010 | 39.605 | 21.002 | -0.685 | 1.00 | 17.13 |
| ATOM | 1251 | CD1 | PHE | 1010 | 38.830 | 21.940 | -1.370 | 1.00 | 13.94 |
| ATOM | 1252 | CD2 | PHE | 1010 | 40.979 | 20.918 | -0.968 | 1.00 | 17.85 |
| ATOM | 1253 | CE1 | PHE | 1010 | 39.410 | 22.804 | -2.339 | 1.00 | 16.30 |
| ATOM | 1254 | CE2 | PHE | 1010 | 41.569 | 21.763 | -1.917 | 1.00 | 17.15 |
| ATOM | 1255 | CZ  | PHE | 1010 | 40.772 | 22.714 | -2.608 | 1.00 | 18.02 |

FIG. 7(25)

| | | | | | | | |
|---|---|---|---|---|---|---|---|
| ATOM | 1256 | C | PHE | 1010 | 39.688 | 21.746 | 2.242 | 1.00 | 22.02 |
| ATOM | 1257 | O | PHE | 1010 | 40.749 | 22.390 | 2.298 | 1.00 | 23.00 |
| ATOM | 1258 | N | GLN | 1011 | 38.535 | 22.271 | 2.643 | 1.00 | 19.25 |
| ATOM | 1260 | CA | GLN | 1011 | 38.418 | 23.640 | 3.159 | 1.00 | 19.07 |
| ATOM | 1261 | CB | GLN | 1011 | 36.980 | 23.945 | 3.480 | 1.00 | 12.84 |
| ATOM | 1262 | CG | GLN | 1011 | 36.117 | 24.005 | 2.270 | 1.00 | 6.53 |
| ATOM | 1263 | CD | GLN | 1011 | 34.713 | 24.371 | 2.659 | 1.00 | 18.81 |
| ATOM | 1264 | OE1 | GLN | 1011 | 34.490 | 25.382 | 3.347 | 1.00 | 21.22 |
| ATOM | 1265 | NE2 | GLN | 1011 | 33.760 | 23.525 | 2.302 | 1.00 | 26.88 |
| ATOM | 1268 | C | GLN | 1011 | 39.262 | 23.894 | 4.394 | 1.00 | 18.28 |
| ATOM | 1269 | O | GLN | 1011 | 39.840 | 24.982 | 4.543 | 1.00 | 19.80 |
| ATOM | 1270 | N | VAL | 1012 | 39.270 | 22.934 | 5.319 | 1.00 | 11.82 |
| ATOM | 1272 | CA | VAL | 1012 | 40.110 | 23.063 | 6.500 | 1.00 | 13.54 |
| ATOM | 1273 | CB | VAL | 1012 | 39.825 | 21.936 | 7.528 | 1.00 | 15.67 |
| ATOM | 1274 | CG1 | VAL | 1012 | 40.686 | 22.107 | 8.795 | 1.00 | 10.56 |
| ATOM | 1275 | CG2 | VAL | 1012 | 38.370 | 21.948 | 7.901 | 1.00 | 14.92 |
| ATOM | 1276 | C | VAL | 1012 | 41.618 | 23.068 | 6.068 | 1.00 | 16.72 |
| ATOM | 1277 | O | VAL | 1012 | 42.448 | 23.782 | 6.665 | 1.00 | 20.48 |
| ATOM | 1278 | N | ALA | 1013 | 42.001 | 22.291 | 5.051 | 1.00 | 15.90 |
| ATOM | 1280 | CA | ALA | 1013 | 43.401 | 22.352 | 4.602 | 1.00 | 17.77 |
| ATOM | 1281 | CB | ALA | 1013 | 43.732 | 21.206 | 3.638 | 1.00 | 10.59 |
| ATOM | 1282 | C | ALA | 1013 | 43.685 | 23.755 | 3.963 | 1.00 | 15.74 |
| ATOM | 1283 | O | ALA | 1013 | 44.764 | 24.302 | 4.139 | 1.00 | 17.49 |
| ATOM | 1284 | N | LYS | 1014 | 42.718 | 24.342 | 3.244 | 1.00 | 17.18 |
| ATOM | 1286 | CA | LYS | 1014 | 42.866 | 25.706 | 2.665 | 1.00 | 15.11 |
| ATOM | 1287 | CB | LYS | 1014 | 41.557 | 26.152 | 2.020 | 1.00 | 23.73 |
| ATOM | 1288 | CG | LYS | 1014 | 41.146 | 25.474 | 0.748 | 1.00 | 23.57 |
| ATOM | 1289 | CD | LYS | 1014 | 41.963 | 26.033 | -0.354 | 1.00 | 26.38 |
| ATOM | 1290 | CE | LYS | 1014 | 41.172 | 25.978 | -1.617 | 1.00 | 38.71 |
| ATOM | 1291 | NZ | LYS | 1014 | 42.034 | 26.404 | -2.776 | 1.00 | 50.36 |
| ATOM | 1295 | C | LYS | 1014 | 43.105 | 26.678 | 3.823 | 1.00 | 11.16 |
| ATOM | 1296 | O | LYS | 1014 | 44.066 | 27.452 | 3.818 | 1.00 | 13.85 |
| ATOM | 1297 | N | GLY | 1015 | 42.210 | 26.590 | 4.816 | 1.00 | 10.82 |
| ATOM | 1299 | CA | GLY | 1015 | 42.250 | 27.403 | 6.017 | 1.00 | 12.48 |
| ATOM | 1300 | C | GLY | 1015 | 43.584 | 27.327 | 6.715 | 1.00 | 17.17 |
| ATOM | 1301 | O | GLY | 1015 | 44.124 | 28.349 | 7.130 | 1.00 | 19.92 |
| ATOM | 1302 | N | MET | 1016 | 44.159 | 26.128 | 6.763 | 1.00 | 17.82 |
| ATOM | 1304 | CA | MET | 1016 | 45.426 | 25.927 | 7.439 | 1.00 | 15.78 |
| ATOM | 1305 | CB | MET | 1016 | 45.516 | 24.488 | 7.925 | 1.00 | 17.77 |
| ATOM | 1306 | CG | MET | 1016 | 44.538 | 24.156 | 9.057 | 1.00 | 15.19 |
| ATOM | 1307 | SD | MET | 1016 | 44.931 | 24.991 | 10.623 | 1.00 | 15.49 |

FIG. 7(26)

| | | | | | | | |
|---|---|---|---|---|---|---|---|
| ATOM | 1308 | CE | MET | 1016 | 46.642 24.894 10.658 | 1.00 | 5.63 |
| ATOM | 1309 | C | MET | 1016 | 46.625 26.321 6.618 | 1.00 | 14.62 |
| ATOM | 1310 | O | MET | 1016 | 47.680 26.667 7.163 | 1.00 | 15.76 |
| ATOM | 1311 | N | GLU | 1017 | 46.487 26.208 5.305 | 1.00 | 14.65 |
| ATOM | 1313 | CA | GLU | 1017 | 47.552 26.608 4.384 | 1.00 | 21.43 |
| ATOM | 1314 | CB | GLU | 1017 | 47.177 26.195 2.947 | 1.00 | 21.43 |
| ATOM | 1315 | CG | GLU | 1017 | 48.162 26.622 1.878 | 1.00 | 22.82 |
| ATOM | 1316 | CD | GLU | 1017 | 47.634 26.421 0.436 | 1.00 | 27.12 |
| ATOM | 1317 | OE1 | GLU | 1017 | 46.457 26.769 0.141 | 1.00 | 24.95 |
| ATOM | 1318 | OE2 | GLU | 1017 | 48.418 25.927 -0.424 | 1.00 | 32.93 |
| ATOM | 1319 | C | GLU | 1017 | 47.667 28.145 4.535 | 1.00 | 18.38 |
| ATOM | 1320 | O | GLU | 1017 | 48.760 28.668 4.593 | 1.00 | 17.43 |
| ATOM | 1321 | N | PHE | 1018 | 46.526 28.839 4.677 | 1.00 | 19.09 |
| ATOM | 1323 | CA | PHE | 1018 | 46.509 30.295 4.894 | 1.00 | 20.74 |
| ATOM | 1324 | CB | PHE | 1018 | 45.067 30.848 4.870 | 1.00 | 27.18 |
| ATOM | 1325 | CG | PHE | 1018 | 44.942 32.338 5.248 | 1.00 | 25.91 |
| ATOM | 1326 | CD1 | PHE | 1018 | 44.477 32.718 6.521 | 1.00 | 26.19 |
| ATOM | 1327 | CD2 | PHE | 1018 | 45.300 33.345 4.348 | 1.00 | 25.16 |
| ATOM | 1328 | CE1 | PHE | 1018 | 44.381 34.059 6.890 | 1.00 | 27.10 |
| ATOM | 1329 | CE2 | PHE | 1018 | 45.208 34.708 4.712 | 1.00 | 28.34 |
| ATOM | 1330 | CZ | PHE | 1018 | 44.754 35.064 5.982 | 1.00 | 26.60 |
| ATOM | 1331 | C | PHE | 1018 | 47.179 30.663 6.216 | 1.00 | 18.20 |
| ATOM | 1332 | O | PHE | 1018 | 48.139 31.430 6.228 | 1.00 | 15.08 |
| ATOM | 1333 | N | LEU | 1019 | 46.676 30.122 7.328 | 1.00 | 16.94 |
| ATOM | 1335 | CA | LEU | 1019 | 47.259 30.414 8.654 | 1.00 | 19.44 |
| ATOM | 1336 | CB | LEU | 1019 | 46.673 29.533 9.754 | 1.00 | 22.88 |
| ATOM | 1337 | CG | LEU | 1019 | 45.238 29.773 10.165 | 1.00 | 24.41 |
| ATOM | 1338 | CD1 | LEU | 1019 | 44.956 28.916 11.388 | 1.00 | 24.01 |
| ATOM | 1339 | CD2 | LEU | 1019 | 45.084 31.277 10.485 | 1.00 | 25.61 |
| ATOM | 1340 | C | LEU | 1019 | 48.736 30.173 8.660 | 1.00 | 19.44 |
| ATOM | 1341 | O | LEU | 1019 | 49.493 30.896 9.316 | 1.00 | 18.98 |
| ATOM | 1342 | N | ALA | 1020 | 49.135 29.076 8.023 | 1.00 | 19.45 |
| ATOM | 1344 | CA | ALA | 1020 | 50.545 28.747 7.961 | 1.00 | 22.29 |
| ATOM | 1345 | CB | ALA | 1020 | 50.748 27.350 7.397 | 1.00 | 21.86 |
| ATOM | 1346 | C | ALA | 1020 | 51.252 29.829 7.115 | 1.00 | 26.13 |
| ATOM | 1347 | O | ALA | 1020 | 52.348 30.257 7.471 | 1.00 | 25.25 |
| ATOM | 1348 | N | SER | 1021 | 50.600 30.323 6.050 | 1.00 | 29.72 |
| ATOM | 1350 | CA | SER | 1021 | 51.194 31.384 5.219 | 1.00 | 27.59 |
| ATOM | 1351 | CB | SER | 1021 | 50.289 31.754 4.026 | 1.00 | 23.95 |

FIG. 7(27)

| | | | | | | | |
|---|---|---|---|---|---|---|---|
| ATOM | 1352 | OG | SER | 1021 | 49.252 | 32.662 | 4.349 1.00 22.60 |
| ATOM | 1354 | C | SER | 1021 | 51.469 | 32.614 | 6.109 1.00 32.83 |
| ATOM | 1355 | O | SER | 1021 | 52.570 | 33.172 | 6.073 1.00 36.57 |
| ATOM | 1356 | N | ARG | 1022 | 50.513 | 32.957 | 6.981 1.00 31.88 |
| ATOM | 1358 | CA | ARG | 1022 | 50.645 | 34.093 | 7.901 1.00 22.64 |
| ATOM | 1359 | CB | ARG | 1022 | 49.294 | 34.483 | 8.465 1.00 17.89 |
| ATOM | 1360 | CG | ARG | 1022 | 48.254 | 34.691 | 7.420 1.00 17.72 |
| ATOM | 1361 | CD | ARG | 1022 | 48.648 | 35.816 | 6.468 1.00 18.00 |
| ATOM | 1362 | NE | ARG | 1022 | 49.714 | 36.666 | 6.993 1.00 31.94 |
| ATOM | 1364 | CZ | ARG | 1022 | 49.625 | 37.980 | 7.168 1.00 30.72 |
| ATOM | 1365 | NH1 | ARG | 1022 | 50.653 | 38.644 | 7.662 1.00 23.85 |
| ATOM | 1368 | NH2 | ARG | 1022 | 48.508 | 38.620 | 6.862 1.00 40.00 |
| ATOM | 1371 | C | ARG | 1022 | 51.563 | 33.787 | 9.056 1.00 24.84 |
| ATOM | 1372 | O | ARG | 1022 | 51.718 | 34.612 | 9.960 1.00 23.27 |
| ATOM | 1373 | N | LYS | 1023 | 52.115 | 32.576 | 9.061 1.00 23.84 |
| ATOM | 1375 | CA | LYS | 1023 | 53.039 | 32.137 | 10.094 1.00 23.59 |
| ATOM | 1376 | CB | LYS | 1023 | 54.237 | 33.067 | 10.196 1.00 22.44 |
| ATOM | 1377 | C | LYS | 1023 | 52.404 | 31.899 | 11.456 1.00 25.21 |
| ATOM | 1378 | O | LYS | 1023 | 53.054 | 32.024 | 12.504 1.00 28.54 |
| ATOM | 1379 | N | CYS | 1024 | 51.164 | 31.435 | 11.411 1.00 20.82 |
| ATOM | 1381 | CA | CYS | 1024 | 50.404 | 31.114 | 12.595 1.00 28.12 |
| ATOM | 1382 | CB | CYS | 1024 | 48.982 | 31.709 | 12.472 1.00 30.32 |
| ATOM | 1383 | SG | CYS | 1024 | 48.936 | 33.504 | 12.847 1.00 33.73 |
| ATOM | 1384 | C | CYS | 1024 | 50.388 | 29.576 | 12.729 1.00 32.20 |
| ATOM | 1385 | O | CYS | 1024 | 50.636 | 28.882 | 11.756 1.00 38.70 |
| ATOM | 1386 | N | ILE | 1025 | 50.167 | 29.057 | 13.934 1.00 30.55 |
| ATOM | 1388 | CA | ILE | 1025 | 50.123 | 27.619 | 14.216 1.00 33.60 |
| ATOM | 1389 | CB | ILE | 1025 | 51.406 | 27.169 | 14.970 1.00 36.10 |
| ATOM | 1390 | CG2 | ILE | 1025 | 51.223 | 25.807 | 15.619 1.00 38.88 |
| ATOM | 1391 | CG1 | ILE | 1025 | 52.585 | 27.121 | 13.988 1.00 38.38 |
| ATOM | 1392 | CD1 | ILE | 1025 | 53.913 | 27.422 | 14.604 1.00 34.51 |
| ATOM | 1393 | C | ILE | 1025 | 48.891 | 27.526 | 15.104 1.00 33.66 |
| ATOM | 1394 | O | ILE | 1025 | 48.751 | 28.301 | 16.034 1.00 41.71 |
| ATOM | 1395 | N | HIS | 1026 | 47.958 | 26.643 | 14.797 1.00 31.27 |
| ATOM | 1397 | CA | HIS | 1026 | 46.742 | 26.570 | 15.589 1.00 27.97 |
| ATOM | 1398 | CB | HIS | 1026 | 45.691 | 25.745 | 14.861 1.00 23.43 |
| ATOM | 1399 | CG | HIS | 1026 | 44.283 | 26.091 | 15.229 1.00 30.06 |
| ATOM | 1400 | CD2 | HIS | 1026 | 43.342 | 26.801 | 14.560 1.00 33.43 |
| ATOM | 1401 | ND1 | HIS | 1026 | 43.680 | 25.659 | 16.393 1.00 24.53 |

FIG. 7(28)

| | | | | |
|---|---|---|---|---|
| ATOM 1403 CE1 HIS 1026 | 42.428 | 26.085 | 16.424 | 1.00 26.31 |
| ATOM 1404 NE2 HIS 1026 | 42.199 | 26.781 | 15.321 | 1.00 29.05 |
| ATOM 1406 C HIS 1026 | 46.901 | 26.086 | 17.036 | 1.00 30.13 |
| ATOM 1407 O HIS 1026 | 46.335 | 26.681 | 17.955 | 1.00 37.96 |
| ATOM 1408 N ARG 1027 | 47.662 | 25.024 | 17.244 | 1.00 26.58 |
| ATOM 1410 CA ARG 1027 | 47.872 | 24.429 | 18.583 | 1.00 31.87 |
| ATOM 1411 CB ARG 1027 | 48.235 | 25.483 | 19.666 | 1.00 20.17 |
| ATOM 1412 C ARG 1027 | 46.762 | 23.449 | 19.055 | 1.00 31.55 |
| ATOM 1413 O ARG 1027 | 47.047 | 22.477 | 19.742 | 1.00 38.11 |
| ATOM 1414 N ASP 1028 | 45.528 | 23.629 | 18.597 | 1.00 30.85 |
| ATOM 1416 CA ASP 1028 | 44.466 | 22.698 | 18.955 | 1.00 26.34 |
| ATOM 1417 CB ASP 1028 | 43.788 | 23.098 | 20.248 | 1.00 32.60 |
| ATOM 1418 CG ASP 1028 | 42.847 | 22.020 | 20.755 | 1.00 35.64 |
| ATOM 1419 OD1 ASP 1028 | 41.692 | 22.346 | 21.096 | 1.00 36.08 |
| ATOM 1420 OD2 ASP 1028 | 43.267 | 20.842 | 20.790 | 1.00 40.39 |
| ATOM 1421 C ASP 1028 | 43.435 | 22.565 | 17.841 | 1.00 26.23 |
| ATOM 1422 O ASP 1028 | 42.276 | 22.926 | 17.998 | 1.00 23.40 |
| ATOM 1423 N LEU 1029 | 43.884 | 22.034 | 16.708 | 1.00 24.88 |
| ATOM 1425 CA LEU 1029 | 43.053 | 21.842 | 15.533 | 1.00 23.16 |
| ATOM 1426 CB LEU 1029 | 43.958 | 21.772 | 14.299 | 1.00 18.78 |
| ATOM 1427 CG LEU 1029 | 43.221 | 21.714 | 12.965 | 1.00 20.21 |
| ATOM 1428 CD1 LEU 1029 | 42.349 | 22.952 | 12.812 | 1.00 15.13 |
| ATOM 1429 CD2 LEU 1029 | 44.249 | 21.601 | 11.827 | 1.00 22.91 |
| ATOM 1430 C LEU 1029 | 42.237 | 20.562 | 15.700 | 1.00 25.25 |
| ATOM 1431 O LEU 1029 | 42.765 | 19.473 | 15.591 | 1.00 30.47 |
| ATOM 1432 N ALA 1030 | 40.949 | 20.703 | 15.957 | 1.00 25.99 |
| ATOM 1434 CA ALA 1030 | 40.062 | 19.574 | 16.182 | 1.00 25.19 |
| ATOM 1435 CB ALA 1030 | 39.872 | 19.387 | 17.679 | 1.00 24.55 |
| ATOM 1436 C ALA 1030 | 38.761 | 20.007 | 15.558 | 1.00 27.35 |
| ATOM 1437 O ALA 1030 | 38.611 | 21.202 | 15.302 | 1.00 33.46 |
| ATOM 1438 N ALA 1031 | 37.797 | 19.094 | 15.379 | 1.00 25.19 |
| ATOM 1440 CA ALA 1031 | 36.508 | 19.451 | 14.752 | 1.00 22.16 |
| ATOM 1441 CB ALA 1031 | 35.772 | 18.210 | 14.270 | 1.00 21.71 |
| ATOM 1442 C ALA 1031 | 35.551 | 20.353 | 15.536 | 1.00 20.96 |
| ATOM 1443 O ALA 1031 | 34.639 | 20.950 | 14.944 | 1.00 21.36 |
| ATOM 1444 N ARG 1032 | 35.712 | 20.388 | 16.859 | 1.00 22.49 |
| ATOM 1446 CA ARG 1032 | 34.898 | 21.246 | 17.736 | 1.00 27.01 |
| ATOM 1447 CB ARG 1032 | 35.157 | 20.945 | 19.220 | 1.00 25.22 |
| ATOM 1448 CG ARG 1032 | 36.534 | 21.451 | 19.707 | 1.00 34.44 |
| ATOM 1449 CD ARG 1032 | 37.150 | 20.503 | 20.770 | 1.00 46.39 |

FIG. 7(29)

| | | | | | | | |
|---|---|---|---|---|---|---|---|
| ATOM | 1450 | NE | ARG | 1032 | 38.554 | 20.752 | 21.158 | 1.00 | 41.28 |
| ATOM | 1452 | CZ | ARG | 1032 | 39.464 | 19.799 | 21.352 | 1.00 | 32.28 |
| ATOM | 1453 | NH1 | ARG | 1032 | 40.677 | 20.129 | 21.709 | 1.00 | 27.74 |
| ATOM | 1456 | NH2 | ARG | 1032 | 39.178 | 18.524 | 21.148 | 1.00 | 31.24 |
| ATOM | 1459 | C | ARG | 1032 | 35.296 | 22.708 | 17.482 | 1.00 | 25.91 |
| ATOM | 1460 | O | ARG | 1032 | 34.601 | 23.605 | 17.935 | 1.00 | 30.23 |
| ATOM | 1461 | N | ASN | 1033 | 36.451 | 22.911 | 16.840 | 1.00 | 20.90 |
| ATOM | 1463 | CA | ASN | 1033 | 37.008 | 24.222 | 16.495 | 1.00 | 15.77 |
| ATOM | 1464 | CB | ASN | 1033 | 38.497 | 24.290 | 16.813 | 1.00 | 18.29 |
| ATOM | 1465 | CG | ASN | 1033 | 38.760 | 24.160 | 18.254 | 1.00 | 20.60 |
| ATOM | 1466 | OD1 | ASN | 1033 | 37.891 | 24.445 | 19.067 | 1.00 | 29.84 |
| ATOM | 1467 | ND2 | ASN | 1033 | 39.929 | 23.677 | 18.601 | 1.00 | 18.08 |
| ATOM | 1470 | C | ASN | 1033 | 36.839 | 24.535 | 15.019 | 1.00 | 19.29 |
| ATOM | 1471 | O | ASN | 1033 | 37.619 | 25.303 | 14.450 | 1.00 | 17.18 |
| ATOM | 1472 | N | ILE | 1034 | 35.934 | 23.822 | 14.366 | 1.00 | 17.56 |
| ATOM | 1474 | CA | ILE | 1034 | 35.631 | 24.092 | 12.972 | 1.00 | 17.92 |
| ATOM | 1475 | CB | ILE | 1034 | 35.813 | 22.868 | 12.091 | 1.00 | 15.66 |
| ATOM | 1476 | CG2 | ILE | 1034 | 35.364 | 23.192 | 10.647 | 1.00 | 12.61 |
| ATOM | 1477 | CG1 | ILE | 1034 | 37.247 | 22.349 | 12.221 | 1.00 | 10.08 |
| ATOM | 1478 | CD1 | ILE | 1034 | 38.312 | 23.384 | 11.994 | 1.00 | 18.10 |
| ATOM | 1479 | C | ILE | 1034 | 34.147 | 24.381 | 13.075 | 1.00 | 21.87 |
| ATOM | 1480 | O | ILE | 1034 | 33.410 | 23.592 | 13.669 | 1.00 | 26.72 |
| ATOM | 1481 | N | LEU | 1035 | 33.711 | 25.524 | 12.575 | 1.00 | 21.91 |
| ATOM | 1483 | CA | LEU | 1035 | 32.311 | 25.883 | 12.670 | 1.00 | 19.45 |
| ATOM | 1484 | CB | LEU | 1035 | 32.190 | 27.310 | 13.181 | 1.00 | 18.73 |
| ATOM | 1485 | CG | LEU | 1035 | 32.102 | 27.454 | 14.691 | 1.00 | 21.53 |
| ATOM | 1486 | CD1 | LEU | 1035 | 33.019 | 26.518 | 15.456 | 1.00 | 8.66 |
| ATOM | 1487 | CD2 | LEU | 1035 | 32.391 | 28.881 | 15.016 | 1.00 | 19.34 |
| ATOM | 1488 | C | LEU | 1035 | 31.700 | 25.764 | 11.316 | 1.00 | 20.15 |
| ATOM | 1489 | O | LEU | 1035 | 32.377 | 25.977 | 10.310 | 1.00 | 21.51 |
| ATOM | 1490 | N | LEU | 1036 | 30.429 | 25.390 | 11.275 | 1.00 | 24.13 |
| ATOM | 1492 | CA | LEU | 1036 | 29.745 | 25.237 | 10.006 | 1.00 | 26.96 |
| ATOM | 1493 | CB | LEU | 1036 | 29.027 | 23.882 | 9.909 | 1.00 | 20.57 |
| ATOM | 1494 | CG | LEU | 1036 | 28.149 | 23.631 | 8.681 | 1.00 | 17.23 |
| ATOM | 1495 | CD1 | LEU | 1036 | 28.877 | 23.617 | 7.360 | 1.00 | 7.53 |
| ATOM | 1496 | CD2 | LEU | 1036 | 27.566 | 22.306 | 8.900 | 1.00 | 18.85 |
| ATOM | 1497 | C | LEU | 1036 | 28.827 | 26.432 | 9.755 | 1.00 | 31.45 |
| ATOM | 1498 | O | LEU⁻ | 1036 | 27.953 | 26.794 | 10.557 | 1.00 | 29.93 |
| ATOM | 1499 | N | SER | 1037 | 29.094 | 27.061 | 8.628 | 1.00 | 34.52 |
| ATOM | 1501 | CA | SER | 1037 | 28.410 | 28.248 | 8.215 | 1.00 | 37.11 |

FIG. 7(30)

```
ATOM   1502  CB  SER 1037      29.448 29.220  7.632 1.00 41.11
ATOM   1503  OG  SER 1037      28.879 30.439  7.193 1.00 44.80
ATOM   1505  C   SER 1037      27.367 27.890  7.209 1.00 39.39
ATOM   1506  O   SER 1037      27.045 26.735  7.024 1.00 42.14
ATOM   1507  N   GLU 1038      26.884 28.912  6.531 1.00 44.94
ATOM   1509  CA  GLU 1038      25.845 28.806  5.534 1.00 50.37
ATOM   1510  CB  GLU 1038      25.685 30.152  4.792 1.00 56.15
ATOM   1511  CG  GLU 1038      25.599 31.391  5.676 1.00 55.19
ATOM   1512  CD  GLU 1038      24.518 31.270  6.708 1.00 59.42
ATOM   1513  OE1 GLU 1038      23.464 30.637  6.419 1.00 58.62
ATOM   1514  OE2 GLU 1038      24.736 31.806  7.816 1.00 63.52
ATOM   1515  C   GLU 1038      25.954 27.672  4.518 1.00 51.35
ATOM   1516  O   GLU 1038      25.619 26.521  4.816 1.00 57.04
ATOM   1517  N   LYS 1039      26.414 27.997  3.317 1.00 46.28
ATOM   1519  CA  LYS 1039      26.467 27.021  2.251 1.00 43.05
ATOM   1520  CB  LYS 1039      26.455 27.729  0.898 1.00 41.05
ATOM   1521  C   LYS 1039      27.689 26.155  2.401 1.00 44.31
ATOM   1522  O   LYS 1039      28.687 26.358  1.697 1.00 50.06
ATOM   1523  N   ASN 1040      27.611 25.210  3.339 1.00 37.02
ATOM   1525  CA  ASN 1040      28.701 24.283  3.630 1.00 32.65
ATOM   1526  CB  ASN 1040      28.647 23.041  2.761 1.00 31.69
ATOM   1527  CG  ASN 1040      27.641 22.061  3.267 1.00 31.29
ATOM   1528  OD1 ASN 1040      26.740 21.693  2.553 1.00 38.80
ATOM   1529  ND2 ASN 1040      27.749 21.680  4.530 1.00 36.05
ATOM   1532  C   ASN 1040      30.096 24.844  3.656 1.00 28.45
ATOM   1533  O   ASN 1040      31.079 24.162  3.300 1.00 26.00
ATOM   1534  N   VAL 1041      30.174 26.101  4.073 1.00 23.77
ATOM   1536  CA  VAL 1041      31.447 26.739  4.207 1.00 16.56
ATOM   1537  CB  VAL 1041      31.382 28.274  3.940 1.00 16.16
ATOM   1538  CG1 VAL 1041      32.709 28.948  4.315 1.00  8.57
ATOM   1539  CG2 VAL 1041      31.124 28.509  2.470 1.00  6.79
ATOM   1540  C   VAL 1041      31.726 26.382  5.646 1.00 15.50
ATOM   1541  O   VAL 1041      30.825 26.333  6.485 1.00  9.73
ATOM   1542  N   VAL 1042      32.967 26.022  5.883 1.00 18.82
ATOM   1544  CA  VAL 1042      33.431 25.607  7.185 1.00 19.76
ATOM   1545  CB  VAL 1042      33.907 24.110  7.051 1.00 22.19
ATOM   1546  CG1 VAL 1042      35.439 23.993  7.041 1.00 18.66
ATOM   1547  CG2 VAL 1042      33.247 23.242  8.100 1.00 22.95
ATOM   1548  C   VAL 1042      34.580 26.607  7.483 1.00 20.50
ATOM   1549  O   VAL 1042      35.348 26.960  6.575 1.00 17.75
```

FIG. 7(31)

| | | | | | | | |
|---|---|---|---|---|---|---|---|
| ATOM | 1550 | N   | LYS | 1043 | 34.675 | 27.082 |  8.726 | 1.00 18.30 |
| ATOM | 1552 | CA  | LYS | 1043 | 35.679 | 28.070 |  9.103 | 1.00 17.43 |
| ATOM | 1553 | CB  | LYS | 1043 | 34.977 | 29.420 |  9.277 | 1.00 17.68 |
| ATOM | 1554 | CG  | LYS | 1043 | 34.202 | 29.845 |  8.031 | 1.00 19.19 |
| ATOM | 1555 | CD  | LYS | 1043 | 33.560 | 31.228 |  8.186 | 1.00 26.86 |
| ATOM | 1556 | CE  | LYS | 1043 | 33.270 | 31.885 |  6.820 | 1.00 18.32 |
| ATOM | 1557 | NZ  | LYS | 1043 | 34.353 | 32.806 |  6.425 | 1.00 22.63 |
| ATOM | 1561 | C   | LYS | 1043 | 36.373 | 27.687 | 10.399 | 1.00 18.35 |
| ATOM | 1562 | O   | LYS | 1043 | 35.709 | 27.235 | 11.330 | 1.00 17.37 |
| ATOM | 1563 | N   | ILE | 1044 | 37.692 | 27.880 | 10.461 | 1.00 17.47 |
| ATOM | 1565 | CA  | ILE | 1044 | 38.504 | 27.558 | 11.645 | 1.00 21.49 |
| ATOM | 1566 | CB  | ILE | 1044 | 40.010 | 27.390 | 11.267 | 1.00 20.48 |
| ATOM | 1567 | CG2 | ILE | 1044 | 40.896 | 27.250 | 12.502 | 1.00 15.75 |
| ATOM | 1568 | CG1 | ILE | 1044 | 40.221 | 26.237 | 10.300 | 1.00 14.66 |
| ATOM | 1569 | CD1 | ILE | 1044 | 41.584 | 26.344 |  9.669 | 1.00 12.76 |
| ATOM | 1570 | C   | ILE | 1044 | 38.432 | 28.735 | 12.626 | 1.00 30.73 |
| ATOM | 1571 | O   | ILE | 1044 | 38.370 | 29.888 | 12.207 | 1.00 31.68 |
| ATOM | 1572 | N   | CYS | 1045 | 38.454 | 28.436 | 13.918 | 1.00 38.50 |
| ATOM | 1574 | CA  | CYS | 1045 | 38.437 | 29.444 | 14.968 | 1.00 48.73 |
| ATOM | 1575 | CB  | CYS | 1045 | 37.027 | 29.586 | 15.558 | 1.00 50.35 |
| ATOM | 1576 | SG  | CYS | 1045 | 36.259 | 28.069 | 16.173 | 1.00 59.69 |
| ATOM | 1577 | C   | CYS | 1045 | 39.473 | 29.041 | 16.033 | 1.00 54.63 |
| ATOM | 1578 | O   | CYS | 1045 | 39.981 | 27.912 | 15.986 | 1.00 54.88 |
| ATOM | 1579 | N   | ASP | 1046 | 39.811 | 29.954 | 16.956 | 1.00 64.20 |
| ATOM | 1581 | CA  | ASP | 1046 | 40.816 | 29.700 | 18.021 | 1.00 69.98 |
| ATOM | 1582 | CB  | ASP | 1046 | 40.454 | 28.407 | 18.788 | 1.00 72.94 |
| ATOM | 1583 | CG  | ASP | 1046 | 41.338 | 28.165 | 20.009 | 1.00 75.40 |
| ATOM | 1584 | OD1 | ASP | 1046 | 40.930 | 28.584 | 21.110 | 1.00 77.66 |
| ATOM | 1585 | OD2 | ASP | 1046 | 42.428 | 27.547 | 19.878 | 1.00 75.18 |
| ATOM | 1586 | C   | ASP | 1046 | 42.219 | 29.580 | 17.354 | 1.00 74.21 |
| ATOM | 1587 | O   | ASP | 1046 | 43.183 | 29.036 | 17.940 | 1.00 74.94 |
| ATOM | 1588 | N   | PHE | 1047 | 42.307 | 30.205 | 16.171 | 1.00 75.46 |
| ATOM | 1590 | CA  | PHE | 1047 | 43.462 | 30.212 | 15.245 | 1.00 71.53 |
| ATOM | 1591 | CB  | PHE | 1047 | 42.919 | 30.267 | 13.790 | 1.00 72.10 |
| ATOM | 1592 | CG  | PHE | 1047 | 41.906 | 31.381 | 13.526 | 1.00 71.34 |
| ATOM | 1593 | CD1 | PHE | 1047 | 42.139 | 32.327 | 12.526 | 1.00 74.26 |
| ATOM | 1594 | CD2 | PHE | 1047 | 40.747 | 31.501 | 14.284 | 1.00 69.46 |
| ATOM | 1595 | CE1 | PHE | 1047 | 41.242 | 33.367 | 12.293 | 1.00 70.87 |
| ATOM | 1596 | CE2 | PHE | 1047 | 39.847 | 32.533 | 14.066 | 1.00 67.97 |
| ATOM | 1597 | CZ  | PHE | 1047 | 40.096 | 33.467 | 13.068 | 1.00 71.41 |

FIG. 7(32)

```
ATOM  1598 C   PHE 1047    44.681 31.163 15.426 1.00 67.78
ATOM  1599 O   PHE 1047    44.507 32.345 15.797 1.00 63.26
ATOM  1601 CB  ASP 1064    29.579 17.003 25.123 1.00 69.86
ATOM  1602 CG  ASP 1064    30.534 16.464 24.050 1.00 69.93
ATOM  1603 OD1 ASP 1064    31.028 15.321 24.179 1.00 71.35
ATOM  1604 OD2 ASP 1064    30.776 17.189 23.063 1.00 71.45
ATOM  1605 C   ASP 1064    31.511 17.821 26.539 1.00 64.90
ATOM  1606 O   ASP 1064    31.512 19.029 26.788 1.00 64.09
ATOM  1609 N   ASP 1064    29.229 17.550 27.534 1.00 67.30
ATOM  1611 CA  ASP 1064    30.204 17.019 26.533 1.00 67.58
ATOM  1612 N   ALA 1065    32.617 17.135 26.278 1.00 61.87
ATOM  1614 CA  ALA 1065    33.932 17.759 26.244 1.00 58.06
ATOM  1615 CB  ALA 1065    34.479 17.935 27.650 1.00 56.61
ATOM  1616 C   ALA 1065    34.888 16.915 25.397 1.00 57.97
ATOM  1617 O   ALA 1065    34.491 15.906 24.788 1.00 56.86
ATOM  1618 N   ARG 1066    36.155 17.313 25.400 1.00 54.64
ATOM  1620 CA  ARG 1066    37.182 16.664 24.607 1.00 50.99
ATOM  1621 CB  ARG 1066    37.538 17.539 23.393 1.00 49.53
ATOM  1622 CG  ARG 1066    36.459 17.608 22.335 1.00 52.76
ATOM  1623 CD  ARG 1066    36.866 16.805 21.125 1.00 57.63
ATOM  1624 NE  ARG 1066    35.847 16.645 20.093 1.00 57.02
ATOM  1626 CZ  ARG 1066    35.976 17.033 18.824 1.00 55.63
ATOM  1627 NH1 ARG 1066    34.984 16.797 17.995 1.00 57.63
ATOM  1630 NH2 ARG 1066    37.046 17.691 18.385 1.00 40.52
ATOM  1633 C   ARG 1066    38.428 16.513 25.427 1.00 49.01
ATOM  1634 O   ARG 1066    38.652 17.274 26.364 1.00 46.29
ATOM  1635 N   LEU 1067    39.251 15.546 25.041 1.00 46.48
ATOM  1637 CA  LEU 1067    40.510 15.320 25.709 1.00 45.62
ATOM  1638 CB  LEU 1067    40.703 13.840 26.073 1.00 45.53
ATOM  1639 CG  LEU 1067    41.335 13.519 27.441 1.00 44.07
ATOM  1640 CD1 LEU 1067    42.236 12.322 27.273 1.00 37.52
ATOM  1641 CD2 LEU 1067    42.109 14.710 28.057 1.00 39.60
ATOM  1642 C   LEU 1067    41.530 15.778 24.677 1.00 42.00
ATOM  1643 O   LEU 1067    41.983 15.010 23.832 1.00 41.05
ATOM  1644 N   PRO 1068    41.854 17.072 24.698 1.00 41.22
ATOM  1645 CD  PRO 1068    41.265 18.104 25.584 1.00 34.16
ATOM  1646 CA  PRO 1068    42.817 17.661 23.761 1.00 38.41
ATOM  1647 CB  PRO 1068    42.919 19.104 24.277 1.00 36.08
ATOM  1648 CG  PRO 1068    41.496 19.355 24.828 1.00 29.23
ATOM  1649 C   PRO 1068    44.197 16.961 23.571 1.00 35.36
```

FIG. 7(33)

| | | | | | | | |
|---|---|---|---|---|---|---|---|
| ATOM | 1650 | O   | PRO | 1068 | 44.932 | 17.258 | 22.623 1.00 37.80 |
| ATOM | 1651 | N   | LEU | 1069 | 44.552 | 16.040 | 24.455 1.00 33.98 |
| ATOM | 1653 | CA  | LEU | 1069 | 45.829 | 15.337 | 24.333 1.00 35.06 |
| ATOM | 1654 | CB  | LEU | 1069 | 46.092 | 14.517 | 25.601 1.00 37.80 |
| ATOM | 1655 | CG  | LEU | 1069 | 47.228 | 13.497 | 25.488 1.00 40.67 |
| ATOM | 1656 | CD1 | LEU | 1069 | 48.599 | 14.156 | 25.752 1.00 36.35 |
| ATOM | 1657 | CD2 | LEU | 1069 | 46.939 | 12.333 | 26.445 1.00 40.75 |
| ATOM | 1658 | C   | LEU | 1069 | 45.776 | 14.397 | 23.121 1.00 34.16 |
| ATOM | 1659 | O   | LEU | 1069 | 46.787 | 14.115 | 22.461 1.00 32.14 |
| ATOM | 1660 | N   | LYS | 1070 | 44.571 | 13.916 | 22.859 1.00 28.95 |
| ATOM | 1662 | CA  | LYS | 1070 | 44.280 | 13.014 | 21.765 1.00 28.17 |
| ATOM | 1663 | CB  | LYS | 1070 | 42.828 | 12.569 | 21.911 1.00 22.17 |
| ATOM | 1664 | CG  | LYS | 1070 | 42.553 | 11.730 | 23.144 1.00 22.02 |
| ATOM | 1665 | CD  | LYS | 1070 | 41.085 | 11.317 | 23.107 1.00 24.17 |
| ATOM | 1666 | CE  | LYS | 1070 | 40.851 | 9.908  | 23.646 1.00 29.35 |
| ATOM | 1667 | NZ  | LYS | 1070 | 39.444 | 9.436  | 23.439 1.00 35.82 |
| ATOM | 1671 | C   | LYS | 1070 | 44.518 | 13.582 | 20.340 1.00 29.26 |
| ATOM | 1672 | O   | LYS | 1070 | 44.368 | 12.867 | 19.344 1.00 27.81 |
| ATOM | 1673 | N   | TRP | 1071 | 44.862 | 14.865 | 20.260 1.00 27.00 |
| ATOM | 1675 | CA  | TRP | 1071 | 45.086 | 15.550 | 18.995 1.00 27.37 |
| ATOM | 1676 | CB  | TRP | 1071 | 44.191 | 16.827 | 18.882 1.00 20.67 |
| ATOM | 1677 | CG  | TRP | 1071 | 42.724 | 16.551 | 18.545 1.00 20.12 |
| ATOM | 1678 | CD2 | TRP | 1071 | 41.685 | 16.138 | 19.451 1.00 17.97 |
| ATOM | 1679 | CE2 | TRP | 1071 | 40.524 | 15.892 | 18.675 1.00 13.02 |
| ATOM | 1680 | CE3 | TRP | 1071 | 41.628 | 15.944 | 20.838 1.00 23.76 |
| ATOM | 1681 | CD1 | TRP | 1071 | 42.153 | 16.560 | 17.304 1.00 19.50 |
| ATOM | 1682 | NE1 | TRP | 1071 | 40.834 | 16.155 | 17.373 1.00 13.62 |
| ATOM | 1684 | CZ2 | TRP | 1071 | 39.342 | 15.465 | 19.233 1.00 16.22 |
| ATOM | 1685 | CZ3 | TRP | 1071 | 40.439 | 15.511 | 21.396 1.00 20.67 |
| ATOM | 1686 | CH2 | TRP | 1071 | 39.321 | 15.273 | 20.594 1.00 19.47 |
| ATOM | 1687 | C   | TRP | 1071 | 46.523 | 15.961 | 18.889 1.00 26.26 |
| ATOM | 1688 | O   | TRP | 1071 | 46.948 | 16.465 | 17.842 1.00 28.70 |
| ATOM | 1689 | N   | MET | 1072 | 47.278 | 15.713 | 19.959 1.00 24.85 |
| ATOM | 1691 | CA  | MET | 1072 | 48.676 | 16.119 | 20.034 1.00 22.67 |
| ATOM | 1692 | CB  | MET | 1072 | 49.066 | 16.317 | 21.487 1.00 31.30 |
| ATOM | 1693 | CG  | MET | 1072 | 48.328 | 17.416 | 22.229 1.00 34.64 |
| ATOM | 1694 | SD  | MET | 1072 | 48.977 | 17.610 | 23.948 1.00 35.65 |
| ATOM | 1695 | CE  | MET | 1072 | 50.667 | 17.842 | 23.669 1.00 27.97 |
| ATOM | 1696 | C   | MET | 1072 | 49.697 | 15.215 | 19.388 1.00 25.43 |
| ATOM | 1697 | O   | MET | 1072 | 49.798 | 14.029 | 19.729 1.00 21.51 |

FIG. 7(34)

| | | | | | | | |
|---|---|---|---|---|---|---|---|
| ATOM | 1698 | N | ALA | 1073 | 50.545 | 15.800 | 18.547 1.00 25.55 |
| ATOM | 1700 | CA | ALA | 1073 | 51.571 | 15.024 | 17.874 1.00 29.80 |
| ATOM | 1701 | CB | ALA | 1073 | 52.369 | 15.912 | 16.958 1.00 22.65 |
| ATOM | 1702 | C | ALA | 1073 | 52.448 | 14.453 | 18.989 1.00 34.88 |
| ATOM | 1703 | O | ALA | 1073 | 52.431 | 14.970 | 20.115 1.00 39.38 |
| ATOM | 1704 | N | PRO | 1074 | 53.183 | 13.355 | 18.724 1.00 36.01 |
| ATOM | 1705 | CD | PRO | 1074 | 53.087 | 12.450 | 17.570 1.00 31.55 |
| ATOM | 1706 | CA | PRO | 1074 | 54.040 | 12.771 | 19.769 1.00 36.24 |
| ATOM | 1707 | CB | PRO | 1074 | 54.544 | 11.485 | 19.115 1.00 34.34 |
| ATOM | 1708 | CG | PRO | 1074 | 53.415 | 11.137 | 18.193 1.00 31.88 |
| ATOM | 1709 | C | PRO | 1074 | 55.189 | 13.670 | 20.288 1.00 37.13 |
| ATOM | 1710 | O | PRO | 1074 | 55.570 | 13.575 | 21.447 1.00 34.58 |
| ATOM | 1711 | N | GLU | 1075 | 55.746 | 14.533 | 19.440 1.00 37.40 |
| ATOM | 1713 | CA | GLU | 1075 | 56.813 | 15.422 | 19.884 1.00 40.62 |
| ATOM | 1714 | CB | GLU | 1075 | 57.598 | 15.990 | 18.707 1.00 33.55 |
| ATOM | 1715 | CG | GLU | 1075 | 56.853 | 16.957 | 17.844 1.00 39.40 |
| ATOM | 1716 | CD | GLU | 1075 | 55.952 | 16.300 | 16.828 1.00 43.14 |
| ATOM | 1717 | OE1 | GLU | 1075 | 55.965 | 15.055 | 16.720 1.00 49.09 |
| ATOM | 1718 | OE2 | GLU | 1075 | 55.228 | 17.040 | 16.124 1.00 44.63 |
| ATOM | 1719 | C | GLU | 1075 | 56.239 | 16.546 | 20.757 1.00 42.73 |
| ATOM | 1720 | O | GLU | 1075 | 56.903 | 17.061 | 21.639 1.00 44.76 |
| ATOM | 1721 | N | THR | 1076 | 54.982 | 16.888 | 20.524 1.00 46.13 |
| ATOM | 1723 | CA | THR | 1076 | 54.304 | 17.923 | 21.283 1.00 46.22 |
| ATOM | 1724 | CB | THR | 1076 | 52.991 | 18.319 | 20.605 1.00 43.95 |
| ATOM | 1725 | OG1 | THR | 1076 | 53.245 | 18.666 | 19.230 1.00 46.46 |
| ATOM | 1727 | CG2 | THR | 1076 | 52.361 | 19.481 | 21.334 1.00 43.93 |
| ATOM | 1728 | C | THR | 1076 | 53.991 | 17.378 | 22.662 1.00 47.62 |
| ATOM | 1729 | O | THR | 1076 | 54.175 | 18.057 | 23.650 1.00 52.45 |
| ATOM | 1730 | N | ILE | 1077 | 53.442 | 16.173 | 22.717 1.00 47.96 |
| ATOM | 1732 | CA | ILE | 1077 | 53.123 | 15.528 | 23.980 1.00 46.99 |
| ATOM | 1733 | CB | ILE | 1077 | 52.496 | 14.151 | 23.720 1.00 46.43 |
| ATOM | 1734 | CG2 | ILE | 1077 | 52.691 | 13.232 | 24.895 1.00 46.16 |
| ATOM | 1735 | CG1 | ILE | 1077 | 51.024 | 14.306 | 23.384 1.00 44.29 |
| ATOM | 1736 | CD1 | ILE | 1077 | 50.336 | 13.010 | 23.163 1.00 46.43 |
| ATOM | 1737 | C | ILE | 1077 | 54.418 | 15.345 | 24.767 1.00 51.37 |
| ATOM | 1738 | O | ILE | 1077 | 54.473 | 15.577 | 25.974 1.00 52.53 |
| ATOM | 1739 | N | PHE | 1078 | 55.458 | 14.931 | 24.058 1.00 53.41 |
| ATOM | 1741 | CA | PHE | 1078 | 56.750 | 14.696 | 24.672 1.00 58.94 |
| ATOM | 1742 | CB | PHE | 1078 | 57.506 | -13.570 | 23.925 1.00 60.74 |
| ATOM | 1743 | CG | PHE | 1078 | 56.901 | 12.184 | 24.124 1.00 57.84 |

FIG. 7(35)

| | | | | | | | |
|---|---|---|---|---|---|---|---|
| ATOM | 1744 | CD1 | PHE | 1078 | 56.068 | 11.612 | 23.169 1.00 54.09 |
| ATOM | 1745 | CD2 | PHE | 1078 | 57.127 | 11.483 | 25.298 1.00 58.64 |
| ATOM | 1746 | CE1 | PHE | 1078 | 55.478 | 10.380 | 23.381 1.00 53.82 |
| ATOM | 1747 | CE2 | PHE | 1078 | 56.539 | 10.254 | 25.514 1.00 57.20 |
| ATOM | 1748 | CZ | PHE | 1078 | 55.711 | 9.703 | 24.555 1.00 55.07 |
| ATOM | 1749 | C | PHE | 1078 | 57.574 | 15.981 | 24.767 1.00 63.98 |
| ATOM | 1750 | O | PHE | 1078 | 57.433 | 16.738 | 25.736 1.00 67.06 |
| ATOM | 1751 | N | ASP | 1079 | 58.356 | 16.274 | 23.724 1.00 66.97 |
| ATOM | 1753 | CA | ASP | 1079 | 59.215 | 17.472 | 23.678 1.00 68.09 |
| ATOM | 1754 | CB | ASP | 1079 | 60.225 | 17.402 | 22.501 1.00 66.89 |
| ATOM | 1755 | CG | ASP | 1079 | 60.174 | 16.082 | 21.714 1.00 69.02 |
| ATOM | 1756 | OD1 | ASP | 1079 | 60.254 | 16.156 | 20.474 1.00 71.23 |
| ATOM | 1757 | OD2 | ASP | 1079 | 60.089 | 14.980 | 22.308 1.00 69.71 |
| ATOM | 1758 | C | ASP | 1079 | 58.434 | 18.806 | 23.599 1.00 67.74 |
| ATOM | 1759 | O | ASP | 1079 | 59.011 | 19.848 | 23.266 1.00 66.85 |
| ATOM | 1760 | N | ARG | 1080 | 57.137 | 18.747 | 23.926 1.00 68.20 |
| ATOM | 1762 | CA | ARG | 1080 | 56.173 | 19.858 | 23.898 1.00 66.60 |
| ATOM | 1763 | CB | ARG | 1080 | 55.997 | 20.496 | 25.279 1.00 67.64 |
| ATOM | 1764 | CG | ARG | 1080 | 54.529 | 20.758 | 25.638 1.00 71.26 |
| ATOM | 1765 | CD | ARG | 1080 | 53.823 | 19.481 | 26.096 1.00 73.66 |
| ATOM | 1766 | NE | ARG | 1080 | 52.364 | 19.610 | 26.226 1.00 75.75 |
| ATOM | 1768 | CZ | ARG | 1080 | 51.642 | 18.981 | 27.157 1.00 74.86 |
| ATOM | 1769 | NH1 | ARG | 1080 | 50.321 | 19.134 | 27.211 1.00 69.96 |
| ATOM | 1772 | NH2 | ARG | 1080 | 52.247 | 18.212 | 28.060 1.00 72.78 |
| ATOM | 1775 | C | ARG | 1080 | 56.305 | 20.920 | 22.801 1.00 63.93 |
| ATOM | 1776 | O | ARG | 1080 | 55.861 | 22.069 | 22.955 1.00 61.93 |
| ATOM | 1777 | N | VAL | 1081 | 56.863 | 20.510 | 21.667 1.00 61.30 |
| ATOM | 1779 | CA | VAL | 1081 | 57.034 | 21.413 | 20.545 1.00 58.53 |
| ATOM | 1780 | CB | VAL | 1081 | 58.202 | 20.951 | 19.584 1.00 60.54 |
| ATOM | 1781 | CG1 | VAL | 1081 | 59.304 | 20.266 | 20.370 1.00 62.35 |
| ATOM | 1782 | CG2 | VAL | 1081 | 57.701 | 20.043 | 18.455 1.00 55.04 |
| ATOM | 1783 | C | VAL | 1081 | 55.713 | 21.481 | 19.771 1.00 56.90 |
| ATOM | 1784 | O | VAL | 1081 | 55.052 | 20.452 | 19.560 1.00 57.43 |
| ATOM | 1785 | N | TYR | 1082 | 55.287 | 22.699 | 19.435 1.00 51.51 |
| ATOM | 1787 | CA | TYR | 1082 | 54.078 | 22.909 | 18.641 1.00 41.08 |
| ATOM | 1788 | CB | TYR | 1082 | 53.092 | 23.847 | 19.332 1.00 37.59 |
| ATOM | 1789 | CG | TYR | 1082 | 52.275 | 23.238 | 20.442 1.00 32.41 |
| ATOM | 1790 | CD1 | TYR | 1082 | 52.800 | 23.135 | 21.721 1.00 38.13 |
| ATOM | 1791 | CE1 | TYR | 1082 | 52.043 | 22.663 | 22.781 1.00 38.73 |
| ATOM | 1792 | CD2 | TYR | 1082 | 50.961 | 22.843 | 20.234 1.00 27.91 |

FIG. 7(36)

```
ATOM   1793 CE2 TYR 1082      50.189 22.374 21.287 1.00 33.59
ATOM   1794 CZ  TYR 1082      50.739 22.290 22.572 1.00 36.82
ATOM   1795 OH  TYR 1082      50.001 21.874 23.679 1.00 39.60
ATOM   1797 C   TYR 1082      54.591 23.598 17.410 1.00 34.81
ATOM   1798 O   TYR 1082      55.240 24.608 17.545 1.00 33.62
ATOM   1799 N   THR 1083      54.394 22.997 16.236 1.00 34.71
ATOM   1801 CA  THR 1083      54.819 23.573 14.946 1.00 30.90
ATOM   1802 CB  THR 1083      56.106 22.894 14.384 1.00 29.46
ATOM   1803 OG1 THR 1083      55.789 21.598 13.837 1.00 30.18
ATOM   1805 CG2 THR 1083      57.159 22.768 15.486 1.00 21.74
ATOM   1806 C   THR 1083      53.678 23.371 13.946 1.00 27.79
ATOM   1807 O   THR 1083      52.651 22.777 14.293 1.00 28.80
ATOM   1808 N   ILE 1084      53.804 23.869 12.721 1.00 24.37
ATOM   1810 CA  ILE 1084      52.700 23.615 11.797 1.00 27.69
ATOM   1811 CB  ILE 1084      52.739 24.381 10.465 1.00 28.65
ATOM   1812 CG2 ILE 1084      51.450 25.166 10.284 1.00 29.19
ATOM   1813 CG1 ILE 1084      53.977 25.259 10.361 1.00 37.75
ATOM   1814 CD1 ILE 1084      55.235 24.517  9.985 1.00 46.61
ATOM   1815 C   ILE 1084      52.689 22.143 11.459 1.00 26.44
ATOM   1816 O   ILE 1084      51.627 21.589 11.173 1.00 24.29
ATOM   1817 N   GLN 1085      53.861 21.507 11.518 1.00 25.11
ATOM   1819 CA  GLN 1085      53.920 20.097 11.188 1.00 24.39
ATOM   1820 CB  GLN 1085      55.315 19.612 10.823 1.00 27.61
ATOM   1821 CG  GLN 1085      55.753 20.012  9.411 1.00 33.25
ATOM   1822 CD  GLN 1085      54.653 19.826  8.347 1.00 34.07
ATOM   1823 OE1 GLN 1085      53.943 20.779  8.004 1.00 41.60
ATOM   1824 NE2 GLN 1085      54.546 18.632  7.797 1.00 28.88
ATOM   1827 C   GLN 1085      53.296 19.267 12.258 1.00 23.23
ATOM   1828 O   GLN 1085      52.900 18.141 11.981 1.00 25.97
ATOM   1829 N   SER 1086      53.195 19.798 13.480 1.00 20.86
ATOM   1831 CA  SER 1086      52.488 19.040 14.507 1.00 18.08
ATOM   1832 CB  SER 1086      53.044 19.256 15.926 1.00 20.91
ATOM   1833 OG  SER 1086      52.870 20.559 16.440 1.00 21.60
ATOM   1835 C   SER 1086      50.962 19.336 14.353 1.00 20.67
ATOM   1836 O   SER 1086      50.138 18.531 14.806 1.00 13.79
ATOM   1837 N   ASP 1087      50.602 20.415 13.609 1.00 18.68
ATOM   1839 CA  ASP 1087      49.190 20.793 13.324 1.00 11.08
ATOM   1840 CB  ASP 1087      49.038 22.249 12.805 1.00 21.08
ATOM   1841 CG  ASP 1087      48.845 23.287 13.920 1.00 23.79
ATOM   1842 OD1 ASP 1087      49.348 24.407 13.745 1.00 31.01
```

FIG. 7(37)

| | | | | | | | |
|---|---|---|---|---|---|---|---|
| ATOM | 1843 | OD2 | ASP | 1087 | 48.212 | 23.013 | 14.967 1.00 28.91 |
| ATOM | 1844 | C | ASP | 1087 | 48.632 | 19.860 | 12.261 1.00 11.16 |
| ATOM | 1845 | O | ASP | 1087 | 47.406 | 19.640 | 12.177 1.00 12.65 |
| ATOM | 1846 | N | VAL | 1088 | 49.520 | 19.390 | 11.390 1.00 9.61 |
| ATOM | 1848 | CA | VAL | 1088 | 49.181 | 18.404 | 10.345 1.00 13.37 |
| ATOM | 1849 | CB | VAL | 1088 | 50.351 | 18.195 | 9.389 1.00 15.40 |
| ATOM | 1850 | CG1 | VAL | 1088 | 50.057 | 17.067 | 8.486 1.00 14.68 |
| ATOM | 1851 | CG2 | VAL | 1088 | 50.609 | 19.477 | 8.587 1.00 10.67 |
| ATOM | 1852 | C | VAL | 1088 | 48.839 | 17.061 | 11.014 1.00 13.67 |
| ATOM | 1853 | O | VAL | 1088 | 47.897 | 16.387 | 10.618 1.00 15.00 |
| ATOM | 1854 | N | TRP | 1089 | 49.618 | 16.668 | 12.015 1.00 12.30 |
| ATOM | 1856 | CA | TRP | 1089 | 49.301 | 15.460 | 12.748 1.00 12.96 |
| ATOM | 1857 | CB | TRP | 1089 | 50.236 | 15.279 | 13.960 1.00 16.98 |
| ATOM | 1858 | CG | TRP | 1089 | 49.764 | 14.195 | 14.887 1.00 18.14 |
| ATOM | 1859 | CD2 | TRP | 1089 | 50.325 | 12.884 | 15.031 1.00 18.48 |
| ATOM | 1860 | CE2 | TRP | 1089 | 49.476 | 12.162 | 15.893 1.00 20.05 |
| ATOM | 1861 | CE3 | TRP | 1089 | 51.460 | 12.245 | 14.503 1.00 22.61 |
| ATOM | 1862 | CD1 | TRP | 1089 | 48.640 | 14.215 | 15.657 1.00 18.89 |
| ATOM | 1863 | NE1 | TRP | 1089 | 48.451 | 12.995 | 16.255 1.00 19.54 |
| ATOM | 1865 | CZ2 | TRP | 1089 | 49.725 | 10.839 | 16.249 1.00 20.08 |
| ATOM | 1866 | CZ3 | TRP | 1089 | 51.709 | 10.927 | 14.855 1.00 17.00 |
| ATOM | 1867 | CH2 | TRP | 1089 | 50.846 | 10.243 | 15.722 1.00 23.71 |
| ATOM | 1868 | C | TRP | 1089 | 47.873 | 15.711 | 13.207 1.00 14.68 |
| ATOM | 1869 | O | TRP | 1089 | 46.987 | 14.958 | 12.842 1.00 20.33 |
| ATOM | 1870 | N | SER | 1090 | 47.636 | 16.823 | 13.923 1.00 18.59 |
| ATOM | 1872 | CA | SER | 1090 | 46.287 | 17.209 | 14.413 1.00 15.54 |
| ATOM | 1873 | CB | SER | 1090 | 46.297 | 18.603 | 15.043 1.00 12.20 |
| ATOM | 1874 | OG | SER | 1090 | 47.066 | 18.621 | 16.237 1.00 18.86 |
| ATOM | 1876 | C | SER | 1090 | 45.256 | 17.190 | 13.309 1.00 16.50 |
| ATOM | 1877 | O | SER | 1090 | 44.128 | 16.691 | 13.487 1.00 18.14 |
| ATOM | 1878 | N | PHE | 1091 | 45.635 | 17.745 | 12.158 1.00 23.35 |
| ATOM | 1880 | CA | PHE | 1091 | 44.746 | 17.776 | 10.997 1.00 20.78 |
| ATOM | 1881 | CB | PHE | 1091 | 45.445 | 18.399 | 9.786 1.00 17.07 |
| ATOM | 1882 | CG | PHE | 1091 | 44.533 | 18.524 | 8.598 1.00 21.98 |
| ATOM | 1883 | CD1 | PHE | 1091 | 43.396 | 19.347 | 8.666 1.00 17.34 |
| ATOM | 1884 | CD2 | PHE | 1091 | 44.740 | 17.754 | 7.460 1.00 19.42 |
| ATOM | 1885 | CE1 | PHE | 1091 | 42.485 | 19.398 | 7.641 1.00 15.43 |
| ATOM | 1886 | CE2 | PHE | 1091 | 43.829 | 17.792 | 6.421 1.00 18.06 |
| ATOM | 1887 | CZ | PHE | 1091 | 42.693 | 18.618 | 6.509 1.00 19.76 |
| ATOM | 1888 | C | PHE | 1091 | 44.306 | 16.332 | 10.667 1.00 17.25 |

FIG. 7(38)

| | | | | | | | |
|---|---|---|---|---|---|---|---|
| ATOM | 1889 | O | PHE | 1091 | 43.147 | 16.077 | 10.334 1.00 15.79 |
| ATOM | 1890 | N | GLY | 1092 | 45.258 | 15.408 | 10.812 1.00 19.49 |
| ATOM | 1892 | CA | GLY | 1092 | 45.042 | 13.988 | 10.577 1.00 18.11 |
| ATOM | 1893 | C | GLY | 1092 | 44.029 | 13.429 | 11.544 1.00 19.35 |
| ATOM | 1894 | O | GLY | 1092 | 43.235 | 12.581 | 11.137 1.00 24.23 |
| ATOM | 1895 | N | VAL | 1093 | 44.073 | 13.836 | 12.819 1.00 18.53 |
| ATOM | 1897 | CA | VAL | 1093 | 43.055 | 13.392 | 13.788 1.00 20.09 |
| ATOM | 1898 | CB | VAL | 1093 | 43.389 | 13.752 | 15.298 1.00 15.18 |
| ATOM | 1899 | CG1 | VAL | 1093 | 42.421 | 13.051 | 16.187 1.00 17.08 |
| ATOM | 1900 | CG2 | VAL | 1093 | 44.778 | 13.310 | 15.698 1.00 11.27 |
| ATOM | 1901 | C | VAL | 1093 | 41.661 | 13.971 | 13.376 1.00 22.42 |
| ATOM | 1902 | O | VAL | 1093 | 40.649 | 13.253 | 13.396 1.00 26.19 |
| ATOM | 1903 | N | LEU | 1094 | 41.618 | 15.235 | 12.938 1.00 23.95 |
| ATOM | 1905 | CA | LEU | 1094 | 40.363 | 15.893 | 12.484 1.00 19.63 |
| ATOM | 1906 | CB | LEU | 1094 | 40.667 | 17.338 | 12.050 1.00 25.24 |
| ATOM | 1907 | CG | LEU | 1094 | 39.587 | 18.420 | 11.974 1.00 27.30 |
| ATOM | 1908 | CD1 | LEU | 1094 | 40.136 | 19.497 | 11.113 1.00 28.26 |
| ATOM | 1909 | CD2 | LEU | 1094 | 38.265 | 17.929 | 11.385 1.00 27.54 |
| ATOM | 1910 | C | LEU | 1094 | 39.775 | 15.146 | 11.280 1.00 16.12 |
| ATOM | 1911 | O | LEU | 1094 | 38.555 | 15.002 | 11.129 1.00 16.14 |
| ATOM | 1912 | N | LEU | 1095 | 40.631 | 14.766 | 10.348 1.00 16.30 |
| ATOM | 1914 | CA | LEU | 1095 | 40.155 | 14.003 | 9.195 1.00 17.98 |
| ATOM | 1915 | CB | LEU | 1095 | 41.321 | 13.538 | 8.317 1.00 16.52 |
| ATOM | 1916 | CG | LEU | 1095 | 41.981 | 14.536 | 7.386 1.00 14.88 |
| ATOM | 1917 | CD1 | LEU | 1095 | 42.807 | 13.734 | 6.399 1.00 11.81 |
| ATOM | 1918 | CD2 | LEU | 1095 | 40.931 | 15.401 | 6.639 1.00 21.08 |
| ATOM | 1919 | C | LEU | 1095 | 39.437 | 12.770 | 9.722 1.00 17.52 |
| ATOM | 1920 | O | LEU | 1095 | 38.324 | 12.448 | 9.270 1.00 16.23 |
| ATOM | 1921 | N | TRP | 1096 | 40.077 | 12.105 | 10.697 1.00 14.50 |
| ATOM | 1923 | CA | TRP | 1096 | 39.509 | 10.916 | 11.304 1.00 14.02 |
| ATOM | 1924 | CB | TRP | 1096 | 40.452 | 10.330 | 12.337 1.00 13.21 |
| ATOM | 1925 | CG | TRP | 1096 | 40.010 | 8.992 | 12.850 1.00 18.93 |
| ATOM | 1926 | CD2 | TRP | 1096 | 39.016 | 8.732 | 13.856 1.00 24.77 |
| ATOM | 1927 | CE2 | TRP | 1096 | 38.952 | 7.319 | 14.020 1.00 27.07 |
| ATOM | 1928 | CE3 | TRP | 1096 | 38.178 | 9.546 | 14.647 1.00 29.39 |
| ATOM | 1929 | CD1 | TRP | 1096 | 40.483 | 7.781 | 12.460 1.00 21.28 |
| ATOM | 1930 | NE1 | TRP | 1096 | 39.854 | 6.770 | 13.154 1.00 18.61 |
| ATOM | 1932 | CZ2 | TRP | 1096 | 38.075 | 6.700 | 14.954 1.00 28.21 |
| ATOM | 1933 | CZ3 | TRP | 1096 | 37.303 | 8.927 | 15.581 1.00 29.42 |
| ATOM | 1934 | CH2 | TRP | 1096 | 37.266 | 7.511 | 15.719 1.00 27.60 |

FIG. 7(39)

| | | | | | | | | |
|---|---|---|---|---|---|---|---|---|
| ATOM | 1935 | C | TRP | 1096 | 38.159 | 11.236 | 11.927 | 1.00 18.94 |
| ATOM | 1936 | O | TRP | 1096 | 37.212 | 10.439 | 11.826 | 1.00 22.31 |
| ATOM | 1937 | N | GLU | 1097 | 38.046 | 12.385 | 12.592 | 1.00 23.97 |
| ATOM | 1939 | CA | GLU | 1097 | 36.754 | 12.750 | 13.195 | 1.00 21.61 |
| ATOM | 1940 | CB | GLU | 1097 | 36.823 | 14.012 | 14.041 | 1.00 26.60 |
| ATOM | 1941 | CG | GLU | 1097 | 37.880 | 14.065 | 15.109 | 1.00 21.55 |
| ATOM | 1942 | CD | GLU | 1097 | 37.795 | 15.380 | 15.800 | 1.00 23.56 |
| ATOM | 1943 | OE1 | GLU | 1097 | 36.726 | 15.591 | 16.393 | 1.00 21.97 |
| ATOM | 1944 | OE2 | GLU | 1097 | 38.741 | 16.208 | 15.706 | 1.00 20.79 |
| ATOM | 1945 | C | GLU | 1097 | 35.744 | 13.010 | 12.116 | 1.00 19.15 |
| ATOM | 1946 | O | GLU | 1097 | 34.549 | 12.766 | 12.304 | 1.00 28.35 |
| ATOM | 1947 | N | ILE | 1098 | 36.190 | 13.565 | 11.001 | 1.00 17.99 |
| ATOM | 1949 | CA | ILE | 1098 | 35.244 | 13.821 | 9.915 | 1.00 17.98 |
| ATOM | 1950 | CB | ILE | 1098 | 35.862 | 14.650 | 8.732 | 1.00 13.59 |
| ATOM | 1951 | CG2 | ILE | 1098 | 34.880 | 14.725 | 7.568 | 1.00 13.47 |
| ATOM | 1952 | CG1 | ILE | 1098 | 36.169 | 16.074 | 9.181 | 1.00 11.46 |
| ATOM | 1953 | CD1 | ILE | 1098 | 36.691 | 16.960 | 8.074 | 1.00 9.72 |
| ATOM | 1954 | C | ILE | 1098 | 34.645 | 12.529 | 9.372 | 1.00 16.07 |
| ATOM | 1955 | O | ILE | 1098 | 33.444 | 12.445 | 9.171 | 1.00 18.22 |
| ATOM | 1956 | N | PHE | 1099 | 35.460 | 11.499 | 9.171 | 1.00 20.11 |
| ATOM | 1958 | CA | PHE | 1099 | 34.925 | 10.257 | 8.601 | 1.00 18.95 |
| ATOM | 1959 | CB | PHE | 1099 | 35.909 | 9.660 | 7.625 | 1.00 16.86 |
| ATOM | 1960 | CG | PHE | 1099 | 36.269 | 10.584 | 6.517 | 1.00 12.61 |
| ATOM | 1961 | CD1 | PHE | 1099 | 37.308 | 11.468 | 6.671 | 1.00 14.37 |
| ATOM | 1962 | CD2 | PHE | 1099 | 35.522 | 10.624 | 5.362 | 1.00 18.03 |
| ATOM | 1963 | CE1 | PHE | 1099 | 37.595 | 12.369 | 5.717 | 1.00 13.66 |
| ATOM | 1964 | CE2 | PHE | 1099 | 35.811 | 11.553 | 4.378 | 1.00 16.05 |
| ATOM | 1965 | CZ | PHE | 1099 | 36.843 | 12.418 | 4.568 | 1.00 17.86 |
| ATOM | 1966 | C | PHE | 1099 | 34.368 | 9.201 | 9.551 | 1.00 23.18 |
| ATOM | 1967 | O | PHE | 1099 | 34.111 | 8.070 | 9.149 | 1.00 22.90 |
| ATOM | 1968 | N | SER | 1100 | 34.274 | 9.553 | 10.825 | 1.00 26.68 |
| ATOM | 1970 | CA | SER | 1100 | 33.652 | 8.690 | 11.820 | 1.00 24.51 |
| ATOM | 1971 | CB | SER | 1100 | 34.504 | 8.572 | 13.079 | 1.00 25.60 |
| ATOM | 1972 | OG | SER | 1100 | 34.826 | 9.842 | 13.625 | 1.00 29.76 |
| ATOM | 1974 | C | SER | 1100 | 32.398 | 9.465 | 12.145 | 1.00 26.92 |
| ATOM | 1975 | O | SER | 1100 | 31.765 | 9.211 | 13.157 | 1.00 31.32 |
| ATOM | 1976 | N | LEU | 1101 | 32.018 | 10.387 | 11.251 | 1.00 28.15 |
| ATOM | 1978 | CA | LEU | 1101 | 30.860 | 11.241 | 11.453 | 1.00 24.97 |
| ATOM | 1979 | CB | LEU | 1101 | 29.556 | 10.557 | 11.015 | 1.00 22.00 |
| ATOM | 1980 | CG | LEU | 1101 | 29.423 | 10.410 | 9.495 | 1.00 25.66 |

FIG. 7(40)

| ATOM | 1981 | CD1 | LEU | 1101 | 28.060 | 9.866  | 9.127  | 1.00 | 22.23 |
|------|------|-----|-----|------|--------|--------|--------|------|-------|
| ATOM | 1982 | CD2 | LEU | 1101 | 29.632 | 11.768 | 8.829  | 1.00 | 32.30 |
| ATOM | 1983 | C   | LEU | 1101 | 30.771 | 11.779 | 12.888 | 1.00 | 26.64 |
| ATOM | 1984 | O   | LEU | 1101 | 29.793 | 11.552 | 13.580 | 1.00 | 31.34 |
| ATOM | 1985 | N   | GLY | 1102 | 31.828 | 12.446 | 13.336 | 1.00 | 24.93 |
| ATOM | 1987 | CA  | GLY | 1102 | 31.836 | 13.057 | 14.650 | 1.00 | 28.61 |
| ATOM | 1988 | C   | GLY | 1102 | 32.129 | 12.293 | 15.917 | 1.00 | 32.38 |
| ATOM | 1989 | O   | GLY | 1102 | 31.647 | 12.693 | 16.950 | 1.00 | 35.69 |
| ATOM | 1990 | N   | ALA | 1103 | 33.004 | 11.291 | 15.876 | 1.00 | 35.95 |
| ATOM | 1992 | CA  | ALA | 1103 | 33.354 | 10.500 | 17.060 | 1.00 | 31.27 |
| ATOM | 1993 | CB  | ALA | 1103 | 33.515 | 9.041  | 16.672 | 1.00 | 36.15 |
| ATOM | 1994 | C   | ALA | 1103 | 34.625 | 10.972 | 17.747 | 1.00 | 34.29 |
| ATOM | 1995 | O   | ALA | 1103 | 35.382 | 11.788 | 17.190 | 1.00 | 36.92 |
| ATOM | 1996 | N   | SER | 1104 | 34.886 | 10.417 | 18.934 | 1.00 | 33.11 |
| ATOM | 1998 | CA  | SER | 1104 | 36.087 | 10.744 | 19.715 | 1.00 | 35.13 |
| ATOM | 1999 | CB  | SER | 1104 | 35.906 | 10.422 | 21.207 | 1.00 | 38.40 |
| ATOM | 2000 | OG  | SER | 1104 | 34.719 | 10.964 | 21.765 | 1.00 | 50.36 |
| ATOM | 2002 | C   | SER | 1104 | 37.216 | 9.852  | 19.249 | 1.00 | 34.54 |
| ATOM | 2003 | O   | SER | 1104 | 37.039 | 8.640  | 19.167 | 1.00 | 33.44 |
| ATOM | 2004 | N   | PRO | 1105 | 38.395 | 10.434 | 18.963 | 1.00 | 32.93 |
| ATOM | 2005 | CD  | PRO | 1105 | 38.678 | 11.877 | 18.972 | 1.00 | 31.54 |
| ATOM | 2006 | CA  | PRO | 1105 | 39.571 | 9.693  | 18.513 | 1.00 | 29.88 |
| ATOM | 2007 | CB  | PRO | 1105 | 40.633 | 10.781 | 18.465 | 1.00 | 22.24 |
| ATOM | 2008 | CG  | PRO | 1105 | 39.883 | 11.965 | 18.079 | 1.00 | 28.04 |
| ATOM | 2009 | C   | PRO | 1105 | 39.919 | 8.659  | 19.582 | 1.00 | 32.54 |
| ATOM | 2010 | O   | PRO | 1105 | 39.480 | 8.795  | 20.731 | 1.00 | 28.79 |
| ATOM | 2011 | N   | TYR | 1106 | 40.700 | 7.648  | 19.196 | 1.00 | 34.52 |
| ATOM | 2013 | CA  | TYR | 1106 | 41.148 | 6.564  | 20.085 | 1.00 | 39.62 |
| ATOM | 2014 | CB  | TYR | 1106 | 42.374 | 6.994  | 20.896 | 1.00 | 37.66 |
| ATOM | 2015 | CG  | TYR | 1106 | 43.496 | 7.566  | 20.059 | 1.00 | 39.50 |
| ATOM | 2016 | CD1 | TYR | 1106 | 43.690 | 8.957  | 19.976 | 1.00 | 37.50 |
| ATOM | 2017 | CE1 | TYR | 1106 | 44.655 | 9.518  | 19.143 | 1.00 | 35.61 |
| ATOM | 2018 | CD2 | TYR | 1106 | 44.315 | 6.739  | 19.293 | 1.00 | 34.54 |
| ATOM | 2019 | CE2 | TYR | 1106 | 45.305 | 7.290  | 18.446 | 1.00 | 38.80 |
| ATOM | 2020 | CZ  | TYR | 1106 | 45.466 | 8.686  | 18.373 | 1.00 | 38.23 |
| ATOM | 2021 | OH  | TYR | 1106 | 46.412 | 9.240  | 17.520 | 1.00 | 31.37 |
| ATOM | 2023 | C   | TYR | 1106 | 40.022 | 6.128  | 21.016 | 1.00 | 47.24- |
| ATOM | 2024 | O   | TYR | 1106 | 40.100 | 6.296  | 22.247 | 1.00 | 46.94 |
| ATOM | 2025 | N   | PRO | 1107 | 38.947 | 5.570  | 20.431 | 1.00 | 52.30 |
| ATOM | 2026 | CD  | PRO | 1107 | 38.880 | 5.234  | 18.996 | 1.00 | 52.76 |

FIG. 7(41)

| | | | | | | | |
|---|---|---|---|---|---|---|---|
| ATOM | 2027 | CA | PRO | 1107 | 37.750 | 5.088 21.125 | 1.00 55.67 |
| ATOM | 2028 | CB | PRO | 1107 | 37.078 | 4.223 20.066 | 1.00 55.09 |
| ATOM | 2029 | CG | PRO | 1107 | 37.420 | 4.931 18.797 | 1.00 52.62 |
| ATOM | 2030 | C | PRO | 1107 | 38.035 | 4.300 22.408 | 1.00 60.55 |
| ATOM | 2031 | O | PRO | 1107 | 38.668 | 3.231 22.377 | 1.00 60.88 |
| ATOM | 2032 | N | GLY | 1108 | 37.631 | 4.894 23.533 | 1.00 62.85 |
| ATOM | 2034 | CA | GLY | 1108 | 37.790 | 4.284 24.845 | 1.00 63.10 |
| ATOM | 2035 | C | GLY | 1108 | 39.171 | 3.783 25.228 | 1.00 61.44 |
| ATOM | 2036 | O | GLY | 1108 | 39.319 | 3.010 26.178 | 1.00 63.49 |
| ATOM | 2037 | N | VAL | 1109 | 40.181 | 4.228 24.498 | 1.00 58.31 |
| ATOM | 2039 | CA | VAL | 1109 | 41.548 | 3.835 24.766 | 1.00 55.54 |
| ATOM | 2040 | CB | VAL | 1109 | 42.430 | 4.181 23.580 | 1.00 54.11 |
| ATOM | 2041 | CG1 | VAL | 1109 | 43.857 | 3.787 23.857 | 1.00 51.33 |
| ATOM | 2042 | CG2 | VAL | 1109 | 41.875 | 3.528 22.306 | 1.00 54.09 |
| ATOM | 2043 | C | VAL | 1109 | 42.006 | 4.657 25.949 | 1.00 57.04 |
| ATOM | 2044 | O | VAL | 1109 | 41.492 | 5.749 26.163 | 1.00 57.18 |
| ATOM | 2045 | N | LYS | 1110 | 42.969 | 4.140 26.711 | 1.00 59.43 |
| ATOM | 2047 | CA | LYS | 1110 | 43.497 | 4.849 27.880 | 1.00 60.27 |
| ATOM | 2048 | CB | LYS | 1110 | 43.928 | 3.842 28.936 | 1.00 63.70 |
| ATOM | 2049 | C | LYS | 1110 | 44.664 | 5.796 27.538 | 1.00 60.52 |
| ATOM | 2050 | O | LYS | 1110 | 45.570 | 5.410 26.780 | 1.00 61.06 |
| ATOM | 2051 | N | ILE | 1111 | 44.665 | 7.006 28.115 | 1.00 58.79 |
| ATOM | 2053 | CA | ILE | 1111 | 45.732 | 7.987 27.859 | 1.00 60.01 |
| ATOM | 2054 | CB | ILE | 1111 | 45.236 | 9.441 27.886 | 1.00 63.41 |
| ATOM | 2055 | CG2 | ILE | 1111 | 44.517 | 9.798 26.596 | 1.00 58.31 |
| ATOM | 2056 | CG1 | ILE | 1111 | 44.413 | 9.688 29.145 | 1.00 69.87 |
| ATOM | 2057 | CD1 | ILE | 1111 | 44.341 | 11.144 29.528 | 1.00 75.64 |
| ATOM | 2058 | C | ILE | 1111 | 46.949 | 7.891 28.781 | 1.00 58.91 |
| ATOM | 2059 | O | ILE | 1111 | 47.670 | 8.862 28.992 | 1.00 59.56 |
| ATOM | 2060 | N | ASP | 1112 | 47.187 | 6.697 29.299 | 1.00 60.43 |
| ATOM | 2062 | CA | ASP | 1112 | 48.312 | 6.407 30.173 | 1.00 56.25 |
| ATOM | 2063 | CB | ASP | 1112 | 48.318 | 4.919 30.421 | 1.00 59.88 |
| ATOM | 2064 | CG | ASP | 1112 | 48.273 | 4.131 29.122 | 1.00 67.87 |
| ATOM | 2065 | OD1 | ASP | 1112 | 47.179 | 3.893 28.564 | 1.00 71.34 |
| ATOM | 2066 | OD2 | ASP | 1112 | 49.348 | 3.765 28.628 | 1.00 72.11 |
| ATOM | 2067 | C | ASP | 1112 | 49.612 | 6.795 29.489 | 1.00 54.37 |
| ATOM | 2068 | O | ASP | 1112 | 49.634 | 7.066 28.284 | 1.00 50.67 |
| ATOM | 2069 | N | GLU | 1113 | 50.710 | 6.741 30.236 | 1.00 55.36 |
| ATOM | 2071 | CA | GLU | 1113 | 52.024 | 7.089 29.683 | 1.00 55.99 |
| ATOM | 2072 | CB | GLU | 1113 | 53.051 | 7.374 30.806 | 1.00 58.69 |

FIG. 7(42)

| | | | | | | | | |
|---|---|---|---|---|---|---|---|---|
| ATOM | 2073 | C | GLU | 1113 | 52.552 | 6.015 | 28.726 | 1.00 54.42 |
| ATOM | 2074 | O | GLU | 1113 | 53.624 | 6.175 | 28.126 | 1.00 51.91 |
| ATOM | 2075 | N | GLU | 1114 | 51.822 | 4.903 | 28.627 | 1.00 51.54 |
| ATOM | 2077 | CA | GLU | 1114 | 52.192 | 3.819 | 27.719 | 1.00 54.36 |
| ATOM | 2078 | CB | GLU | 1114 | 51.873 | 2.452 | 28.322 | 1.00 56.43 |
| ATOM | 2079 | CG | GLU | 1114 | 53.072 | 1.749 | 28.948 | 1.00 63.29 |
| ATOM | 2080 | CD | GLU | 1114 | 53.996 | 2.661 | 29.772 | 1.00 67.36 |
| ATOM | 2081 | OE1 | GLU | 1114 | 55.153 | 2.870 | 29.329 | 1.00 67.34 |
| ATOM | 2082 | OE2 | GLU | 1114 | 53.590 | 3.127 | 30.873 | 1.00 68.20 |
| ATOM | 2083 | C | GLU | 1114 | 51.440 | 4.031 | 26.412 | 1.00 52.22 |
| ATOM | 2084 | O | GLU | 1114 | 51.830 | 3.514 | 25.360 | 1.00 51.74 |
| ATOM | 2085 | N | PHE | 1115 | 50.383 | 4.840 | 26.486 | 1.00 49.67 |
| ATOM | 2087 | CA | PHE | 1115 | 49.603 | 5.175 | 25.320 | 1.00 44.59 |
| ATOM | 2088 | CB | PHE | 1115 | 48.400 | 6.013 | 25.688 | 1.00 44.73 |
| ATOM | 2089 | CG | PHE | 1115 | 47.918 | 6.890 | 24.579 | 1.00 49.93 |
| ATOM | 2090 | CD1 | PHE | 1115 | 48.140 | 8.270 | 24.621 | 1.00 50.02 |
| ATOM | 2091 | CD2 | PHE | 1115 | 47.251 | 6.344 | 23.477 | 1.00 53.38 |
| ATOM | 2092 | CE1 | PHE | 1115 | 47.704 | 9.098 | 23.577 | 1.00 52.88 |
| ATOM | 2093 | CE2 | PHE | 1115 | 46.805 | 7.158 | 22.425 | 1.00 51.00 |
| ATOM | 2094 | CZ | PHE | 1115 | 47.033 | 8.535 | 22.474 | 1.00 54.64 |
| ATOM | 2095 | C | PHE | 1115 | 50.582 | 5.981 | 24.507 | 1.00 46.08 |
| ATOM | 2096 | O | PHE | 1115 | 50.929 | 5.572 | 23.402 | 1.00 47.48 |
| ATOM | 2097 | N | CYS | 1116 | 51.127 | 7.047 | 25.101 | 1.00 43.91 |
| ATOM | 2099 | CA | CYS | 1116 | 52.109 | 7.898 | 24.404 | 1.00 45.79 |
| ATOM | 2100 | CB | CYS | 1116 | 52.473 | 9.113 | 25.247 | 1.00 44.47 |
| ATOM | 2101 | SG | CYS | 1116 | 51.129 | 9.723 | 26.295 | 1.00 64.10 |
| ATOM | 2102 | C | CYS | 1116 | 53.392 | 7.140 | 24.019 | 1.00 46.03 |
| ATOM | 2103 | O | CYS | 1116 | 54.232 | 7.667 | 23.279 | 1.00 46.86 |
| ATOM | 2104 | N | ARG | 1117 | 53.536 | 5.911 | 24.529 | 1.00 44.91 |
| ATOM | 2106 | CA | ARG | 1117 | 54.688 | 5.069 | 24.237 | 1.00 41.89 |
| ATOM | 2107 | CB | ARG | 1117 | 54.882 | 4.001 | 25.308 | 1.00 43.78 |
| ATOM | 2108 | CG | ARG | 1117 | 56.237 | 3.298 | 25.233 | 1.00 45.19 |
| ATOM | 2109 | CD | ARG | 1117 | 56.189 | 1.905 | 25.856 | 1.00 47.09 |
| ATOM | 2110 | NE | ARG | 1117 | 55.490 | 0.922 | 25.021 | 1.00 49.55 |
| ATOM | 2112 | CZ | ARG | 1117 | 54.329 | 0.337 | 25.336 | 1.00 51.59 |
| ATOM | 2113 | NH1 | ARG | 1117 | 53.783 | -0.547 | 24.506 | 1.00 51.49 |
| ATOM | 2116 | NH2 | ARG | 1117 | 53.695 | 0.649 | 26.461 | 1.00 47.17 |
| ATOM | 2119 | C | ARG | 1117 | 54.370 | 4.389 | 22.927 | 1.00 38.98 |
| ATOM | 2120 | O | ARG | 1117 | 55.156 | 4.455 | 21.996 | 1.00 42.49 |
| ATOM | 2121 | N | ARG | 1118 | 53.206 | 3.751 | 22.860 | 1.00 35.52 |

FIG. 7(43)

| | | | | | | | |
|---|---|---|---|---|---|---|---|
| ATOM | 2123 | CA | ARG | 1118 | 52.745 | 3.072 | 21.649 1.00 36.78 |
| ATOM | 2124 | CB | ARG | 1118 | 51.330 | 2.559 | 21.880 1.00 31.14 |
| ATOM | 2125 | CG | ARG | 1118 | 51.216 | 1.675 | 23.068 1.00 34.41 |
| ATOM | 2126 | CD | ARG | 1118 | 49.766 | 1.587 | 23.535 1.00 45.83 |
| ATOM | 2127 | NE | ARG | 1118 | 48.897 | 0.750 | 22.693 1.00 53.41 |
| ATOM | 2129 | CZ | ARG | 1118 | 47.564 | 0.658 | 22.826 1.00 55.58 |
| ATOM | 2130 | NH1 | ARG | 1118 | 46.862 | -0.144 | 22.025 1.00 56.70 |
| ATOM | 2133 | NH2 | ARG | 1118 | 46.921 | 1.380 | 23.745 1.00 55.55 |
| ATOM | 2136 | C | ARG | 1118 | 52.742 | 4.067 | 20.471 1.00 38.92 |
| ATOM | 2137 | O | ARG | 1118 | 53.331 | 3.835 | 19.400 1.00 38.28 |
| ATOM | 2138 | N | LEU | 1119 | 52.063 | 5.186 | 20.711 1.00 40.67 |
| ATOM | 2140 | CA | LEU | 1119 | 51.912 | 6.295 | 19.779 1.00 36.71 |
| ATOM | 2141 | CB | LEU | 1119 | 51.192 | 7.416 | 20.540 1.00 32.46 |
| ATOM | 2142 | CG | LEU | 1119 | 50.238 | 8.508 | 20.049 1.00 25.91 |
| ATOM | 2143 | CD1 | LEU | 1119 | 51.047 | 9.651 | 19.564 1.00 19.62 |
| ATOM | 2144 | CD2 | LEU | 1119 | 49.250 | 7.993 | 19.024 1.00 22.26 |
| ATOM | 2145 | C | LEU | 1119 | 53.301 | 6.728 | 19.245 1.00 38.89 |
| ATOM | 2146 | O | LEU | 1119 | 53.469 | 6.960 | 18.047 1.00 43.59 |
| ATOM | 2147 | N | LYS | 1120 | 54.315 | 6.771 | 20.099 1.00 42.22 |
| ATOM | 2149 | CA | LYS | 1120 | 55.649 | 7.152 | 19.640 1.00 41.56 |
| ATOM | 2150 | CB | LYS | 1120 | 56.523 | 7.548 | 20.813 1.00 42.85 |
| ATOM | 2151 | CG | LYS | 1120 | 57.467 | 8.670 | 20.467 1.00 52.51 |
| ATOM | 2152 | CD | LYS | 1120 | 58.407 | 8.989 | 21.620 1.00 60.23 |
| ATOM | 2153 | CE | LYS | 1120 | 59.298 | 10.206 | 21.321 1.00 69.72 |
| ATOM | 2154 | NZ | LYS | 1120 | 58.605 | 11.557 | 21.283 1.00 76.23 |
| ATOM | 2158 | C | LYS | 1120 | 56.351 | 6.050 | 18.825 1.00 43.73 |
| ATOM | 2159 | O | LYS | 1120 | 57.287 | 6.342 | 18.073 1.00 47.49 |
| ATOM | 2160 | N | GLU | 1121 | 55.892 | 4.800 | 18.966 1.00 43.94 |
| ATOM | 2162 | CA | GLU | 1121 | 56.453 | 3.636 | 18.262 1.00 41.07 |
| ATOM | 2163 | CB | GLU | 1121 | 56.415 | 2.395 | 19.147 1.00 48.40 |
| ATOM | 2164 | CG | GLU | 1121 | 57.553 | 2.283 | 20.112 1.00 58.39 |
| ATOM | 2165 | CD | GLU | 1121 | 57.183 | 1.451 | 21.309 1.00 64.79 |
| ATOM | 2166 | OE1 | GLU | 1121 | 56.403 | 0.483 | 21.119 1.00 67.43 |
| ATOM | 2167 | OE2 | GLU | 1121 | 57.657 | 1.778 | 22.431 1.00 67.24 |
| ATOM | 2168 | C | GLU | 1121 | 55.739 | 3.284 | 16.968 1.00 39.16 |
| ATOM | 2169 | O | GLU | 1121 | 56.224 | 2.423 | 16.216 1.00 39.90 |
| ATOM | 2170 | N | GLY | 1122 | 54.525 | 3.805 | 16.781 1.00 31.72 |
| ATOM | 2172 | CA | GLY | 1122 | 53.838 | 3.550 | 15.531 1.00 22.36 |
| ATOM | 2173 | C | GLY | 1122 | 52.427 | 3.064 | 15.646 1.00 19.85 |
| ATOM | 2174 | O | GLY | 1122 | 51.791 | 2.779 | 14.633 1.00 18.01 |

FIG. 7(44)

| | | | | | | | | |
|---|---|---|---|---|---|---|---|---|
| ATOM | 2175 | N | THR | 1123 | 51.918 | 2.946 | 16.860 | 1.00 16.84 |
| ATOM | 2177 | CA | THR | 1123 | 50.535 | 2.502 | 16.989 | 1.00 22.17 |
| ATOM | 2178 | CB | THR | 1123 | 50.209 | 2.144 | 18.469 | 1.00 29.75 |
| ATOM | 2179 | OG1 | THR | 1123 | 51.148 | 1.174 | 18.971 | 1.00 31.60 |
| ATOM | 2181 | CG2 | THR | 1123 | 48.794 | 1.587 | 18.591 | 1.00 31.44 |
| ATOM | 2182 | C | THR | 1123 | 49.653 | 3.673 | 16.453 | 1.00 23.74 |
| ATOM | 2183 | O | THR | 1123 | 49.940 | 4.850 | 16.721 | 1.00 18.73 |
| ATOM | 2184 | N | ARG | 1124 | 48.597 | 3.354 | 15.701 | 1.00 22.93 |
| ATOM | 2186 | CA | ARG | 1124 | 47.735 | 4.379 | 15.125 | 1.00 17.39 |
| ATOM | 2187 | CB | ARG | 1124 | 48.094 | 4.680 | 13.670 | 1.00 17.70 |
| ATOM | 2188 | CG | ARG | 1124 | 49.478 | 5.192 | 13.406 | 1.00 14.57 |
| ATOM | 2189 | CD | ARG | 1124 | 49.713 | 6.484 | 14.040 | 1.00 14.31 |
| ATOM | 2190 | NE | ARG | 1124 | 51.046 | 6.935 | 13.684 | 1.00 10.98 |
| ATOM | 2192 | CZ | ARG | 1124 | 52.067 | 6.988 | 14.533 | 1.00 16.02 |
| ATOM | 2193 | NH1 | ARG | 1124 | 51.861 | 6.604 | 15.775 | 1.00 10.96 |
| ATOM | 2196 | NH2 | ARG | 1124 | 53.269 | 7.468 | 14.163 | 1.00 8.74 |
| ATOM | 2199 | C | ARG | 1124 | 46.317 | 3.893 | 15.096 | 1.00 16.31 |
| ATOM | 2200 | O | ARG | 1124 | 46.085 | 2.698 | 15.022 | 1.00 20.38 |
| ATOM | 2201 | N | MET | 1125 | 45.380 | 4.847 | 15.081 | 1.00 21.15 |
| ATOM | 2203 | CA | MET | 1125 | 43.943 | 4.570 | 15.023 | 1.00 23.81 |
| ATOM | 2204 | CB | MET | 1125 | 43.158 | 5.870 | 15.012 | 1.00 16.88 |
| ATOM | 2205 | CG | MET | 1125 | 42.783 | 6.397 | 16.380 | 1.00 17.08 |
| ATOM | 2206 | SD | MET | 1125 | 41.656 | 7.825 | 16.270 | 1.00 25.19 |
| ATOM | 2207 | CE | MET | 1125 | 42.908 | 9.123 | 15.776 | 1.00 17.02 |
| ATOM | 2208 | C | MET | 1125 | 43.604 | 3.789 | 13.749 | 1.00 29.80 |
| ATOM | 2209 | O | MET | 1125 | 44.298 | 3.923 | 12.748 | 1.00 33.37 |
| ATOM | 2210 | N | ARG | 1126 | 42.576 | 2.953 | 13.806 | 1.00 36.07 |
| ATOM | 2212 | CA | ARG | 1126 | 42.116 | 2.183 | 12.668 | 1.00 36.36 |
| ATOM | 2213 | CB | ARG | 1126 | 41.465 | 0.859 | 13.154 | 1.00 40.10 |
| ATOM | 2214 | CG | ARG | 1126 | 40.257 | 1.021 | 14.061 | 1.00 54.46 |
| ATOM | 2215 | CD | ARG | 1126 | 38.956 | 1.268 | 13.263 | 1.00 65.08 |
| ATOM | 2216 | NE | ARG | 1126 | 37.839 | 1.758 | 14.091 | 1.00 72.39 |
| ATOM | 2218 | CZ | ARG | 1126 | 36.545 | 1.753 | 13.740 | 1.00 74.53 |
| ATOM | 2219 | NH1 | ARG | 1126 | 35.636 | 2.233 | 14.588 | 1.00 78.72 |
| ATOM | 2222 | NH2 | ARG | 1126 | 36.140 | 1.267 | 12.562 | 1.00 74.28 |
| ATOM | 2225 | C | ARG | 1126 | 41.124 | 3.094 | 11.888 | 1.00 32.52 |
| ATOM | 2226 | O | ARG | 1126 | 40.706 | 4.117 | 12.380 | 1.00 34.88 |
| ATOM | 2227 | N | ALA | 1127 | 40.760 | 2.725 | 10.676 | 1.00 29.80 |
| ATOM | 2229 | CA | ALA | 1127 | 39.888 | 3.508 | 9.812 | 1.00 29.83 |
| ATOM | 2230 | CB | ALA | 1127 | 39.743 | 2.782 | 8.460 | 1.00 32.24 |

FIG. 7(45)

| | | | | | | | |
|---|---|---|---|---|---|---|---|
| ATOM | 2231 | C | ALA | 1127 | 38.518 | 3.697 | 10.415 1.00 34.29 |
| ATOM | 2232 | O | ALA | 1127 | 37.944 | 2.727 | 10.881 1.00 39.95 |
| ATOM | 2233 | N | PRO | 1128 | 37.943 | 4.934 | 10.335 1.00 34.66 |
| ATOM | 2234 | CD | PRO | 1128 | 38.477 | 6.142 | 9.685 1.00 35.04 |
| ATOM | 2235 | CA | PRO | 1128 | 36.612 | 5.251 | 10.871 1.00 31.59 |
| ATOM | 2236 | CB | PRO | 1128 | 36.511 | 6.776 | 10.669 1.00 32.56 |
| ATOM | 2237 | CG | PRO | 1128 | 37.819 | 7.222 | 10.499 1.00 31.06 |
| ATOM | 2238 | C | PRO | 1128 | 35.648 | 4.597 | 9.916 1.00 33.99 |
| ATOM | 2239 | O | PRO | 1128 | 35.975 | 4.429 | 8.749 1.00 38.28 |
| ATOM | 2240 | N | ASP | 1129 | 34.416 | 4.371 | 10.344 1.00 31.98 |
| ATOM | 2242 | CA | ASP | 1129 | 33.425 | 3.728 | 9.489 1.00 34.11 |
| ATOM | 2243 | CB | ASP | 1129 | 32.157 | 3.432 | 10.277 1.00 29.91 |
| ATOM | 2244 | CG | ASP | 1129 | 32.447 | 2.811 | 11.623 1.00 34.04 |
| ATOM | 2245 | OD1 | ASP | 1129 | 33.519 | 2.172 | 11.805 1.00 35.22 |
| ATOM | 2246 | OD2 | ASP | 1129 | 31.597 | 2.976 | 12.515 1.00 36.43 |
| ATOM | 2247 | C | ASP | 1129 | 33.061 | 4.360 | 8.158 1.00 35.75 |
| ATOM | 2248 | O | ASP | 1129 | 32.441 | 3.699 | 7.312 1.00 38.26 |
| ATOM | 2249 | N | TYR | 1130 | 33.444 | 5.613 | 7.925 1.00 32.58 |
| ATOM | 2251 | CA | TYR | 1130 | 33.056 | 6.200 | 6.649 1.00 34.86 |
| ATOM | 2252 | CB | TYR | 1130 | 32.067 | 7.332 | 6.888 1.00 38.26 |
| ATOM | 2253 | CG | TYR | 1130 | 30.996 | 6.960 | 7.889 1.00 37.51 |
| ATOM | 2254 | CD1 | TYR | 1130 | 31.208 | 7.153 | 9.245 1.00 36.44 |
| ATOM | 2255 | CE1 | TYR | 1130 | 30.249 | 6.853 | 10.148 1.00 40.00 |
| ATOM | 2256 | CD2 | TYR | 1130 | 29.787 | 6.442 | 7.468 1.00 39.18 |
| ATOM | 2257 | CE2 | TYR | 1130 | 28.813 | 6.143 | 8.360 1.00 34.53 |
| ATOM | 2258 | CZ | TYR | 1130 | 29.050 | 6.353 | 9.709 1.00 39.16 |
| ATOM | 2259 | OH | TYR | 1130 | 28.120 | 6.147 | 10.690 1.00 47.34 |
| ATOM | 2261 | C | TYR | 1130 | 34.136 | 6.657 | 5.732 1.00 34.80 |
| ATOM | 2262 | O | TYR | 1130 | 33.853 | 7.257 | 4.694 1.00 27.05 |
| ATOM | 2263 | N | THR | 1131 | 35.388 | 6.414 | 6.108 1.00 37.58 |
| ATOM | 2265 | CA | THR | 1131 | 36.457 | 6.829 | 5.238 1.00 38.70 |
| ATOM | 2266 | CB | THR | 1131 | 37.783 | 6.598 | 5.763 1.00 39.57 |
| ATOM | 2267 | OG1 | THR | 1131 | 37.775 | 5.417 | 6.564 1.00 51.23 |
| ATOM | 2269 | CG2 | THR | 1131 | 38.250 | 7.775 | 6.481 1.00 49.58 |
| ATOM | 2270 | C | THR | 1131 | 36.476 | 6.071 | 3.955 1.00 38.19 |
| ATOM | 2271 | O | THR | 1131 | 35.913 | 4.967 | 3.808 1.00 38.82 |
| ATOM | 2272 | N | THR | 1132 | 37.297 | 6.649 | 3.104 1.00 31.58 |
| ATOM | 2274 | CA | THR | 1132 | 37.638 | 6.148 | 1.836 1.00 27.37 |
| ATOM | 2275 | CB | THR | 1132 | 37.591 | 7.302 | 0.887 1.00 18.06 |
| ATOM | 2276 | OG1 | THR | 1132 | 36.274 | 7.366 | 0.348 1.00 29.75 |

FIG. 7(46)

| ATOM | 2278 | CG2 | THR | 1132 | 38.528 | 7.126 | -0.161 | 1.00 | 32.09 |
|---|---|---|---|---|---|---|---|---|---|
| ATOM | 2279 | C | THR | 1132 | 39.064 | 5.634 | 2.159 | 1.00 | 31.18 |
| ATOM | 2280 | O | THR | 1132 | 39.678 | 6.088 | 3.149 | 1.00 | 37.35 |
| ATOM | 2281 | N | PRO | 1133 | 39.543 | 4.601 | 1.439 | 1.00 | 29.49 |
| ATOM | 2282 | CD | PRO | 1133 | 38.884 | 3.875 | 0.336 | 1.00 | 28.18 |
| ATOM | 2283 | CA | PRO | 1133 | 40.876 | 4.065 | 1.686 | 1.00 | 23.60 |
| ATOM | 2284 | CB | PRO | 1133 | 41.029 | 2.998 | 0.604 | 1.00 | 29.05 |
| ATOM | 2285 | CG | PRO | 1133 | 39.640 | 2.581 | 0.319 | 1.00 | 28.36 |
| ATOM | 2286 | C | PRO | 1133 | 41.917 | 5.122 | 1.500 | 1.00 | 22.87 |
| ATOM | 2287 | O | PRO | 1133 | 42.944 | 5.119 | 2.182 | 1.00 | 30.07 |
| ATOM | 2288 | N | GLU | 1134 | 41.700 | 5.983 | 0.511 | 1.00 | 18.80 |
| ATOM | 2290 | CA | GLU | 1134 | 42.656 | 7.049 | 0.264 | 1.00 | 22.21 |
| ATOM | 2291 | CB | GLU | 1134 | 42.594 | 7.573 | -1.160 | 1.00 | 26.28 |
| ATOM | 2292 | CG | GLU | 1134 | 41.214 | 7.564 | -1.765 | 1.00 | 40.23 |
| ATOM | 2293 | CD | GLU | 1134 | 40.901 | 6.347 | -2.617 | 1.00 | 42.05 |
| ATOM | 2294 | OE1 | GLU | 1134 | 41.727 | 6.004 | -3.504 | 1.00 | 44.65 |
| ATOM | 2295 | OE2 | GLU | 1134 | 39.799 | 5.779 | -2.453 | 1.00 | 44.07 |
| ATOM | 2296 | C | GLU | 1134 | 42.547 | 8.164 | 1.300 | 1.00 | 21.07 |
| ATOM | 2297 | O | GLU | 1134 | 43.528 | 8.877 | 1.543 | 1.00 | 20.78 |
| ATOM | 2298 | N | MET | 1135 | 41.375 | 8.304 | 1.940 | 1.00 | 20.24 |
| ATOM | 2300 | CA | MET | 1135 | 41.233 | 9.304 | 2.996 | 1.00 | 16.52 |
| ATOM | 2301 | CB | MET | 1135 | 39.775 | 9.658 | 3.319 | 1.00 | 17.57 |
| ATOM | 2302 | CG | MET | 1135 | 39.158 | 10.807 | 2.420 | 1.00 | 15.02 |
| ATOM | 2303 | SD | MET | 1135 | 40.199 | 12.320 | 2.187 | 1.00 | 20.17 |
| ATOM | 2304 | CE | MET | 1135 | 40.632 | 12.648 | 3.877 | 1.00 | 13.20 |
| ATOM | 2305 | C | MET | 1135 | 41.974 | 8.751 | 4.191 | 1.00 | 20.41 |
| ATOM | 2306 | O | MET | 1135 | 42.772 | 9.461 | 4.787 | 1.00 | 25.79 |
| ATOM | 2307 | N | TYR | 1136 | 41.836 | 7.448 | 4.445 | 1.00 | 20.30 |
| ATOM | 2309 | CA | TYR | 1136 | 42.565 | 6.817 | 5.540 | 1.00 | 17.65 |
| ATOM | 2310 | CB | TYR | 1136 | 42.082 | 5.394 | 5.832 | 1.00 | 21.89 |
| ATOM | 2311 | CG | TYR | 1136 | 42.786 | 4.775 | 7.041 | 1.00 | 26.17 |
| ATOM | 2312 | CD1 | TYR | 1136 | 42.702 | 5.353 | 8.325 | 1.00 | 20.81 |
| ATOM | 2313 | CE1 | TYR | 1136 | 43.364 | 4.781 | 9.427 | 1.00 | 17.33 |
| ATOM | 2314 | CD2 | TYR | 1136 | 43.554 | 3.612 | 6.900 | 1.00 | 26.03 |
| ATOM | 2315 | CE2 | TYR | 1136 | 44.225 | 3.034 | 7.998 | 1.00 | 12.75 |
| ATOM | 2316 | CZ | TYR | 1136 | 44.124 | 3.615 | 9.245 | 1.00 | 16.64 |
| ATOM | 2317 | OH | TYR | 1136 | 44.791 | 2.999 | 10.281 | 1.00 | 17.57 |
| ATOM | 2319 | C | TYR | 1136 | 44.077 | 6.847 | 5.267 | 1.00 | 14.28 |
| ATOM | 2320 | O | TYR | 1136 | 44.892 | 7.066 | 6.179 | 1.00 | 19.62 |
| ATOM | 2321 | N | GLN | 1137 | 44.479 | 6.693 | 4.022 | 1.00 | 12.55 |

FIG. 7(47)

| | | | | | | | |
|---|---|---|---|---|---|---|---|
| ATOM | 2323 | CA  | GLN | 1137 | 45.903 | 6.777  | 3.758 1.00 16.34 |
| ATOM | 2324 | CB  | GLN | 1137 | 46.218 | 6.412  | 2.325 1.00 18.36 |
| ATOM | 2325 | CG  | GLN | 1137 | 47.702 | 6.654  | 1.945 1.00 21.79 |
| ATOM | 2326 | CD  | GLN | 1137 | 48.613 | 5.655  | 2.561 1.00 14.21 |
| ATOM | 2327 | OE1 | GLN | 1137 | 48.416 | 4.469  | 2.381 1.00 22.64 |
| ATOM | 2328 | NE2 | GLN | 1137 | 49.571 | 6.111  | 3.344 1.00 18.97 |
| ATOM | 2331 | C   | GLN | 1137 | 46.415 | 8.193  | 4.041 1.00 20.40 |
| ATOM | 2332 | O   | GLN | 1137 | 47.598 | 8.378  | 4.391 1.00 25.11 |
| ATOM | 2333 | N   | THR | 1138 | 45.564 | 9.194  | 3.807 1.00 18.65 |
| ATOM | 2335 | CA  | THR | 1138 | 45.939 | 10.568 | 4.068 1.00 15.52 |
| ATOM | 2336 | CB  | THR | 1138 | 44.921 | 11.507 | 3.538 1.00 19.97 |
| ATOM | 2337 | OG1 | THR | 1138 | 44.797 | 11.257 | 2.144 1.00 18.74 |
| ATOM | 2339 | CG2 | THR | 1138 | 45.381 | 12.939 | 3.722 1.00 21.70 |
| ATOM | 2340 | C   | THR | 1138 | 46.111 | 10.721 | 5.566 1.00 12.73 |
| ATOM | 2341 | O   | THR | 1138 | 47.067 | 11.344 | 6.010 1.00 18.83 |
| ATOM | 2342 | N   | MET | 1139 | 45.233 | 10.118 | 6.352 1.00 9.32 |
| ATOM | 2344 | CA  | MET | 1139 | 45.402 | 10.151 | 7.809 1.00 12.25 |
| ATOM | 2345 | CB  | MET | 1139 | 44.295 | 9.349  | 8.480 1.00 13.21 |
| ATOM | 2346 | CG  | MET | 1139 | 42.967 | 10.007 | 8.354 1.00 5.60 |
| ATOM | 2347 | SD  | MET | 1139 | 41.708 | 8.982  | 9.003 1.00 17.66 |
| ATOM | 2348 | CE  | MET | 1139 | 40.510 | 9.337  | 7.925 1.00 2.00 |
| ATOM | 2349 | C   | MET | 1139 | 46.773 | 9.567  | 8.198 1.00 15.96 |
| ATOM | 2350 | O   | MET | 1139 | 47.573 | 10.237 | 8.855 1.00 17.30 |
| ATOM | 2351 | N   | LEU | 1140 | 47.058 | 8.333  | 7.770 1.00 15.29 |
| ATOM | 2353 | CA  | LEU | 1140 | 48.357 | 7.735  | 8.081 1.00 14.20 |
| ATOM | 2354 | CB  | LEU | 1140 | 48.542 | 6.409  | 7.326 1.00 6.27 |
| ATOM | 2355 | CG  | LEU | 1140 | 47.511 | 5.373  | 7.745 1.00 15.42 |
| ATOM | 2356 | CD1 | LEU | 1140 | 47.656 | 4.103  | 6.927 1.00 8.64 |
| ATOM | 2357 | CD2 | LEU | 1140 | 47.648 | 5.103  | 9.246 1.00 14.99 |
| ATOM | 2358 | C   | LEU | 1140 | 49.518 | 8.684  | 7.751 1.00 17.20 |
| ATOM | 2359 | O   | LEU | 1140 | 50.552 | 8.691  | 8.442 1.00 18.73 |
| ATOM | 2360 | N   | ASP | 1141 | 49.396 | 9.413  | 6.644 1.00 20.16 |
| ATOM | 2362 | CA  | ASP | 1141 | 50.442 | 10.374 | 6.229 1.00 19.52 |
| ATOM | 2363 | CB  | ASP | 1141 | 50.139 | 10.963 | 4.851 1.00 20.89 |
| ATOM | 2364 | CG  | ASP | 1141 | 50.228 | 9.942  | 3.772 1.00 25.01 |
| ATOM | 2365 | OD1 | ASP | 1141 | 50.537 | 8.765  | 4.074 1.00 30.17 |
| ATOM | 2366 | OD2 | ASP | 1141 | 49.994 | 10.321 | 2.624 1.00 26.42 |
| ATOM | 2367 | C   | ASP | 1141 | 50.627 | 11.521 | 7.207 1.00 15.10 |
| ATOM | 2368 | O   | ASP | 1141 | 51.762 | 11.905 | 7.502 1.00 8.73 |
| ATOM | 2369 | N   | CYS | 1142 | 49.504 | 12.101 | 7.637 1.00 10.75 |

FIG. 7(48)

| ATOM | 2371 | CA  | CYS | 1142 | 49.516 | 13.196 | 8.590  | 1.00 | 13.88 |
|------|------|-----|-----|------|--------|--------|--------|------|-------|
| ATOM | 2372 | CB  | CYS | 1142 | 48.110 | 13.776 | 8.739  | 1.00 | 17.83 |
| ATOM | 2373 | SG  | CYS | 1142 | 47.414 | 14.574 | 7.291  | 1.00 | 17.66 |
| ATOM | 2374 | C   | CYS | 1142 | 50.042 | 12.717 | 9.961  | 1.00 | 15.52 |
| ATOM | 2375 | O   | CYS | 1142 | 50.545 | 13.513 | 10.734 | 1.00 | 16.31 |
| ATOM | 2376 | N   | TRP | 1143 | 49.883 | 11.424 | 10.266 | 1.00 | 20.06 |
| ATOM | 2378 | CA  | TRP | 1143 | 50.344 | 10.830 | 11.528 | 1.00 | 17.66 |
| ATOM | 2379 | CB  | TRP | 1143 | 49.393 | 9.727  | 11.991 | 1.00 | 15.44 |
| ATOM | 2380 | CG  | TRP | 1143 | 48.041 | 10.236 | 12.273 | 1.00 | 14.25 |
| ATOM | 2381 | CD2 | TRP | 1143 | 46.814 | 9.495  | 12.233 | 1.00 | 18.13 |
| ATOM | 2382 | CE2 | TRP | 1143 | 45.774 | 10.401 | 12.540 | 1.00 | 12.59 |
| ATOM | 2383 | CE3 | TRP | 1143 | 46.490 | 8.143  | 11.966 | 1.00 | 16.02 |
| ATOM | 2384 | CD1 | TRP | 1143 | 47.710 | 11.514 | 12.605 | 1.00 | 7.90  |
| ATOM | 2385 | NE1 | TRP | 1143 | 46.355 | 11.618 | 12.768 | 1.00 | 13.52 |
| ATOM | 2387 | CZ2 | TRP | 1143 | 44.425 | 10.012 | 12.592 | 1.00 | 8.83  |
| ATOM | 2388 | CZ3 | TRP | 1143 | 45.155 | 7.755  | 12.017 | 1.00 | 11.61 |
| ATOM | 2389 | CH2 | TRP | 1143 | 44.133 | 8.691  | 12.327 | 1.00 | 16.83 |
| ATOM | 2390 | C   | TRP | 1143 | 51.765 | 10.281 | 11.442 | 1.00 | 23.22 |
| ATOM | 2391 | O   | TRP | 1143 | 52.208 | 9.507  | 12.298 | 1.00 | 27.31 |
| ATOM | 2392 | N   | HIS | 1144 | 52.510 | 10.722 | 10.440 | 1.00 | 24.48 |
| ATOM | 2394 | CA  | HIS | 1144 | 53.876 | 10.280 | 10.299 | 1.00 | 26.08 |
| ATOM | 2395 | CB  | HIS | 1144 | 54.495 | 10.859 | 9.023  | 1.00 | 19.25 |
| ATOM | 2396 | CG  | HIS | 1144 | 55.791 | 10.214 | 8.654  | 1.00 | 18.57 |
| ATOM | 2397 | CD2 | HIS | 1144 | 56.923 | 10.003 | 9.374  | 1.00 | 14.60 |
| ATOM | 2398 | ND1 | HIS | 1144 | 56.016 | 9.657  | 7.415  | 1.00 | 19.61 |
| ATOM | 2400 | CE1 | HIS | 1144 | 57.231 | 9.133  | 7.387  | 1.00 | 19.99 |
| ATOM | 2401 | NE2 | HIS | 1144 | 57.803 | 9.332  | 8.562  | 1.00 | 15.04 |
| ATOM | 2403 | C   | HIS | 1144 | 54.710 | 10.671 | 11.542 | 1.00 | 32.65 |
| ATOM | 2404 | O   | HIS | 1144 | 54.626 | 11.795 | 12.031 | 1.00 | 31.70 |
| ATOM | 2405 | N   | GLY | 1145 | 55.541 | 9.734  | 12.016 | 1.00 | 37.26 |
| ATOM | 2407 | CA  | GLY | 1145 | 56.393 | 9.970  | 13.168 | 1.00 | 31.32 |
| ATOM | 2408 | C   | GLY | 1145 | 57.251 | 11.212 | 13.001 | 1.00 | 35.04 |
| ATOM | 2409 | O   | GLY | 1145 | 57.372 | 11.989 | 13.942 | 1.00 | 38.42 |
| ATOM | 2410 | N   | GLU | 1146 | 57.915 | 11.373 | 11.852 | 1.00 | 34.51 |
| ATOM | 2412 | CA  | GLU | 1146 | 58.735 | 12.577 | 11.598 | 1.00 | 37.16 |
| ATOM | 2413 | CB  | GLU | 1146 | 59.871 | 12.303 | 10.627 | 1.00 | 37.16 |
| ATOM | 2414 | CG  | GLU | 1146 | 61.093 | 11.742 | 11.292 | 1.00 | 50.26 |
| ATOM | 2415 | CD  | GLU | 1146 | 61.186 | 10.243 | 11.110 | 1.00 | 54.17 |
| ATOM | 2416 | OE1 | GLU | 1146 | 61.158 | 9.509  | 12.125 | 1.00 | 55.25 |
| ATOM | 2417 | OE2 | GLU | 1146 | 61.280 | 9.804  | 9.938  | 1.00 | 59.09 |

FIG. 7(49)

| | | | | | | |
|---|---|---|---|---|---|---|
| ATOM | 2418 | C   | GLU 1146 | 57.910 | 13.742 | 11.052 1.00 36.46 |
| ATOM | 2419 | O   | GLU 1146 | 57.378 | 13.665 |  9.934 1.00 35.72 |
| ATOM | 2420 | N   | PRO 1147 | 57.861 | 14.868 | 11.791 1.00 34.09 |
| ATOM | 2421 | CD  | PRO 1147 | 58.490 | 15.147 | 13.099 1.00 33.72 |
| ATOM | 2422 | CA  | PRO 1147 | 57.082 | 16.020 | 11.336 1.00 29.77 |
| ATOM | 2423 | CB  | PRO 1147 | 57.446 | 17.106 | 12.351 1.00 27.86 |
| ATOM | 2424 | CG  | PRO 1147 | 57.668 | 16.334 | 13.619 1.00 26.72 |
| ATOM | 2425 | C   | PRO 1147 | 57.436 | 16.417 |  9.922 1.00 27.04 |
| ATOM | 2426 | O   | PRO 1147 | 56.559 | 16.784 |  9.158 1.00 30.21 |
| ATOM | 2427 | N   | SER 1148 | 58.698 | 16.255 |  9.551 1.00 22.56 |
| ATOM | 2429 | CA  | SER 1148 | 59.177 | 16.616 |  8.210 1.00 24.23 |
| ATOM | 2430 | CB  | SER 1148 | 60.707 | 16.724 |  8.203 1.00 27.40 |
| ATOM | 2431 | OG  | SER 1148 | 61.314 | 15.477 |  8.545 1.00 36.19 |
| ATOM | 2433 | C   | SER 1148 | 58.743 | 15.674 |  7.101 1.00 21.41 |
| ATOM | 2434 | O   | SER 1148 | 58.890 | 15.964 |  5.913 1.00 24.41 |
| ATOM | 2435 | N   | GLN 1149 | 58.272 | 14.508 |  7.485 1.00 25.45 |
| ATOM | 2437 | CA  | GLN 1149 | 57.831 | 13.547 |  6.497 1.00 26.28 |
| ATOM | 2438 | CB  | GLN 1149 | 58.224 | 12.142 |  6.946 1.00 32.79 |
| ATOM | 2439 | CG  | GLN 1149 | 59.705 | 11.907 |  6.958 1.00 25.96 |
| ATOM | 2440 | CD  | GLN 1149 | 60.279 | 12.196 |  5.622 1.00 32.77 |
| ATOM | 2441 | OE1 | GLN 1149 | 59.765 | 11.744 |  4.591 1.00 36.63 |
| ATOM | 2442 | NE2 | GLN 1149 | 61.312 | 13.007 |  5.604 1.00 37.86 |
| ATOM | 2445 | C   | GLN 1149 | 56.327 | 13.670 |  6.278 1.00 23.40 |
| ATOM | 2446 | O   | GLN 1149 | 55.783 | 13.145 |  5.306 1.00 23.12 |
| ATOM | 2447 | N   | ARG 1150 | 55.662 | 14.339 |  7.215 1.00 22.72 |
| ATOM | 2449 | CA  | ARG 1150 | 54.226 | 14.581 |  7.132 1.00 17.86 |
| ATOM | 2450 | CB  | ARG 1150 | 53.721 | 15.243 |  8.392 1.00 16.38 |
| ATOM | 2451 | CG  | ARG 1150 | 54.161 | 14.532 |  9.598 1.00 13.96 |
| ATOM | 2452 | CD  | ARG 1150 | 53.285 | 14.903 | 10.728 1.00 15.08 |
| ATOM | 2453 | NE  | ARG 1150 | 53.632 | 14.090 | 11.879 1.00 24.55 |
| ATOM | 2455 | CZ  | ARG 1150 | 54.066 | 14.564 | 13.040 1.00 27.63 |
| ATOM | 2456 | NH1 | ARG 1150 | 54.192 | 15.871 | 13.230 1.00 27.18 |
| ATOM | 2459 | NH2 | ARG 1150 | 54.423 | 13.717 | 13.991 1.00 29.34 |
| ATOM | 2462 | C   | ARG 1150 | 54.025 | 15.559 |  6.008 1.00 16.82 |
| ATOM | 2463 | O   | ARG 1150 | 54.913 | 16.382 |  5.715 1.00 13.09 |
| ATOM | 2464 | N   | PRO 1151 | 52.873 | 15.464 |  5.320 1.00 18.01 |
| ATOM | 2465 | CD  | PRO 1151 | 51.793 | 14.453 |  5.320 1.00  6.32 |
| ATOM | 2466 | CA  | PRO 1151 | 52.726 | 16.442 |  4.240 1.00 18.95 |
| ATOM | 2467 | CB  | PRO 1151 | 51.489 | 15.948 |  3.492 1.00 16.01 |
| ATOM | 2468 | CG  | PRO 1151 | 50.726 | 15.092 |  4.520 1.00 10.59 |

FIG. 7(50)

```
ATOM  2469 C   PRO 1151    52.574 17.861  4.805 1.00 18.27
ATOM  2470 O   PRO 1151    52.422 18.039  6.006 1.00 19.70
ATOM  2471 N   THR 1152    52.763 18.860  3.958 1.00 19.16
ATOM  2473 CA  THR 1152    52.604 20.251  4.366 1.00 14.92
ATOM  2474 CB  THR 1152    53.511 21.138  3.560 1.00 13.80
ATOM  2475 OG1 THR 1152    53.146 21.080  2.163 1.00 17.02
ATOM  2477 CG2 THR 1152    54.918 20.697  3.764 1.00  5.40
ATOM  2478 C   THR 1152    51.196 20.571  3.979 1.00 13.16
ATOM  2479 O   THR 1152    50.682 19.905  3.084 1.00 19.18
ATOM  2480 N   PHE 1153    50.561 21.572  4.599 1.00 14.62
ATOM  2482 CA  PHE 1153    49.176 21.910  4.224 1.00 12.87
ATOM  2483 CB  PHE 1153    48.588 23.023  5.083 1.00 11.95
ATOM  2484 CG  PHE 1153    48.157 22.558  6.422 1.00  9.67
ATOM  2485 CD1 PHE 1153    47.037 21.740  6.560 1.00 14.91
ATOM  2486 CD2 PHE 1153    48.891 22.857  7.533 1.00 15.01
ATOM  2487 CE1 PHE 1153    46.660 21.215  7.802 1.00  9.44
ATOM  2488 CE2 PHE 1153    48.529 22.340  8.789 1.00 13.43
ATOM  2489 CZ  PHE 1153_   47.405 21.513  8.913 1.00  8.41
ATOM  2490 C   PHE 1153    49.073 22.253  2.750 1.00 16.98
ATOM  2491 O   PHE 1153    48.078 21.927  2.114 1.00 21.60
ATOM  2492 N   SER 1154    50.116 22.841  2.168 1.00 15.39
ATOM  2494 CA  SER 1154    50.031 23.123  0.754 1.00 17.55
ATOM  2495 CB  SER 1154    51.251 23.868  0.254 1.00 25.28
ATOM  2496 OG  SER 1154    51.244 25.190  0.776 1.00 33.35
ATOM  2498 C   SER 1154    49.850 21.815  0.022 1.00 20.26
ATOM  2499 O   SER 1154    48.932 21.704 -0.798 1.00 23.74
ATOM  2500 N   GLU 1155    50.670 20.808  0.347 1.00 19.47
ATOM  2502 CA  GLU 1155    50.534 19.493 -0.307 1.00 16.55
ATOM  2503 CB  GLU 1155    51.588 18.513  0.188 1.00 19.82
ATOM  2504 CG  GLU 1155    52.932 18.773 -0.486 1.00 20.20
ATOM  2505 CD  GLU 1155    54.128 18.210  0.249 1.00 23.11
ATOM  2506 OE1 GLU 1155    55.226 18.377 -0.312 1.00 35.76
ATOM  2507 OE2 GLU 1155    54.009 17.631  1.359 1.00 21.09
ATOM  2508 C   GLU 1155    49.153 18.918 -0.107 1.00 16.59
ATOM  2509 O   GLU 1155    48.548 18.414 -1.055 1.00 21.37
ATOM  2510 N   LEU 1156    48.619 19.034  1.101 1.00 16.01
ATOM  2512 CA  LEU 1156    47.272 18.532  1.375 1.00 18.06
ATOM  2513 CB  LEU 1156    46.969 18.521  2.875 1.00 15.74
ATOM  2514 CG  LEU 1156    47.688 17.493  3.759 1.00 11.35
ATOM  2515 CD1 LEU 1156    47.786 18.049  5.201 1.00  2.08
```

FIG. 7(51)

| ATOM | 2516 | CD2 | LEU | 1156 | 46.927 | 16.150 | 3.708 | 1.00 | 14.36 |
|---|---|---|---|---|---|---|---|---|---|
| ATOM | 2517 | C | LEU | 1156 | 46.165 | 19.287 | 0.638 | 1.00 | 20.03 |
| ATOM | 2518 | O | LEU | 1156 | 45.105 | 18.711 | 0.355 | 1.00 | 26.86 |
| ATOM | 2519 | N | VAL | 1157 | 46.354 | 20.570 | 0.355 | 1.00 | 21.44 |
| ATOM | 2521 | CA | VAL | 1157 | 45.303 | 21.283 | -0.362 | 1.00 | 21.15 |
| ATOM | 2522 | CB | VAL | 1157 | 45.513 | 22.801 | -0.381 | 1.00 | 21.33 |
| ATOM | 2523 | CG1 | VAL | 1157 | 44.569 | 23.453 | -1.368 | 1.00 | 15.98 |
| ATOM | 2524 | CG2 | VAL | 1157 | 45.198 | 23.340 | 0.974 | 1.00 | 13.87 |
| ATOM | 2525 | C | VAL | 1157 | 45.270 | 20.721 | -1.760 | 1.00 | 22.88 |
| ATOM | 2526 | O | VAL | 1157 | 44.198 | 20.508 | -2.333 | 1.00 | 25.54 |
| ATOM | 2527 | N | GLU | 1158 | 46.445 | 20.400 | -2.282 | 1.00 | 23.10 |
| ATOM | 2529 | CA | GLU | 1158 | 46.503 | 19.815 | -3.603 | 1.00 | 27.24 |
| ATOM | 2530 | CB | GLU | 1158 | 47.922 | 19.756 | -4.115 | 1.00 | 32.82 |
| ATOM | 2531 | CG | GLU | 1158 | 47.969 | 18.978 | -5.404 | 1.00 | 44.73 |
| ATOM | 2532 | CD | GLU | 1158 | 49.187 | 19.268 | -6.212 | 1.00 | 51.53 |
| ATOM | 2533 | OE1 | GLU | 1158 | 49.007 | 19.887 | -7.292 | 1.00 | 54.31 |
| ATOM | 2534 | OE2 | GLU | 1158 | 50.298 | 18.869 | -5.765 | 1.00 | 51.10 |
| ATOM | 2535 | C | GLU | 1158 | 45.939 | 18.403 | -3.643 | 1.00 | 26.42 |
| ATOM | 2536 | O | GLU | 1158 | 45.167 | 18.051 | -4.546 | 1.00 | 25.91 |
| ATOM | 2537 | N | HIS | 1159 | 46.347 | 17.591 | -2.669 | 1.00 | 26.36 |
| ATOM | 2539 | CA | HIS | 1159 | 45.897 | 16.226 | -2.611 | 1.00 | 21.52 |
| ATOM | 2540 | CB | HIS | 1159 | 46.674 | 15.444 | -1.576 | 1.00 | 25.28 |
| ATOM | 2541 | CG | HIS | 1159 | 46.322 | 13.991 | -1.545 | 1.00 | 24.66 |
| ATOM | 2542 | CD2 | HIS | 1159 | 46.408 | 13.030 | -2.497 | 1.00 | 24.44 |
| ATOM | 2543 | ND1 | HIS | 1159 | 45.749 | 13.387 | -0.452 | 1.00 | 21.30 |
| ATOM | 2545 | CE1 | HIS | 1159 | 45.489 | 12.125 | -0.731 | 1.00 | 23.16 |
| ATOM | 2546 | NE2 | HIS | 1159 | 45.879 | 11.884 | -1.961 | 1.00 | 19.88 |
| ATOM | 2548 | C | HIS | 1159 | 44.402 | 16.104 | -2.391 | 1.00 | 21.56 |
| ATOM | 2549 | O | HIS | 1159 | 43.741 | 15.311 | -3.066 | 1.00 | 22.19 |
| ATOM | 2550 | N | LEU | 1160 | 43.852 | 16.874 | -1.456 | 1.00 | 20.25 |
| ATOM | 2552 | CA | LEU | 1160 | 42.408 | 16.832 | -1.209 | 1.00 | 17.66 |
| ATOM | 2553 | CB | LEU | 1160 | 42.111 | 17.502 | 0.130 | 1.00 | 17.84 |
| ATOM | 2554 | CG | LEU | 1160 | 42.676 | 16.760 | 1.352 | 1.00 | 20.17 |
| ATOM | 2555 | CD1 | LEU | 1160 | 42.472 | 17.542 | 2.619 | 1.00 | 21.45 |
| ATOM | 2556 | CD2 | LEU | 1160 | 41.992 | 15.454 | 1.512 | 1.00 | 19.45 |
| ATOM | 2557 | C | LEU | 1160 | 41.566 | 17.418 | -2.395 | 1.00 | 17.71 |
| ATOM | 2558 | O | LEU | 1160 | 40.426 | 17.030 | -2.624 | 1.00 | 15.39 |
| ATOM | 2559 | N | GLY | 1161 | 42.130 | 18.356 | -3.153 | 1.00 | 23.52 |
| ATOM | 2561 | CA | GLY | 1161 | 41.434 | 18.879 | -4.322 | 1.00 | 21.37 |
| ATOM | 2562 | C | GLY | 1161 | 41.342 | 17.741 | -5.346 | 1.00 | 23.91 |

FIG. 7(52)

| | | | | | | | |
|---|---|---|---|---|---|---|---|
| ATOM | 2563 | O | GLY | 1161 | 40.295 17.526 -5.971 | 1.00 | 23.05 |
| ATOM | 2564 | N | ASN | 1162 | 42.439 16.997 -5.520 | 1.00 | 21.49 |
| ATOM | 2566 | CA | ASN | 1162 | 42.428 15.854 -6.428 | 1.00 | 22.31 |
| ATOM | 2567 | CB | ASN | 1162 | 43.771 15.109 -6.427 | 1.00 | 22.34 |
| ATOM | 2568 | CG | ASN | 1162 | 44.904 15.888 -7.062 | 1.00 | 20.03 |
| ATOM | 2569 | OD1 | ASN | 1162 | 44.705 16.903 -7.701 | 1.00 | 28.17 |
| ATOM | 2570 | ND2 | ASN | 1162 | 46.117 15.401 -6.873 | 1.00 | 32.22 |
| ATOM | 2573 | C | ASN | 1162 | 41.356 14.851 -5.969 | 1.00 | 23.05 |
| ATOM | 2574 | O | ASN | 1162 | 40.570 14.378 -6.769 | 1.00 | 26.11 |
| ATOM | 2575 | N | LEU | 1163 | 41.360 14.490 -4.688 | 1.00 | 21.05 |
| ATOM | 2577 | CA | LEU | 1163 | 40.405 13.523 -4.166 | 1.00 | 19.91 |
| ATOM | 2578 | CB | LEU | 1163 | 40.695 13.172 -2.689 | 1.00 | 19.18 |
| ATOM | 2579 | CG | LEU | 1163 | 41.675 12.042 -2.275 | 1.00 | 18.62 |
| ATOM | 2580 | CD1 | LEU | 1163 | 42.959 12.120 -3.020 | 1.00 | 24.35 |
| ATOM | 2581 | CD2 | LEU | 1163 | 41.983 12.043 -0.804 | 1.00 | 14.82 |
| ATOM | 2582 | C | LEU | 1163 | 39.015 14.038 -4.331 | 1.00 | 19.71 |
| ATOM | 2583 | O | LEU | 1163 | 38.110 13.318 -4.767 | 1.00 | 23.11 |
| ATOM | 2584 | N | LEU | 1164 | 38.860 15.328 -4.121 | 1.00 | 25.91 |
| ATOM | 2586 | CA | LEU | 1164 | 37.533 15.941 -4.226 | 1.00 | 29.28 |
| ATOM | 2587 | CB | LEU | 1164 | 37.603 17.388 -3.726 | 1.00 | 31.25 |
| ATOM | 2588 | CG | LEU | 1164 | 36.348 18.176 -3.371 | 1.00 | 25.75 |
| ATOM | 2589 | CD1 | LEU | 1164 | 35.429 17.396 -2.435 | 1.00 | 31.52 |
| ATOM | 2590 | CD2 | LEU | 1164 | 7.018 15.866 -5.653 | 1.00 | 30.07 |
| ATOM | 2592 | O | LEU | 1164 | 35.953 15.330 -5.903 | 1.00 | 32.61 |
| ATOM | 2593 | N | GLN | 1165 | 37.810 16.344 -6.598 | 1.00 | 33.76 |
| ATOM | 2595 | CA | GLN | 1165 | 37.423 16.317 -8.003 | 1.00 | 39.95 |
| ATOM | 2596 | CB | GLN | 1165 | 38.451 17.048 -8.855 | 1.00 | 46.90 |
| ATOM | 2597 | CG | GLN | 1165 | 38.758 18.474 -8.480 | 1.00 | 49.81 |
| ATOM | 2598 | CD | GLN | 1165 | 39.874 19.024 -9.348 | 1.00 | 56.23 |
| ATOM | 2599 | OE1 | GLN | 1165 | 41.056 18.945 -8.997 | 1.00 | 55.97 |
| ATOM | 2600 | NE2 | GLN | 1165 | 39.508 19.536 -10.518 | 1.00 | 60.66 |
| ATOM | 2603 | C | GLN | 1165 | 37.304 14.898 -8.554 | 1.00 | 39.33 |
| ATOM | 2604 | O | GLN | 1165 | 36.652 14.685 -9.568 | 1.00 | 42.09 |
| ATOM | 2605 | N | ALA | 1166 | 38.059 13.965 -7.988 | 1.00 | 36.82 |
| ATOM | 2607 | CA | ALA | 1166 | 37.994 12.586 -8.441 | 1.00 | 34.66 |
| ATOM | 2608 | CB | ALA | 1166 | 39.096 11.748 -7.814 | 1.00 | 32.78 |
| ATOM | 2609 | C | ALA | 1166 | 36.640 12.103 -7.991 | 1.00 | 36.63 |
| ATOM | 2610 | O | ALA | 1166 | 35.969 11.381 -8.713 | 1.00 | 39.47 |
| ATOM | 2611 | N | ASN | 1167 | 36.226 12.532 -6.800 | 1.00 | 40.01 |
| ATOM | 2613 | CA | ASN | 1167 | 34.911 12.158 -6.264 | 1.00 | 42.40 |

FIG. 7(53)

```
ATOM  2614 CB  ASN  1167    34.641 12.878 -4.919 1.00 42.99
ATOM  2615 CG  ASN  1167    33.354 12.409 -4.242 1.00 40.80
ATOM  2616 OD1 ASN  1167    32.306 13.046 -4.348 1.00 40.18
ATOM  2617 ND2 ASN  1167    33.436 11.294 -3.532 1.00 36.58
ATOM  2620 C   ASN  1167    33.822 12.498 -7.299 1.00 41.88
ATOM  2621 O   ASN  1167    32.837 11.789 -7.391 1.00 41.83
ATOM  2622 N   ALA  1168    34.057 13.558 -8.085 1.00 45.09
ATOM  2624 CA  ALA  1168    33.187 14.065 -9.160 1.00 46.02
ATOM  2625 CB  ALA  1168    32.507 12.933 -9.929 1.00 45.92
ATOM  2626 C   ALA  1168    32.181 15.123 -8.728 1.00 48.61
ATOM  2628 O   ALA  1168    32.627 16.233 -8.363 1.00 50.20
ATOM  2629 O   HOH  1       46.858 21.496 16.690 1.00 23.54
ATOM  2632 O   HOH  2       49.904 21.605 17.271 1.00 36.65
ATOM  2635 O   HOH  3       49.682 18.133 17.657 1.00 50.47
ATOM  2638 O   HOH  4       56.606 19.394 15.202 1.00 25.28
ATOM  2641 O   HOH  5       57.215 21.949 11.395 1.00 37.66
ATOM  2644 O   HOH  6       56.082 25.850 12.933 1.00 34.63
ATOM  2647 O   HOH  7       52.355 23.016  6.377 1.00 21.45
ATOM  2650 O   HOH  8       51.153 27.376  4.088 1.00 29.93
ATOM  2653 O   HOH  9       44.820 28.454  1.120 1.00 16.47
ATOM  2656 O   HOH  10      46.377 38.321  5.198 1.00 31.93
ATOM  2659 O   HOH  11      43.987 38.133  3.129 1.00 52.41
ATOM  2662 O   HOH  12      53.321 40.451  6.702 1.00 31.88
ATOM  2665 O   HOH  13      44.977 49.530  8.305 1.00 44.56
ATOM  2668 O   HOH  14      44.379 43.338  7.798 1.00 31.72
ATOM  2671 O   HOH  15      39.477 40.232  8.468 1.00 36.65
ATOM  2674 O   HOH  16      41.987 36.751 10.646 1.00 23.26
ATOM  2677 O   HOH  17      41.711 41.873  6.802 1.00 34.79
ATOM  2680 O   HOH  18      29.514 24.656 18.739 1.00 31.43
ATOM  2683 O   HOH  19      27.493 22.351 15.517 1.00 42.03
ATOM  2686 O   HOH  20      24.345 20.097 15.325 1.00 24.92
ATOM  2689 O   HOH  21      32.381 18.452 20.520 1.00 75.12
ATOM  2692 O   HOH  22      31.071  8.282 19.507 1.00 31.68
ATOM  2695 O   HOH  23      33.001  7.742 21.598 1.00 38.67
ATOM  2698 O   HOH  24      34.802  6.439 18.667 1.00 34.24
ATOM  2701 O   HOH  25      32.273  6.932 14.174 1.00 41.21
ATOM  2704 O   HOH  26      34.059  5.245 12.870 1.00 49.30
ATOM  2707 O   HOH  27      38.059  3.432  4.799 1.00 63.69
ATOM  2710 O   HOH  28      41.089  1.841  4.421 1.00 42.86
ATOM  2713 O   HOH  29      45.081  9.234 -0.557 1.00 39.97
```

FIG. 7(54)

| | | | | | | | | |
|---|---|---|---|---|---|---|---|---|
| ATOM | 2716 | O | HOH | 30 | 47.301 | 11.215 | 1.271 | 1.00 58.47 |
| ATOM | 2719 | O | HOH | 31 | 50.046 | 14.055 | 0.168 | 1.00 37.58 |
| ATOM | 2722 | O | HOH | 32 | 54.425 | 8.937 | 4.821 | 1.00 36.74 |
| ATOM | 2725 | O | HOH | 33 | 52.279 | 7.099 | 5.152 | 1.00 13.04 |
| ATOM | 2728 | O | HOH | 34 | 53.025 | 7.510 | 7.740 | 1.00 25.53 |
| ATOM | 2731 | O | HOH | 35 | 50.852 | 6.818 | 10.462 | 1.00 18.29 |
| ATOM | 2734 | O | HOH | 36 | 46.448 | 7.762 | 15.254 | 1.00 9.08 |
| ATOM | 2737 | O | HOH | 37 | 47.326 | 3.930 | 20.460 | 1.00 34.16 |
| ATOM | 2740 | O | HOH | 38 | 48.264 | 12.367 | 20.804 | 1.00 22.14 |
| ATOM | 2743 | O | HOH | 39 | 44.276 | 8.193 | 24.312 | 1.00 40.52 |
| ATOM | 2746 | O | HOH | 40 | 37.491 | 11.237 | 25.975 | 1.00 38.71 |
| ATOM | 2749 | O | HOH | 41 | 37.592 | 13.565 | 23.164 | 1.00 44.55 |
| ATOM | 2752 | O | HOH | 42 | 34.887 | 12.418 | 26.235 | 1.00 50.96 |
| ATOM | 2755 | O | HOH | 43 | 24.823 | 15.933 | 17.377 | 1.00 33.72 |
| ATOM | 2758 | O | HOH | 44 | 23.302 | 7.532 | 7.049 | 1.00 57.56 |
| ATOM | 2761 | O | HOH | 45 | 29.954 | 11.864 | -3.109 | 1.00 38.05 |
| ATOM | 2764 | O | HOH | 46 | 42.099 | 3.812 | 18.044 | 1.00 40.12 |
| ATOM | 2767 | O | HOH | 47 | 38.653 | 0.737 | 18.003 | 1.00 37.30 |
| ATOM | 2770 | O | HOH | 48 | 34.169 | 14.465 | 16.707 | 1.00 20.01 |
| ATOM | 2773 | O | HOH | 49 | 37.055 | 32.622 | 16.570 | 1.00 31.20 |
| ATOM | 2776 | O | HOH | 50 | 29.361 | 31.729 | 15.460 | 1.00 21.90 |
| ATOM | 2779 | O | HOH | 51 | 25.866 | 31.495 | 10.192 | 1.00 24.50 |
| ATOM | 2782 | O | HOH | 52 | 23.411 | 32.276 | 10.616 | 1.00 68.85 |
| ATOM | 2785 | O | HOH | 53 | 22.135 | 37.404 | 8.648 | 1.00 40.22 |
| ATOM | 2788 | O | HOH | 54 | 28.356 | 36.997 | 10.747 | 1.00 22.41 |
| ATOM | 2791 | O | HOH | 55 | 29.650 | 33.190 | 8.897 | 1.00 31.98 |
| ATOM | 2794 | O | HOH | 56 | 34.801 | 35.904 | 3.297 | 1.00 59.73 |
| ATOM | 2797 | O | HOH | 57 | 24.341 | 20.715 | 4.934 | 1.00 28.10 |
| ATOM | 2800 | O | HOH | 58 | 37.439 | 20.236 | 25.832 | 1.00 33.07 |
| ATOM | 2803 | O | HOH | 59 | 32.675 | 51.977 | 19.122 | 1.00 33.52 |
| ATOM | 2806 | O | HOH | 60 | 32.722 | 54.003 | 14.118 | 1.00 25.01 |
| ATOM | 2809 | O | HOH | 61 | 29.691 | 54.769 | 22.004 | 1.00 27.32 |
| ATOM | 2812 | O | HOH | 62 | 21.347 | 47.577 | 14.711 | 1.00 27.85 |
| ATOM | 2815 | O | HOH | 63 | 25.640 | 44.257 | 7.516 | 1.00 24.71 |
| ATOM | 2818 | O | HOH | 64 | 24.686 | 40.916 | 3.785 | 1.00 55.13 |
| ATOM | 2821 | O | HOH | 65 | 33.825 | 48.721 | 10.105 | 1.00 39.11 |
| ATOM | 2824 | O | HOH | 66 | 39.855 | 54.415 | 18.247 | 1.00 50.97 |
| ATOM | 2827 | O | HOH | 67 | 36.001 | 50.053 | 7.081 | 1.00 68.99 |
| ATOM | 2830 | O | HOH | 68 | 37.973 | 50.651 | 5.331 | 1.00 32.12 |
| ATOM | 2833 | O | HOH | 69 | 40.220 | 53.227 | 6.506 | 1.00 15.02 |

FIG. 7(55)

| | | | | | | | | |
|---|---|---|---|---|---|---|---|---|
| ATOM | 2836 | O | HOH | 70 | 42.258 | 51.833 | 6.993 | 1.00 21.05 |
| ATOM | 2839 | O | HOH | 71 | 36.813 | 55.217 | 13.035 | 1.00 46.29 |
| ATOM | 2842 | O | HOH | 72 | 37.030 | 55.879 | 15.712 | 1.00 39.36 |
| ATOM | 2845 | O | HOH | 73 | 23.054 | 45.061 | 23.607 | 1.00 51.11 |
| ATOM | 2848 | O | HOH | 74 | 27.075 | 54.516 | 6.971 | 1.00 51.66 |
| ATOM | 2851 | O | HOH | 75 | 21.634 | 54.039 | 13.651 | 1.00 36.36 |
| ATOM | 2854 | O | HOH | 76 | 45.158 | 47.529 | 30.699 | 1.00 56.11 |
| ATOM | 2857 | O | HOH | 77 | 44.469 | 45.246 | 36.699 | 1.00 36.50 |
| ATOM | 2860 | O | HOH | 78 | 45.882 | 41.717 | 36.085 | 1.00 28.57 |
| ATOM | 2863 | O | HOH | 79 | 49.406 | 41.527 | 34.292 | 1.00 65.94 |
| ATOM | 2866 | O | HOH | 80 | 36.134 | 49.719 | 26.101 | 1.00 63.80 |
| ATOM | 2869 | O | HOH | 81 | 26.884 | 28.564 | 16.554 | 1.00 49.20 |
| ATOM | 2872 | O | HOH | 82 | 22.079 | 10.131 | 13.444 | 1.00 56.45 |
| ATOM | 2875 | O | HOH | 83 | 41.225 | 4.655 | 30.464 | 1.00 58.98 |
| ATOM | 2878 | O | HOH | 84 | 47.309 | 1.568 | 10.326 | 1.00 21.69 |
| ATOM | 2881 | O | HOH | 85 | 56.613 | 18.335 | 6.527 | 1.00 33.97 |
| ATOM | 2884 | O | HOH | 86 | 56.196 | 16.855 | 3.275 | 1.00 47.24 |
| ATOM | 2887 | O | HOH | 87 | 54.826 | 22.813 | 0.598 | 1.00 33.50 |
| ATOM | 2890 | O | HOH | 88 | 52.962 | 21.915 | -2.351 | 1.00 66.62 |
| ATOM | 2893 | O | HOH | 89 | 47.896 | 24.242 | -3.714 | 1.00 40.99 |
| ATOM | 2896 | O | HOH | 90 | 40.295 | 22.360 | 25.551 | 1.00 39.81 |
| ATOM | 2899 | O | HOH | 91 | 40.188 | 3.202 | 15.661 | 1.00 45.97 |
| ATOM | 2902 | O | HOH | 92 | 45.159 | 2.965 | 19.553 | 1.00 44.25 |
| ATOM | 2905 | O | HOH | 93 | 36.591 | 7.772 | 23.374 | 1.00 68.23 |
| ATOM | 2908 | O | HOH | 94 | 34.274 | 5.197 | 22.878 | 1.00 51.62 |
| ATOM | 2911 | O | HOH | 95 | 41.935 | 7.033 | 29.073 | 1.00 63.23 |
| ATOM | 2914 | O | HOH | 96 | 20.731 | 12.105 | 14.716 | 1.00 54.80 |
| ATOM | 2917 | O | HOH | 97 | 23.147 | 13.682 | 17.882 | 1.00 50.81 |
| ATOM | 2920 | O | HOH | 98 | 35.515 | 9.509 | -3.558 | 1.00 56.70 |
| ATOM | 2923 | O | HOH | 99 | 38.933 | 9.503 | -1.231 | 1.00 32.18 |
| ATOM | 2926 | O | HOH | 100 | 51.814 | 24.438 | 3.703 | 1.00 52.00 |
| ATOM | 2929 | O | HOH | 101 | 51.670 | 28.690 | 0.838 | 1.00 42.41 |
| ATOM | 2932 | O | HOH | 102 | 46.536 | 30.610 | 1.750 | 1.00 45.80 |
| ATOM | 2935 | O | HOH | 103 | 45.165 | 34.214 | 0.818 | 1.00 46.46 |
| ATOM | 2938 | O | HOH | 104 | 42.695 | 35.194 | 1.055 | 1.00 25.82 |
| ATOM | 2941 | O | HOH | 105 | 39.689 | 33.418 | 0.723 | 1.00 31.99 |
| ATOM | 2944 | O | HOH | 106 | 23.962 | 38.119 | 27.549 | 1.00 47.89 |
| ATOM | 2947 | O | HOH | 107 | 25.343 | 40.908 | 27.379 | 1.00 54.09 |
| ATOM | 2950 | O | HOH | 108 | 20.307 | 35.738 | 19.866 | 1.00 32.61 |
| ATOM | 2953 | O | HOH | 109 | 28.085 | 54.303 | 18.810 | 1.00 61.58 |

FIG. 7(56)

| | | | | | | | | |
|---|---|---|---|---|---|---|---|---|
| ATOM | 2956 | O | HOH | 110 | 29.849 | 56.131 | 16.966 | 1.00 37.29 |
| ATOM | 2959 | O | HOH | 111 | 31.503 | 58.023 | 14.735 | 1.00 46.45 |
| ATOM | 2962 | O | HOH | 112 | 35.212 | 55.981 | 10.499 | 1.00 92.07 |
| ATOM | 2965 | O | HOH | 113 | 36.530 | 55.812 | 6.656 | 1.00 30.72 |
| ATOM | 2968 | O | HOH | 114 | 50.045 | 41.251 | 26.059 | 1.00 82.26 |
| ATOM | 2971 | O | HOH | 115 | 25.153 | 36.460 | 9.054 | 1.00 50.86 |
| ATOM | 2974 | O | HOH | 116 | 31.749 | 32.705 | 15.359 | 1.00 30.04 |
| ATOM | 2977 | O | HOH | 117 | 30.213 | 3.806 | 4.940 | 1.00 39.74 |
| ATOM | 2980 | O | HOH | 118 | 36.511 | 1.159 | 7.275 | 1.00 41.62 |
| ATOM | 2983 | O | HOH | 119 | 27.155 | 4.637 | 5.224 | 1.00 79.92 |
| ATOM | 2986 | O | HOH | 120 | 57.319 | 11.287 | 3.459 | 1.00 33.02 |
| ATOM | 2989 | O | HOH | 121 | 52.121 | 12.483 | 1.755 | 1.00 45.55 |
| ATOM | 2992 | O | HOH | 122 | 47.613 | 14.088 | -5.021 | 1.00 41.01 |
| ATOM | 2995 | O | HOH | 123 | 57.550 | 26.628 | 16.551 | 1.00 30.62 |
| ATOM | 2998 | O | HOH | 124 | 32.338 | 10.125 | 23.559 | 1.00 35.48 |
| ATOM | 3001 | O | HOH | 125 | 31.065 | 5.698 | 3.273 | 1.00 42.74 |
| ATOM | 3004 | O | HOH | 126 | 32.603 | 4.523 | 1.410 | 1.00 33.30 |
| ATOM | 3007 | O | HOH | 127 | 34.394 | 2.617 | 4.702 | 1.00 42.12 |
| ATOM | 3010 | O | HOH | 128 | 37.961 | 10.373 | -4.287 | 1.00 47.57 |
| ATOM | 3013 | O | HOH | 129 | 42.215 | 11.947 | -6.970 | 1.00 45.13 |
| ATOM | 3016 | O | HOH | 130 | 46.307 | 8.952 | -4.280 | 1.00 70.02 |
| ATOM | 3019 | O | HOH | 131 | 50.369 | 17.388 | -3.277 | 1.00 42.22 |
| ATOM | 3022 | O | HOH | 132 | 47.231 | 21.866 | 22.930 | 1.00 50.84 |
| ATOM | 3025 | O | HOH | 133 | 45.362 | 17.669 | 27.147 | 1.00 48.06 |
| ATOM | 3028 | O | HOH | 134 | 27.005 | 23.141 | 18.124 | 1.00 49.65 |
| ATOM | 3031 | O | HOH | 135 | 45.726 | 12.511 | -6.453 | 1.00 45.31 |
| ATOM | 3034 | O | HOH | 136 | 46.998 | 11.755 | 18.088 | 1.00 37.38 |
| ATOM | 3037 | O | HOH | 137 | 39.706 | 37.699 | 9.894 | 1.00 40.71 |
| ATOM | 3040 | O | HOH | 138 | 18.768 | 48.678 | 17.798 | 1.00 74.62 |
| ATOM | 3043 | O | HOH | 139 | 43.641 | 47.080 | 26.762 | 1.00 44.64 |
| ATOM | 3046 | O | HOH | 140 | 32.593 | 53.980 | 16.744 | 1.00 43.95 |
| ATOM | 3049 | O | HOH | 141 | 34.726 | 55.568 | 14.399 | 1.00 45.86 |
| ATOM | 3052 | O | HOH | 142 | 30.551 | 53.227 | 19.638 | 1.00 35.99 |
| ATOM | 3055 | O | HOH | 143 | 26.370 | 55.161 | 14.300 | 1.00 33.09 |
| ATOM | 3058 | O | HOH | 144 | 24.547 | 55.803 | 6.815 | 1.00 58.70 |
| ATOM | 3061 | O | HOH | 145 | 36.217 | 52.574 | 3.221 | 1.00 68.48 |
| ATOM | 3064 | O | HOH | 146 | 39.065 | 54.455 | 4.595 | 1.00 48.85 |
| ATOM | 3067 | O | HOH | 147 | 45.130 | 40.725 | 5.433 | 1.00 62.58 |
| ATOM | 3070 | O | HOH | 148 | 33.453 | 43.988 | 7.386 | 1.00 41.59 |
| ATOM | 3073 | O | HOH | 149 | 36.626 | 45.045 | 6.144 | 1.00 54.04 |

FIG. 7(57)

| | | | | | | | | |
|---|---|---|---|---|---|---|---|---|
| ATOM | 3076 | O | HOH | 150 | 19.458 | 36.977 | 14.386 | 1.00 56.50 |
| ATOM | 3079 | O | HOH | 151 | 19.502 | 40.993 | 17.850 | 1.00 43.35 |
| ATOM | 3082 | O | HOH | 152 | 39.793 | 38.257 | 27.760 | 1.00 63.31 |
| ATOM | 3085 | O | HOH | 153 | 40.730 | 53.944 | 20.682 | 1.00 49.91 |
| ATOM | 3088 | O | HOH | 154 | 45.371 | 49.402 | 5.710 | 1.00 41.53 |
| ATOM | 3091 | O | HOH | 155 | 49.114 | 26.038 | 11.482 | 1.00 34.43 |
| ATOM | 3094 | O | HOH | 156 | 54.085 | 28.403 | 10.828 | 1.00 28.60 |
| ATOM | 3097 | O | HOH | 157 | 18.729 | 14.990 | 12.752 | 1.00 44.66 |
| ATOM | 3100 | O | HOH | 158 | 27.500 | 2.046 | 10.138 | 1.00 47.88 |
| ATOM | 3103 | O | HOH | 159 | 23.505 | 7.763 | 16.082 | 1.00 45.49 |
| ATOM | 3106 | O | HOH | 160 | 38.101 | 22.326 | 23.406 | 1.00 43.42 |
| ATOM | 3109 | O | HOH | 161 | 36.788 | 33.961 | 0.261 | 1.00 59.95 |
| ATOM | 3112 | O | HOH | 162 | 19.380 | 27.777 | 6.595 | 1.00 56.29 |
| ATOM | 3115 | O | HOH | 163 | 33.583 | 33.343 | 17.339 | 1.00 68.25 |
| ATOM | 3118 | O | HOH | 164 | 43.221 | 53.467 | 17.853 | 1.00 62.89 |
| ATOM | 3121 | O | HOH | 165 | 28.154 | 41.110 | 29.042 | 1.00 61.19 |
| ATOM | 3124 | O | HOH | 166 | 44.877 | 47.914 | 12.583 | 1.00 21.27 |
| ATOM | 3127 | O | HOH | 167 | 46.589 | 45.908 | 14.329 | 1.00 39.48 |
| ATOM | 3130 | O | HOH | 168 | 48.235 | 43.490 | 14.297 | 1.00 46.88 |
| ATOM | 3133 | O | HOH | 169 | 47.834 | 0.528 | 14.762 | 1.00 74.55 |
| ATOM | 3136 | O | HOH | 170 | 48.711 | -2.009 | 16.386 | 1.00 52.45 |
| ATOM | 3139 | O | HOH | 171 | 41.210 | 0.396 | 17.381 | 1.00 58.05 |
| ATOM | 3142 | O | HOH | 172 | 43.837 | 1.538 | 17.483 | 1.00 72.30 |
| ATOM | 3145 | O | HOH | 173 | 41.780 | -2.478 | 14.396 | 1.00 47.15 |
| ATOM | 3148 | O | HOH | 174 | 31.466 | 11.699 | 21.418 | 1.00 45.99 |
| ATOM | 3151 | O | HOH | 175 | 35.046 | 14.218 | 20.429 | 1.00 39.37 |
| ATOM | 3154 | O | HOH | 176 | 22.639 | 26.143 | 4.324 | 1.00 36.80 |
| ATOM | 3157 | O | HOH | 177 | 26.114 | 24.452 | 6.028 | 1.00 31.04 |
| ATOM | 3160 | O | HOH | 178 | 28.927 | 30.687 | 4.252 | 1.00 41.38 |
| ATOM | 3163 | O | HOH | 179 | 23.899 | 6.610 | 18.621 | 1.00 56.43 |
| ATOM | 3166 | O | HOH | 180 | 53.386 | 11.969 | 4.493 | 1.00 39.86 |
| ATOM | 3169 | O | HOH | 181 | 30.051 | 43.727 | 0.910 | 1.00 47.97 |
| ATOM | 3172 | O | HOH | 182 | 31.659 | 49.099 | 8.149 | 1.00 52.84 |

SEQUENCE LISTING

<160> NUMBER OF SEQ ID NOS: 12

<210> SEQ ID NO 1
<211> LENGTH: 31
<212> TYPE: DNA
<213> ORGANISM: Homo sapiens

<400> SEQUENCE: 1
cagcatatgg atccagatga actcccattg g         31

<210> SEQ ID NO 2
<211> LENGTH: 34
<212> TYPE: DNA
<213> ORGANISM: Homo sapiens

<400> SEQUENCE: 2
gcggtcgact taaacaggag gagagctcag tgtg      34

<210> SEQ ID NO 3
<211> LENGTH: 33
<212> TYPE: DNA
<213> ORGANISM: Homo sapiens

<400> SEQUENCE: 3
gcacatatgg aacgactgcc ttatgatgcc agc       33

<210> SEQ ID NO 4
<211> LENGTH: 38
<212> TYPE: DNA
<213> ORGANISM: Homo sapiens

<400> SEQUENCE: 4
cctgtcgact tatccagaat cctcttccat gctcaaag  38

<210> SEQ ID NO 5
<211> LENGTH: 317
<212> TYPE: PRT
<213> ORGANISM: Homo sapiens

<400> SEQUENCE: 5

Met Asp Pro Asp Glu Leu Pro Leu Asp Glu His Cys Glu Arg Leu Pro
 1               5                  10                  15

Tyr Asp Ala Ser Lys Trp Glu Phe Pro Arg Asp Arg Leu Lys Leu Gly
                20                  25                  30

Lys Pro Leu Gly Arg Gly Ala Phe Gly Gln Val Ile Glu Ala Asp Ala
            35                  40                  45

Phe Gly Ile Asp Lys Thr Ala Thr Cys Arg Thr Val Ala Val Lys Met
        50                  55                  60

Leu Lys Glu Gly Ala Thr His Ser Glu His Arg Ala Leu Met Ser Glu
    65                  70                  75                  80

Leu Lys Ile Leu Ile His Ile Gly His His Leu Asn Val Val Asn Leu
                85                  90                  95

Leu Gly Ala Cys Thr Lys Pro Gly Gly Pro Leu Met Val Ile Val Glu
            100                 105                 110

Phe Cys Lys Phe Gly Asn Leu Ser Thr Tyr Leu Arg Ser Lys Arg Asn
        115                 120                 125

Glu Phe Val Pro Tyr Lys Glu Ala Pro Glu Asp Leu Tyr Lys Asp Phe
    130                 135                 140

-continued

```
Leu Thr Leu Glu His Leu Leu Ile Cys Tyr Ser Phe Gln Val Ala Lys
145                 150                 155                 160

Gly Met Glu Phe Leu Ala Ser Arg Lys Cys Ile His Arg Asp Leu Ala
                165                 170                 175

Ala Arg Asn Ile Leu Leu Ser Glu Lys Asn Val Val Lys Ile Cys Asp
            180                 185                 190

Phe Gly Leu Ala Arg Asp Ile Tyr Lys Asp Pro Asp Tyr Val Arg Lys
        195                 200                 205

Gly Asp Ala Arg Leu Pro Leu Lys Trp Met Ala Pro Glu Thr Ile Phe
    210                 215                 220

Asp Arg Val Tyr Thr Ile Gln Ser Asp Val Trp Ser Phe Gly Val Leu
225                 230                 235                 240

Leu Trp Glu Ile Phe Ser Leu Gly Ala Ser Pro Tyr Pro Gly Val Lys
                245                 250                 255

Ile Asp Glu Glu Phe Cys Arg Arg Leu Lys Glu Gly Thr Arg Met Arg
            260                 265                 270

Ala Pro Asp Tyr Thr Thr Pro Glu Met Tyr Gln Thr Met Leu Asp Cys
        275                 280                 285

Trp His Gly Glu Pro Ser Gln Arg Pro Thr Phe Ser Glu Leu Val Glu
    290                 295                 300

His Leu Gly Asn Leu Leu Gln Ala Asn Ala Gln Gln Asp
305                 310                 315

<210> SEQ ID NO 6
<211> LENGTH: 386
<212> TYPE: PRT
<213> ORGANISM: E. coli

<400> SEQUENCE: 6

Asp Pro Met Gln Leu Pro Tyr Asp Ser Arg Trp Glu Phe Pro Arg Asp
  1               5                  10                  15

Gly Leu Val Leu Gly Arg Val Leu Gly Ser Gly Ala Phe Gly Lys Val
                 20                  25                  30

Val Glu Gly Thr Ala Tyr Gly Leu Ser Arg Ser Gln Pro Val Met Lys
             35                  40                  45

Val Ala Val Lys Met Leu Lys Pro Thr Ala Arg Ser Ser Glu Lys Gln
         50                  55                  60

Ala Leu Met Ser Glu Leu Lys Ile Met Thr His Leu Gly Pro His Leu
 65                  70                  75                  80

Asn Ile Val Asn Leu Leu Gly Ala Cys Thr Lys Ser Gly Pro Ile Tyr
                 85                  90                  95

Ile Ile Thr Glu Tyr Cys Phe Tyr Gly Asp Leu Val Asn Tyr Leu His
            100                 105                 110

Lys Asn Arg Asp Ser Phe Leu Ser His His Pro Glu Lys Pro Lys Lys
        115                 120                 125

Glu Leu Asp Ile Phe Gly Leu Asn Pro Ala Asp Glu Ser Thr Arg Ser
    130                 135                 140

Tyr Val Ile Leu Ser Phe Glu Asn Asn Gly Asp Tyr Met Asp Met Lys
145                 150                 155                 160

Gln Ala Asp Thr Thr Gln Tyr Val Pro Met Leu Glu Arg Lys Glu Val
                165                 170                 175

Ser Lys Tyr Ser Asp Ile Gln Arg Ser Leu Tyr Asp Arg Pro Ala Ser
            180                 185                 190

Tyr Lys Lys Lys Ser Met Leu Asp Ser Glu Val Lys Asn Leu Leu Ser
        195                 200                 205
```

-continued

Asp Asp Asn Ser Glu Gly Leu Thr Leu Leu Asp Leu Leu Ser Phe Thr
210                 215                 220

Tyr Gln Val Ala Arg Gly Met Glu Phe Leu Ala Ser Lys Asn Cys Val
225                 230                 235                 240

His Arg Asp Leu Ala Ala Arg Asn Val Leu Leu Ala Gln Gly Lys Ile
        245                 250                 255

Val Lys Ile Cys Asp Phe Gly Leu Ala Arg Asp Ile Met His Asp Ser
            260                 265                 270

Asn Tyr Val Ser Lys Gly Ser Thr Phe Leu Pro Val Lys Trp Met Ala
        275                 280                 285

Pro Glu Ser Ile Phe Asp Asn Leu Tyr Thr Thr Leu Ser Asp Val Trp
    290                 295                 300

Ser Tyr Gly Ile Leu Leu Trp Glu Ile Phe Ser Leu Gly Gly Thr Pro
305                 310                 315                 320

Tyr Pro Gly Met Met Val Asp Ser Thr Phe Tyr Asn Lys Ile Lys Ser
                325                 330                 335

Gly Tyr Arg Met Ala Lys Pro Asp His Ala Thr Ser Glu Val Tyr Glu
            340                 345                 350

Ile Met Val Lys Cys Trp Asn Ser Glu Pro Glu Lys Arg Pro Ser Phe
        355                 360                 365

Tyr His Leu Ser Glu Ile Val Glu Asn Leu Leu Pro Gly Gln Tyr Lys
    370                 375                 380

Lys Ser
385

<210> SEQ ID NO 7
<211> LENGTH: 310
<212> TYPE: PRT
<213> ORGANISM: Homo sapiens

<400> SEQUENCE: 7

Met Leu Ala Gly Val Ser Glu Tyr Glu Leu Pro Glu Asp Pro Arg Trp
1               5                   10                  15

Glu Leu Pro Arg Asp Arg Leu Val Leu Gly Lys Pro Leu Gly Glu Gly
            20                  25                  30

Cys Phe Gly Gln Val Val Leu Ala Glu Ala Ile Gly Leu Asp Lys Asp
        35                  40                  45

Lys Pro Asn Arg Val Thr Lys Val Ala Val Lys Met Leu Lys Ser Asp
    50                  55                  60

Ala Thr Glu Lys Asp Leu Ser Asp Leu Ile Ser Glu Met Glu Met Met
65                  70                  75                  80

Lys Met Ile Gly Lys His Lys Asn Ile Ile Asn Leu Leu Gly Ala Cys
                85                  90                  95

Thr Gln Asp Gly Pro Leu Tyr Val Ile Val Glu Tyr Ala Ser Lys Gly
            100                 105                 110

Asn Leu Arg Glu Tyr Leu Gln Ala Arg Arg Pro Pro Gly Leu Glu Tyr
        115                 120                 125

Cys Tyr Asn Pro Ser His Asn Pro Glu Glu Gln Leu Ser Ser Lys Asp
    130                 135                 140

Leu Val Ser Cys Ala Tyr Gln Val Ala Arg Gly Met Glu Tyr Leu Ala
145                 150                 155                 160

Ser Lys Lys Cys Ile His Arg Asp Leu Ala Ala Arg Asn Val Leu Val
                165                 170                 175

Thr Glu Asp Asn Val Met Lys Ile Ala Asp Phe Gly Leu Ala Arg Asp

```
                180                 185                 190
Ile His His Ile Asp Tyr Tyr Lys Lys Thr Thr Asn Gly Arg Leu Pro
            195                 200                 205

Val Lys Trp Met Ala Pro Glu Ala Leu Phe Asp Arg Ile Tyr Thr His
210                 215                 220

Gln Ser Asp Val Trp Ser Phe Gly Val Leu Leu Trp Glu Ile Phe Thr
225                 230                 235                 240

Leu Gly Gly Ser Pro Tyr Pro Gly Val Pro Val Glu Glu Leu Phe Lys
                245                 250                 255

Leu Leu Lys Glu Gly His Arg Met Asp Lys Pro Ser Asn Cys Thr Asn
            260                 265                 270

Glu Leu Tyr Met Met Met Arg Asp Cys Trp His Ala Val Pro Ser Gln
            275                 280                 285

Arg Pro Thr Phe Lys Gln Leu Val Glu Asp Leu Asp Arg Ile Val Ala
        290                 295                 300

Leu Thr Ser Asn Gln Glu
305                 310

<210> SEQ ID NO 8
<211> LENGTH: 297
<212> TYPE: PRT
<213> ORGANISM: Homo sapiens

<400> SEQUENCE: 8

Val Phe Pro Cys Ser Val Tyr Val Pro Asp Glu Trp Glu Val Ser Arg
  1               5                  10                  15

Glu Lys Ile Thr Leu Arg Glu Leu Gly Gln Gly Ser Phe Gly Met
                20                  25                  30

Val Tyr Glu Gly Asn Ala Arg Asp Ile Ile Lys Gly Glu Ala Glu Thr
            35                  40                  45

Arg Val Ala Val Lys Thr Val Asn Glu Ser Ala Ser Leu Arg Glu Arg
        50                  55                  60

Ile Glu Phe Leu Asn Glu Ala Ser Val Met Lys Gly Phe Thr Cys His
65                  70                  75                  80

His Val Val Arg Leu Leu Gly Val Val Ser Lys Gly Gln Pro Thr Leu
                85                  90                  95

Val Val Met Glu Leu Met Ala His Gly Asp Leu Lys Ser Tyr Leu Arg
            100                 105                 110

Ser Leu Arg Pro Glu Ala Glu Asn Asn Pro Gly Arg Pro Pro Pro Thr
        115                 120                 125

Leu Gln Glu Met Ile Gln Met Ala Ala Glu Ile Ala Asp Gly Met Ala
130                 135                 140

Tyr Leu Asn Ala Lys Lys Phe Val His Arg Asp Leu Ala Ala Arg Asn
145                 150                 155                 160

Cys Met Val Ala His Asp Phe Thr Val Lys Ile Gly Asp Phe Gly Met
                165                 170                 175

Thr Arg Asp Ile Tyr Glu Thr Asp Tyr Tyr Arg Lys Gly Gly Lys Gly
            180                 185                 190

Leu Leu Pro Val Arg Trp Met Ala Pro Glu Ser Leu Lys Asp Gly Val
        195                 200                 205

Phe Thr Thr Ser Ser Asp Met Trp Ser Phe Gly Val Val Leu Trp Glu
210                 215                 220

Ile Thr Ser Leu Ala Glu Gln Pro Tyr Gln Gly Leu Ser Asn Glu Gln
225                 230                 235                 240
```

```
Val Leu Lys Phe Val Met Asp Gly Gly Tyr Leu Asp Gln Pro Asp Asn
                245                 250                 255

Cys Pro Glu Arg Val Thr Asp Leu Met Arg Met Cys Trp Gln Phe Asn
            260                 265                 270

Pro Asn Met Arg Pro Thr Phe Leu Glu Ile Val Asn Leu Leu Lys Asp
        275                 280                 285

Asp Leu His Pro Ser Phe Pro Glu Val
    290                 295

<210> SEQ ID NO 9
<211> LENGTH: 367
<212> TYPE: PRT
<213> ORGANISM: Homo sapiens

<400> SEQUENCE: 9

Met Asp Pro Asp Glu Val Pro Leu Asp Glu Gln Cys Glu Arg Leu Pro
  1               5                  10                  15

Tyr Asp Ala Ser Lys Trp Glu Phe Ala Arg Glu Arg Leu Lys Leu Gly
                20                  25                  30

Lys Ser Leu Gly Arg Gly Ala Phe Gly Lys Val Val Gln Ala Ser Ala
            35                  40                  45

Phe Gly Ile Lys Lys Ser Pro Thr Cys Arg Thr Val Ala Val Lys Met
    50                  55                  60

Leu Lys Glu Gly Ala Thr Ala Ser Glu Tyr Lys Ala Leu Met Thr Glu
 65                  70                  75                  80

Leu Lys Ile Leu Thr His Ile Gly His His Leu Asn Val Val Asn Leu
                85                  90                  95

Leu Gly Ala Cys Thr Lys Gln Gly Gly Pro Leu Met Val Ile Val Glu
            100                 105                 110

Tyr Cys Lys Tyr Gly Asn Leu Ser Asn Tyr Leu Lys Ser Lys Arg Asp
        115                 120                 125

Leu Phe Phe Leu Asn Lys Asp Ala Ala Leu His Met Glu Pro Lys Lys
    130                 135                 140

Glu Lys Met Glu Pro Gly Leu Glu Gln Gly Lys Lys Pro Arg Leu Asp
145                 150                 155                 160

Ser Val Thr Ser Ser Glu Ser Phe Ala Ser Ser Gly Phe Gln Glu Asp
                165                 170                 175

Lys Ser Leu Ser Asp Val Glu Glu Glu Asp Ser Asp Gly Phe Tyr
            180                 185                 190

Lys Glu Pro Ile Thr Met Glu Asp Leu Ile Ser Tyr Ser Phe Gln Val
        195                 200                 205

Ala Arg Gly Met Glu Phe Leu Ser Ser Arg Lys Cys Ile His Arg Asp
    210                 215                 220

Leu Ala Ala Arg Asn Ile Leu Leu Ser Glu Asn Asn Val Val Lys Ile
225                 230                 235                 240

Cys Asp Phe Gly Leu Ala Arg Asp Ile Tyr Lys Asn Pro Asp Tyr Val
                245                 250                 255

Arg Lys Gly Asp Thr Arg Leu Pro Leu Lys Trp Met Ala Pro Glu Ser
            260                 265                 270

Ile Phe Asp Lys Ile Tyr Ser Thr Lys Ser Asp Val Trp Ser Tyr Gly
        275                 280                 285

Val Leu Leu Trp Glu Ile Phe Ser Leu Gly Gly Ser Pro Tyr Pro Gly
    290                 295                 300

Val Gln Met Asp Glu Asp Phe Cys Ser Arg Leu Arg Glu Gly Met Arg
305                 310                 315                 320
```

```
Met Arg Ala Pro Glu Tyr Ser Thr Pro Glu Ile Tyr Gln Ile Met Leu
                325                 330                 335

Asp Cys Trp His Arg Asp Pro Lys Glu Arg Pro Arg Phe Ala Glu Leu
            340                 345                 350

Val Glu Lys Leu Gly Asp Leu Leu Gln Ala Asn Val Gln Gln Asp
        355                 360                 365

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10 tcagcagga ttgataagac tacattgttc                                      30

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
gaatttgtcc cctacaagga agctcctgaa gatctg                              36

<210> SEQ ID NO 12
<211> LENGTH: 367
<212> TYPE: PRT
<213> ORGANISM: Homo sapiens

<400> SEQUENCE: 12

Met Asp Pro Asp Glu Leu Pro Leu Asp Glu His Cys Glu Arg Leu Pro
  1               5                  10                  15

Tyr Asp Ala Ser Lys Trp Glu Phe Pro Arg Asp Arg Leu Lys Leu Gly
                 20                  25                  30

Lys Pro Leu Gly Arg Gly Ala Phe Gly Gln Val Ile Glu Ala Asp Ala
             35                  40                  45

Phe Gly Ile Asp Lys Thr Ala Thr Cys Arg Thr Val Ala Val Lys Met
 50                  55                  60

Leu Lys Glu Gly Ala Thr His Ser Glu His Arg Ala Leu Met Ser Glu
 65                  70                  75                  80

Leu Lys Ile Leu Ile His Ile Gly His His Leu Asn Val Val Asn Leu
                 85                  90                  95

Leu Gly Ala Cys Thr Lys Pro Gly Gly Pro Leu Met Val Ile Val Glu
            100                 105                 110

Phe Cys Lys Phe Gly Asn Leu Ser Thr Tyr Leu Arg Ser Lys Arg Asn
        115                 120                 125

Glu Phe Val Pro Tyr Lys Thr Lys Gly Ala Arg Phe Arg Gln Gly Lys
130                 135                 140

Asp Tyr Val Gly Ala Ile Pro Val Asp Leu Lys Arg Arg Leu Asp Ser
145                 150                 155                 160

Ile Thr Ser Ser Gln Ser Ser Ala Ser Ser Gly Phe Val Glu Glu Lys
                165                 170                 175

Ser Leu Ser Asp Val Glu Glu Glu Glu Ala Pro Glu Asp Leu Tyr Lys
            180                 185                 190
```

-continued

```
Asp Phe Leu Thr Leu Glu His Leu Leu Ile Cys Tyr Ser Phe Gln Val
        195             200             205
Ala Lys Gly Met Glu Phe Leu Ala Ser Arg Lys Cys Ile His Arg Asp
        210             215             220
Leu Ala Ala Arg Asn Ile Leu Leu Ser Glu Lys Asn Val Val Lys Ile
225             230             235             240
Cys Asp Phe Gly Leu Ala Arg Asp Ile Tyr Lys Asp Pro Asp Tyr Val
            245             250             255
Arg Lys Gly Asp Ala Arg Leu Pro Leu Lys Trp Met Ala Pro Glu Thr
            260             265             270
Ile Phe Asp Arg Val Tyr Thr Ile Gln Ser Asp Val Trp Ser Phe Gly
        275             280             285
Val Leu Leu Trp Glu Ile Phe Ser Leu Gly Ala Ser Pro Tyr Pro Gly
        290             295             300
Val Lys Ile Asp Glu Glu Phe Cys Arg Arg Leu Lys Glu Gly Thr Arg
305             310             315             320
Met Arg Ala Pro Asp Tyr Thr Thr Pro Glu Met Tyr Gln Thr Met Leu
            325             330             335
Asp Cys Trp His Gly Glu Pro Ser Gln Arg Pro Thr Phe Ser Glu Leu
            340             345             350
Val Glu His Leu Gly Asn Leu Leu Gln Ala Asn Ala Gln Gln Asp
        355             360             365
```

MODIFICATIONS OF THE VEGF RECEPTOR-2 PROTEIN AND METHODS OF USE

This application is a division of application Ser. No. 09/390,326, filed Sep. 7, 1999, now U.S. Pat. No. 6,316,603, which is based upon claims the benefit of Provisional application Serial No. 60/099,503, filed Sep. 8, 1998.

TECHNICAL FIELD AND INDUSTRIAL APPLICABILITY OF INVENTION

The present invention discloses the isolation of a key portion of the catalytic kinase region of vascular endothelial growth factor receptor 2 or VEGFR-2 through cloning, sequencing and x-ray crystallography. Also disclosed is the deletion of various amino acid residues from an area of the catalytic region called the kinase insert domain (KID). The resulting polypeptide retains comparable in vitro kinase activity to that of the wild-type KID and is not necessary for the catalytic activity of the polypeptide, and more importantly, allows complete crystallization of the protein such that it may be characterized by X-ray crystallography. The present invention further discloses x-ray crystallography data useful for identification and construction of therapeutic compounds in the treatment of various disease conditions associated with VEGFR2.

BACKGROUND OF THE INVENTION

Many physiological events including embryogenesis, organ development, estrus, and wound healing require vascular growth and remodeling (Folkman et al., (1992) *J. Biol. Chem.* 267, 10931–10934; Risau, W. (1995) *FASEB J.* 9, 926–933.). In addition to these beneficial processes, angiogenesis is also involved in the proliferation of disease states such as tumor growth, metastasis, psoriasis, rheumatoid arthritis, macular degeneration and retinopathy (Pepper, M. S., (1996) *Vasc. Med.* 1, 259–266; Kuiper et al., (1998) *Pharmacol. Res.* 37, 1–16, 1998; Kumar and Fidler, (1998) In Vivo 18, 27–34; Szekanecz et al., (1998) *J. Investig. Med.* 46, 27–41; Tolentino and Adamis, (1988) *Int. Ophthalmol. Clin.* 38, 77–94. Of the signaling pathways known to influence vascular formation, these involving vascular endothelial growth factor (VEGF) haves been shown to be essential and selective for vascular endothelial cells (Dvorak et al., (1995) *Am. J. Path.* 146, 1029–1039; Thomas, K., (1996) *J. Biol. Chem.* 271, 603–606; Ferrara N. and Davis-Smyth, (1997) *Endocrine Rev.* 18, 4–25). The therapeutic potential of inhibiting the VEGF pathway has been directly demonstrated by anti-VEGF monoclonal antibodies which were active against a variety of human tumors (Borgstrom et al, (1996) *Cancer Res.* 56, 4032–4039) and ischemic retinal disease (Adamis et al., (1996) *Arch. Ophthalmol.* 114, 66–71).

Normal vasculogenesis and angiogenesis play important roles in a variety of physiological processes such as embryonic development, wound healing, organ regeneration and female reproductive processes such as follicle development in the corpus luteum during ovulation and placental growth after pregnancy (Folkman & Shing, 1992). Uncontrolled vasculogenesis and/or angiogenesis has been associated with diseases, such as diabetes, as well as malignant solid tumors that rely on vascularization for growth. Klagsbum & Soker, (1993) *Current Biology* 3(10):699–702; Folkharn, (1991) *J. Natl., Cancer Inst.* 82:4–6; Weidner, et al., (1991) *New Engl. J. Med.* 324:1–5.

Several polypeptides with in vitro endothelial cell growth promoting activity have been identified. Examples include acidic and basic fibroblastic growth factor (FGF), vascular endothelial growth factor (VEGF)and placental growth factor. Unlike FGF, VEGF has recently been reported to be an endothelial cell specific mitogen (Ferrara & Henzel, (1989) *Biochem. Biophys. Res. Comm.* 161:851–858; Vaisman et al., (1990) *J. Biol. Chem.* 265:19461–19566).

Thus, identification of the specific receptors to which VEGF binds is important to understanding of the regulation of endothelial cell proliferation. Two structurally related tyrosine kinases have been identified to bind VEGF with high affinity: the flt-1 receptor (Shibuya et al., (1990) *Oncogene* 5:519–524; De Vries et al., (1992) *Science* 255:989–991) and the KDR/FLK-1receptor, discussed herein. Consequently, it had been surmised that RTKs may have a role in the modulation and regulation of endothelial cell proliferation.

Recent disclosures, such as information set forth in U.S. patent application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsburn & Soker, (1993) *Current Biology* 3:699–702; Houck, et al., (1992) *J. Biol. Chem.* 267:26031–26037.

VEGF is a homodimeric cytokine that is expressed in at least four splice-variant forms of 121–206 residues (Ferrara and Davis-Smyth, 1997). Vascular endothelial cells express at least two high-affinity receptors for VEGF: VEGF-R1/Flt-1 and VEGFR-2/KDR. VEGF-R1 and VEGFR-2 are receptor tyrosine kinases each comprised of an extracellular domain that contains 7 immunoglobulin-like segments and binds VEGF, a short membrane spanning region, and a cytosolic domain possessing tyrosine kinase activity. The kinase domain directly follows the extracellular and juxtamembrane regions and is itself followed by another domain (post-kinase domain), which may function in binding of other proteins for signal transduction. These two receptors appear to have different signaling pathways and functions with VEGFR-2 being of primary importance in mitosis of endothelial cells (Waltenberger et al., (1994) *J. Biol. Chem.* 269, 26988–26995; Seetharm et al., (1995) *Oncogene* 10, 135–147; Shalaby et al., (1995) *Nature* 376, 576–579).

Both FGF and VEGF are potent angiogenic factors which induce formation of new capillary blood vessels. Transfection of human breast carcinoma cell line MCF7 with FGF resulted in cell lines that form progressively growing and metastatic tumors when injected (s.c.) into nude mice. FGF may play a critical role in progression of breast tumors to an estrogen-independent, anti-estrogen resistant metastatic phenotype (McLeskey et al., (1993) *Cancer Res.* 53: 2168–2177). Breast tumor cells exhibited increased neovascularization, increased spontaneous metastasis and more rapid growth in vivo than did the non-transfected tumors. FGF has been shown to be transforming in NIH-3T3 cells and implicated in tumorigenesis and metastasis of mouse mammary tumors. FGF overexpression conferred a tumorigenic phenotype on a human adrenal carcinoma cell line suggesting that FGF's may also play a role in the transformation of epithelial cells. Polyclonal neutralizing antibodies to FGF inhibited tumor growth in Balb/c nude mice transplanted with K1000 cells (transfected with the leader sequence of bFGF) which form tumors in these mice (Hori et al., (1991) *Cancer Res.* 51: 6180–9184).

Due to the role of FGF in neovascularization, tumorigenesis and metastasis, there is a need in the art for FGF inhibitors as potent anti-cancer agents that exert their anti-FGF activity by preventing intracellular signaling of FGF.

VEGF, by contrast, is an endothelial cell-specific mitogen and an angiogenesis inducer that is released by a variety of tumor cells and expressed in human tumor cells in situ. Unlike FGF, transfection of cell lines with a cDNA sequence encoding VEGF, did not promote transformation, but did facilitate tumor growth in vivo (Ferrara, N., and Davis-Smyth, T. (1997)). Furthermore, administration of a polyclonal antibody which neutralized VEGF also inhibited growth of human rhabdomyosarcoma, glioblastoma multiforme and leiomyosarcoma cell lines in nude mice (Kim et al., (1993) *Nature* 362: 841–843).

In view of the importance of receptor tyrosine kinases (RTKs) to the control, regulation and modulation of endothelial cell proliferation and potentially vasculogenesis and/or angiogenesis, many attempts have been made to identify RTK "inhibitors" using a variety of approaches, including the use of mutant ligands (U.S. Pat. No. 4,966,849), soluble receptors and antibodies (Application No. WO 94/10202; Kendall & Thomas, (1994) *Proc. Natl. Acad. Sci.* 90:10705–09; Kim, et al., 1993), RNA ligands (Jellinek, et al., (1994) *Biochemistry* 3:10450–56), protein kinase C inhibitors (Schuchter, et al., (1991) *Cancer Res.* 51:682–687); Takano, et al., (1993) *Mol. Bio. Cell* 4:358A; Kinsella, et al., (1992) *Exp. Cell Res.* 199:56–62; Wright, et al., (1992) *J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., (1994) *Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642), vinylene-azaindole derivatives (PCT WO 94/14808) and 1-cyclopropypl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 AI), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. None of these compounds, however, have been previously associated with the enzymatic function of the VEGFR-2 receptor. Likewise, none of these compounds have been associated with regulation of vasculogenesis and/or angiogenesis.

Therefore, there is a need in the art to develop small molecule antagonists of the PDGF, FGF, EGF and VEGF pathways individually or as a group. Moreover, if these cytokines signal through a common second messenger pathway within the cell, such antagonists will have broad therapeutic activity to treat or prevent the progression of a broad array of diseases, such as coronary restenosis, tumor-associated angiogenesis, atherosclerosis, autoimmune diseases, acute inflammation, certain kidney diseases associated with proliferation of glomerular or mesangial cells, and ocular diseases associated with retinal vessel proliferation. The present invention was made by discovering a common signaling mechanism, a group of active therapeutic agents, shown to be active by a large number of and variety of predictive assays, and discovering a common intracellular signaling intermediate.

Based on sequence homology and overall domain structure, VEGFRs belong to the platelet-derived growth factor receptor family (PDGFR) which also includes PDGFRα, PDGFRβ, the stem cell growth factor receptor (c-kit), and the colony stimulating factor-1 receptor (CSF-1R/c-fms) (van der Geer et al., (1994) *Ann. Rev. Cell Biol.* 10, 251–337). Compared to other protein kinases, members of this family contain an insert of approximately 65–97 residues, termed the kinase insert domain (KID), within the catalytic kinase domain relative to other protein kinases. Within the PDGFR family the KIDs are of varying length and low sequence homology. Deletion or mutation of the KID from PDGFRα, PDGFRβ, c-kit, and CSF-1R have indicated that this domain is not necessary for intrinsic kinase activity but that it is important for the binding of other proteins involved in signal transduction, via autophosphorylation of KID tyrosine residues (Taylor et al., (1989) *EMBO J.* 8, 2029–2037; Heidaran et al., (1991) *Mol. Cell. Biol.* 11, 134–142; Yu et al., (1991) *Mol. Cell. Biol.* 11, 3780–3785; Kazlauskas et al., (1992) *Mol. Cell. Biol.* 12, 2534–2544; Lev et al., (1992) *Proc. Natl. Acad. Sci. USA* 89, 678–682; Reedjik et al., (1992) *EMBO J.* 11, 1365–1372; Bazenet et al., (1996) *Mol. Cell. Biol.* 16, 6926–6936). Although the signaling pathways and the specific role of the KID are still not fully determined for VEGFRs, the VEGFR-2 KID does contain two tyrosines which are known to be autophosphorylation sites (Dougher-Vermazen et al., (1994) *Biochem. Biophys. Res. Comm.* 205, 728–738).

Since the determination of the first cyclic AMP-dependent protein kinase (cAPK) structure (Knighton et al., (1991) *Science* 253, 407–413) a variety of protein kinase structures have been reported (reviewed in Johnson et al., (1996) *Cell* 85, 149–158). Among the receptor protein tyrosine kinases (RTKs), structures of the kinase domain of the insulin receptor (IRK) (Hubbard, et al., (1994) *Nature* 372, 746–754; Hubbard, (1997) *EMBO J.* 16, 5572–5581) and the fibroblast growth factor receptor-1 (FGFR1) (Mohammadi et al., (1996) *Cell* 86, 577–87; Mohammadi et al., (1997) *Science* 276, 955–960) have been determined.

SUMMARY OF THE INVENTION

The present invention discloses the generation, kinetic characterization, and structure determination of a modified kinase domain of the VEGFR-2 protein, containing 18 residues of the 68 residue KID. This 2.4 Å crystal structure of the phosphorylated VEGFR-2 catalytic domain is the first reported structure of a kinase domain of the PDGFR family. This structure provides insights into the orientation of the KID domain of VEGFR-2 which may be relevant to other PDGFR family members. Furthermore, as inhibition of VEGFR2 kinase has broad clinical applications, this structure provides a three-dimensional description of the target for structure-based design of small molecule VEGFR-2 inhibitors as therapeutic agents.

It is an object of the present invention to disclose an effective method for screening candidate compounds that are specifically agonists or antagonists of various proteins which can be included in the receptor tyrosine kinase family (RTK) by crystallizing RTKs and particularly the VEGFR-2 receptor in order to use molecular modeling of the x-ray crystallography data to model the binding of candidate compounds.

There is disclosed a method for designing and screening potentially therapeutic compounds with activities such as: (1) inhibiting new blood vessel formation that is useful for treating or preventing progression of diabetic retinopathy, cavernous hemangiornas, Kaposi's sarcoma, tumors composed of endothelial-like cells, and growth of cancer cells by preventing their development of a new blood supply: (2)

suppressing development of kidney diseases due to cytokine induced proliferation of mesangial cells and/or glomerular epithelial cells that is useful for treating or preventing progression of diabetic glomerulosclerosis and other glomerulonephritis of various types and etiologies; (3) preventing joint destruction accompanying rheumatoid arthritis due to proliferation of synovial cells; (4) suppressing manifestations of psoriasis due to proliferation of keratinocytes and accumulation of inflammatory cells; (5) suppressing accelerated atherogenesis involved in restenosis of coronary vessels or other arterial vessels following angioplasty; (6) suppressing atherogenesis, coronary artery disease and other vasculopathies due to atherogenesis; and (7) suppressing tumor growth via paracrine or autocrine mediated responses to other cytokines such as PDGF, FGF EGF or VEGF that is useful for treating or preventing progression of tumors such as breast cancer stimulated through overexpression of her-2-neu receptor, wherein the inventive method comprises administering a compound that inhibits signal transduction.

The present invention is useful in developing methods that are used in the iterative drug design process. The process identifies potential agonists and antagonists to VEGFR-2 by de novo design of novel drug candidate molecules which bind to the VEGFR-2 receptor to improve their potency. The x-ray crystallographic coordinates disclosed herein, will allow generation of 3-dimensional models of the catalytic site and drug binding site of the VEGFR-2 protein.

De novo design primarily consists of the generation of molecules via the use of computer programs which build and link fragments or atoms into a site based upon steric and electrostatic complementarity, without reference to substrate analog structures. The drug design process begins after the structure of a target RTK is solved to at least a resolution of 2.8 Å. Refinement of the structure to a resolution of 2.5 Å or better, with "fixed" water molecules in place provides more optimal conditions to undertake drug design.

It is another object of this invention to identify KIDs of proteins in the RTK family and develop deletions in said KIDs such that the proteins will be crystallizable and suitable for measurement by x-ray crystallographic means.

It is a further object of this invention to disclose a process whereby KID regions from a member of the RTK family of genes such as PDGF, EGF, VEGF and others are modified by deletion of amino acids from the KID regions so as to impart favorable physical characteristics of the resulting polypeptide product. Examples of such favorable physical characteristics are increased solubility, greater stability to temperature variations making the polypeptide suitable for analysis by nuclear magnetic resonance, high throughput screening, biochemical characterizations, x-ray crystallography, calorimetry and other diagnostic means.

It is yet another object of this invention to developing screening methods used in the drug design process of potential agonists and antagonists to proteins In the RTK family by de novo design of novel drug candidate molecules with potentially nanomolar potencies. The x-ray crystallographic coordinates disclosed based on the deletion mutated KIDs and various other deletions of said proteins in the RTK family, will allow generation of 3-dimensional models of the active binding site of the proteins in the RTK family.

In the following description, "VEGFR2Δ50" corresponds to SEQ ID NO: 5, and "PDGFRα" refers to SEQ ID No: 6.

BRIEF DESCRIPTION OF THE DRAWINGS

FIG. 1. Secondary structure assignments (as given by Procheck) for the catalytic domain of VEGFR2 and sequence alignment with other representative receptor tyrosine kinases. α helices are designated as αB-αI, β strands are designated as β1–β8. The site of 50 residue deletion in VEGFR2Δ50 is indicated by |. The site of the E990V mutation in VEGFR2Δ50 is denoted by an *. Sequences are from: VEGFR2 (SEQ ID No: 12) (reported here); FGFR1 (SEQ ID No: 7) (Swiss protein database #P11362); IRK (SEQ ID No: 8) (EMBL protein database #A18657; numbering as in Mohammadi et al., 1996); VEGFR1 (SEQ ID No: 9) (Swiss protein database #P17948); PDGFRα (SEQ ID No: 6) (Swiss protein database #P17948).

FIG. 7. Resulting X-ray crystallography coordinates for VEGFR-2 based on the method disclosed in the crystallization and data collection section.

DETAILED DESCRIPTION AND PREFERRED EMBODIMENTS OF THE INVENTION

Cloning of The VEGFR-2 Protein

Figure 2A:
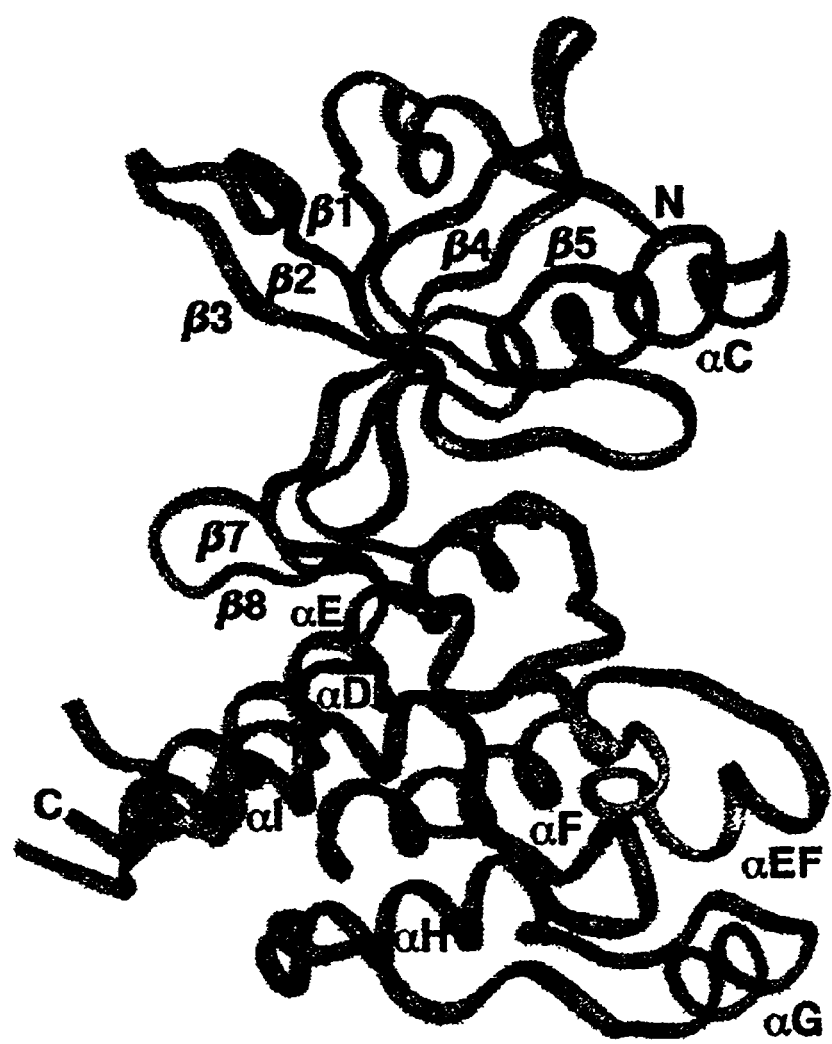
FIG. 2. Overall fold of VEGFR2Δ50P, FGFR1, and IRKP. Backbone representation of structures of the kinase domains of (A) VEGFR2 (VEGFR2Δ50P), (B) FGFR1 (molecule A of PDB entry 1FGK, Mohammadi et al., 1996), and (C) IRKP (PDB entry 1IR3, Hubbard et al., 1997). The views shown in A, B, and C are identical views generated from superpositions of the C-terminal domains. The positions of the termini are denoted by N and C. The nucleotide-binding loop (orange), kinase insert domain (pink), and activation loop (yellow) are highlighted. In (C) the bound AMP-PNP Is shown in green and the peptide substrate is shown in red. Figure prepared with INSIGHT II.

The coding sequence (Terman et al., (1992) *Biochem Biophys. Res. Commun.* 187, 1579–86) for the cytoplasmic domain of the VEGFR-2 was amplified by PCR (Mullis et al., (1992) *Biotechnology* 24, 17–27) from a human aorta cDNA pool (Clontech Palo Alto, Calif.). Two overlapping sequences were amplified independently. Vcyt (residues M806-V1356), which represented the entire cytoplasmic domain, and Vcat (residues C817M-G1191), with boundaries based upon a primary amino acid sequence alignment with the insulin receptor kinase catalytic domain (Wei et al., (1995) *J. Bio. Chem.* 270, 8122–8130).

The PCR oligonucleotide primer sequences for Vcyt were:

```
                                               (Seq ID No. 1)
Vcyt5  5'-CAGCATATGGATCCAGATGAACTCCCATTGG3' and
                                               (Seq ID No. 2)
Vcyt3  5'-GCGGTCGACTTAAACAGGAGGAGAGCTCAGTGTG3'.
```

The PCR oligonucleotide primer sequences for the Vcat were:

```
                                               (Seq ID No. 3)
Vcat5  5'-GCACATATGGAACGACTGCCTTATGATGCCAGG-3' and
                                               (Seq ID No. 4)
Vcat3  5'-CCTGTCGACTTATCCAGAATCCTCTTCCATGCTCAAAG5'.
```

The amplified DNA was digested with the restriction enzymes NdeI and SalI, ligated into the *E coli* plasmid pET24a (Novagen Madison, Wis.) and sequence verified. When compared to the original VEGFR-2 sequence in Genbank, (Accesion number 346345) two nucleotide differences were noted that resulted in codon changes (Glu848-Val and Asn835-Lys) in both Vcyt and Vcat. Our sequence agrees with subsequent VEGFR-2 Genbank submissions (Accession numbers 2655412 and 3132833).

Mutations were introduced by oligonucleotide site directed mutagenesis (Kunkel, 1985) using the Muta-Gene in vitro Mutagenesis Kit from (Bio-Rad Hercules, CA). The Vcat DNA fragment was subcloned from the pET24a vector using an NdeI-XhoI digest into the vector pMGH4 (Schoner et al., 1986, Kan et al., 1992) and this vector was used to generate the ssDNA uracil template (minus strand) in *E. coli* strain CJ236 supplied in the kit. An oligo (SEQ ID No: 10) (5'-CTCAGCAGGATTGATAAGACTACATTGTTC-3') was designed to create a construct (Vcat(ΔG1172-G1191)) which truncated the C-terminus to residue D1171. Another oligo (SEQ ID No: 11) (5'-GAATTTGTCCCCTACAAGG AAGCTCCTGAAGATCTG-3') was designed to delete the central 50 residues (residues T940-E989) of the insert kinase domain, based on a sequence alignment with FGFR1 (Mohammadi et al, 1996). Sequence analysis detected an inadvertent Glu990-Val mutation. All DNA modificaton and restriction enzymes were purchased from New England Biolabs and oligonucleotides were purchased form Genosys Biotechnology.

The VEGFR2Δ50 construct was made in several steps to combine the necessary mutations into the baculovirus expression vector pAcSG2 (Pharmingen San Diego, Calif.). Step 1; the coding region for Vcyt was PCR subcloned from the pET24a vector into the NcoI-KpnI sites of vector pAcSG2. Step2; a 2358bp ScaI-BglII DNA fragment from plasmid pMGH4-Vcat (ΔT940-E989,E990V) was ligated to a 1695bp BglII-ScaI DNA fragment from pMGH4-Vcat (ΔG1172-G1191) creating a pMGH4-Vcat (ΔT940-E989, E990V,ΔG1172-G1191) vector. Step 3; a 913bp BstEII-EagI DNA fragment a pMGH4-Vcat (ΔT940-E989,E990V, ΔG1172-G1191) was ligated to a 3290bp EagI-BstEII DNA fragment from pAcSG2-Vcyt creating pAcSG2-Vcyt (ΔT940-E989,E99V,ΔG1172-G1191), also referred to as VEGFR2Δ50. This final construct was sequenced verified through the entire coding region and confirmed to contain only these known mutations from the wild-type sequence (sequence shown in FIG. 1).

DNA encoding VEGFR2Δ50 was transfected into Sf9 cells with linearized baculovirus DNA according to the protocol of the manufacturer (Pharmingen San Diego, Calif.). Single plaques were isolated from this transfection and high titer stocks generated. All stocks were examined by isolation of baculoviral DNA and PCR amplification of the insert using the polyhedron forward and reverse primers (Invitrogen). Sf21 cells were infected at 1–1.5 million cells/mL at MOI=5 for 72 hours and harvested by centrifugation.

Purification Of VEGFR2Δ50 From Sf21 Cells

Cell pellets were lysed by dounce homogenization and sonication in 20 mM Tris pH 8.0, 20 mM NaCl, 5 mM DTT, and 5% (v/v) glycerol. The lysate was centrifuged for 50 minutes at 35,000 rpm in a Ti45 rotor. The soluble fraction was loaded onto a 40 ml Q-30 anion exchange column (Pharmacia) and eluted with a 20 mM to 600 mM NaCl gradient in 20 mM Tris pH 8.0, 5 mM DTT, and 5% (v/v) glycerol over 20 column volumes. VEGFR2Δ50 protein was pooled by SDS-PAGE gel analysis and by the presence of kinase activity as measured against gastrin substrate peptide substrate (Boehringer Mannheim). Pooled material was loaded onto a 40 mL hydroxyapatite (Bio-Rad) column and washed extensively with 20 mM Tris pH 8.0, 50 mM NaCl, 5 mM DTT, and 5% glycerol. Protein was eluted using a 500 mL linear gradient from 0 to 50 mM potassium phosphate pH 8.0, 50 mM NaCl, 5 mM DTT, and 5% glycerol. VEGFR2Δ50 protein was pooled by SDS-PAGE gel analysis and by the presence of kinase activity as measured against the gastrin peptide. Material from this column was then diluted 1:1 with 20 mM Tris pH 8.0, 20 mM NaCl, 5 mM DTT, and 5% glycerol and loaded onto an 8 mL Q-15 anion exchange column (Pharmacia). Protein was eluted using with a 180 mL linear NaCl gradient (20 mM–175 mM) in 20 mM Tris pH 8.0, 5 mM DTT, and 5% glycerol. VEGFR2Δ50 protein was pooled as described above. 4M $(NH_4)_2SO4$ was added to the pool to final concentration of 0.6 M and the pool loaded onto a 10 mL HP-phenyl sepharose column (Pharmacia). VEGFR2Δ50 protein was eluted using a 200 mL linear reverse gradient from 0.6 M to 0 M $(NH_4)_2SO4$ in 20 mM Tris and 5 mM DTT. Purified VEGFR2Δ50 protein was buffer exchanged into 50 mM Hepes pH 7.5, 10 mM DTT, 10% glycerol, and 25 mM NaCl over a 500 ml G-25 column (Pharmacia) and concentrated to 1 mg protein/mL through a 10 kD cutoff polysulfone membrane (Amicon). Final material was aliquoted and flash frozen in liquid $N_2$ and stored at −70° C.

Kinetic Assays

The coupled spectrophotometric assays were done with purified VEGFR2Δ50 protein that was autophosphorylated under conditions: protein (4 mM), ATP (3 mM), $MgCl_2$ (40 mM), DTT (5 mM), in Hepes (100 mM), 10% glycerol, pH 7.5 at 4° C. for 1 hour.

Coupled Spectrophotometric Assay for the Forward Direction

Tyrosine kinase assays were monitored using a Beckman DU 650 Spectrophotometer. Production of ADP was coupled to oxidation of NADH using phosphoenolpyruvate (PEP)

through the actions of pyruvate kinase (PK) and lactic dehydrogenase (LDH). The oxidaton of NADH was monitored by following the decrease in absorbance at 340 nm ($e_{340}$=6.22 cm$^{-1}$ mM$^{-1}$). Typical reaction solutions contained: 1 mM PEP, 250 mM NADH, 50 units of LDH/mL, 20 units of PK/mL, 5 mM DTT, in 200 mM Hepes, pH 7.5 and varying concentrations of poly($E_4Y_1$) (Sigma), ATP and $MgCl_2$. Assays were initiated with 40 nM of VEGFR2Δ50 protein.

Coupled Spectrophotometric Assay for the Reverse Reaction

ATP generation was coupled to production of NADH via the action of hexokinase (HK) and glucose-6-phosphite dehydrogenase (G6PD). In this assay, HK catalyzes the conversion of ATP to ADP and glucosephosphate. Glucose-6-phosphate is then oxidized to D-6-phosphogluconopyranose-1,5-lactone by G6PD with concomitant reduction of NAD to NADH which can be monitored at 340 nm. Typical assay solution contained: glucose (10 mM), NAD (40 mM), DTT (5 mM), $MgCl_2$ (4 mM), HK (15 unit/mL), G6PD (15 units/mL) and indicated concentrations of ADP and phospho-poly($E_4Y$). The reactions were initiated with addition of VEGFR2Δ50 protein (600–900 nM).

Evaluation of Potential Agonists and Antagonists of the VEGFR2Δ50 Protein

Based on the above spectrophotometric and kinetic assays, one can evaluate potential candidate agonists or antagonists of the VEGFR2Δ50 protein by addition of the candidate compounds to the above assay in a competition. As stated above, the kinetics of the activity of the VEGFR2Δ50 protein were measured against the gastrin peptide. The activity in the presence and absence of a candidate compound is measured and the resulting kinetic data is compared. The affinity of the candidate for the receptor will be reflected in the shift to the right of the kinetic curves indicating a competitive antagonist or with a decrease in the maximum activity, which would indicate a non-competitive antagonism. Conversely, a shift to the left of the kinetic curves would indicate a competitive agonist to the VEGFR2α50 protein. See generally, Bourne, H. R., et al. in, (1987) *Basic & Clinical Pharmacoloy (Katzung, et al., eds) (Ch. 3)* 9–22.

In Vitro Autophosphorylation of VEGFR2Δ50 for Crystallization and Mass Spectrometry.

Aliquots of frozen VEGFR2Δ50 protein were thawed by immersion in cold $H_2O$ and pooled at 4' C. $MgCl_2$ and ATP were added to 26 mM and 4 mM, respectively. VEGFR2Δ50 was incubated at 4' C. for 1 hour. This material (VEGFR2Δ50P) was then buffer exchanged into a solution of 10 mM Hepes 7.5, 10 mM DTT, and 10 mM NaCl and concentrated using a Centriprep-10 (Amicon) to 5 mg protein/mL.

Mass Spectrometry

Trypsin digestion:.

Trypsin digestions of purified VEGFR2Δ50 and VEGFR2Δ50P were conducted at 37° C. suing 0.37 mg/ML protein in 25 mM $NH_4HCO_3$ at pH. 7.7 with a reaction volume of 100 μL for two days.

MALDI/MS.

MALDI-MS analyses were performed in a Voyager-Elite, time-of-flight mass spectrometer with delayed extraction (PerSeptive Biosystems, Inc., Framingham, Mass.). A volume of 1 μL of digested protein sample was mixed with 1 μL of matrix (a-cyano-4-hydroxy-cinnamic acid) in a solution of 50% (v/v) solution of acetonitrile and 0.25% (w/v) trifluoroacetic acid in water. Samples were irradiated with a nitrogen laser operated at 337 nm.

NanoESI-MS.

NanoESI-MS analyses were performed on a triple quadrapole mass spectrometer (PE Sciex API III, Alberta, Canada) modified with a NanoESI source from Protana A/S, (Denmark). The ESI voltage was set at 700 V and the orifice settings were maintained at 100 V. 3 μL of digested protein was mixed with 7 μL of methanol and 0.5 μL formic acid and then 4 μL of this sample was injected into the mass spectrometer. Ion scans were used to obtain the sequence of phospho-peptides.

Crystallization and Data Collection

Purified phosphorylated VEGFR2Δ50 was concentrated on average to 5 mg protein/mL using a Centricon-10 centrifugal concentrator. Crystals were grown by the hanging drop vapor diffusion method at 4° C. Drops containing 2 μL of protein solution and 2 μL of a mother liquor solution (100 mM Hepes at pH 7.2. 2 M $(NH_4)_2SO_4$, and 2% (v/v) monomethylether polyethylene glycol mW=550) were equilibrated above a 1 mL reservoir of the mother liquor solution to which 50 mM β-mercaptoethanol had been added. Crystals appeared after 3–4 days and grew to as large as 0.3×0.2×0.5 mm over 21 days.

X-ray diffraction data sets were collected using a Rigaku RU-200 rotating anode X-ray generator (CuKα) operated at 50 kV and 100 mA and equipped with Supper focusing mirrors and a MAR345 MAR Research image plate detector. Data collection on frozen crystals was done by transferring a crystal into a cryoprotectant solution (100 mM Hepes at pH 7.2, 2.2 M $(NH_4)_2SO_4$, 0.6 M sucrose, 0.55 M glucose, and 2% (v/v) monomethylether polyethylene glycol MW=550), flash freezing the crystal in liquid nitrogen, and then transferring the frozen crystal into a stream of nitrogen at −186° C. Data was integrated and scaled using DENZO and SCALEPACK (Otwinowski, 1993) Data collection statistics are given in Table 2.

Initial protein phases were obtained using the AMoRe molecular replacement program (Navaza, 1994), molecule 1 of the FGFR1 structure (Mohammadi et al., 1996; PDB entry 1FGK) as a search probe, and the native1 data set. The correct solution was achieved by including the FGFR1 sidechains and removing from mobile residues of the activation loop (640–660), the N-terminus (464–467), a short loop (517–520), and the C-terminus (760–762) from the search model. The correct solution was the top peak in the rotation and translation functions with a correlation coefficient of 0.31. Rigid body refinement in AMoRe improved the solution to a correlation coefficient of 0.49 and an R-factor of 46.3% in the 12.0–4.0 Å resolution range. The correctness of this solution was cross-checked by calculation of a difference Fourier with a $KAu(CN)_2$ derivative. This derivative was generated by soaking a crystal for 3 days in reservoir solution containing 0.5 mM $KAu(CN)_2$ and then increasing the heavy atom concentration to 5 mM and soaking for an additional 64 hours. Scaling of data sets, Patterson calculations, Fourier calculations, and the generation of phases were done using Xtalview (McRee et al., 1992)

Refinement of the model was done using Xplor version 3.1 (Brünger, 1992). Calculation of electron density maps and model fitting was done using XtalView (McRee et al., 1992) Refinement was begun using a data set collected at 4° C. (native2) and was completed using a data set (native3) collected at −186° C. The final R-factor is 20.2% for data in the range 8–2.4 Å (Fo>2δ). The average B value for all atoms is 31.8 Å$^2$ for protein atoms and 42.8 Å$^2$ for water molecules. The final model includes residues 820–939, 998–1047, and 1064–1168; of these residues the sidechains of K838, R842, F845, K939, D998, K1023, R1027, Y1038, K1039, K1110, and E1113 could not be modeled beyond Cα due to a lack of interpretable density. Analysis of main-chain torsion angles as done using PROCHECK (Laskowski et al., 1993) shows of the 275 residues in the model none occur in the disallowed region and only 4 occur in the generously allowed region of a Ramachandran plot. 182 water molecules were fit to electron density peaks which were greater than 3δ and were located in positions to make reasonable hydrogen bonds to the protein or other water molecules.

Superpositions of various kinase structures was done using the graphics program Insight II (Molecular Simulations Inc, San Diego, Calif.).

EXAMPLE 1

Structure Determinations

The tyrosine kinase domain of human VEGFR-2 lacking the 50 central residues of the 68 residues of the KID was expressed in a baculovirus/insect cell system. Of the 1356 residues of full-length VEGFR-2 this construct (VEGFR2Δ50) contains residues 806–939 and 990–1171 of the cytosolic domain (FIG. 1). VEGFR2Δ50 also contains one point mutation (E990V) within the KID relative to wild-type VEGFR-2.

In addition to catalyzing its autophosphorylation, VEGFR2Δ50 is also capable of catalyzing phosphorylation of a poly($E_4Y$) exogenous substrate. Detailed kinetic analysis (Table 1) revealed that its kinetic parameters were nearly identical to that of a comparable VEGFR-2 protein construct containing the entire KID (Parast et al., in press). These results taken together indicate that VEGFR2Δ50 is a fully active functional enzyme. Therefore, deletion of 50 central residues of the KID has no observed effect on the catalytic steps of the phosphotransfer reaction. It was also determined that deletion of more than 60 amino acids from the KID region did cause a diminishment in the activity of the enzyme.

TABLE 1

Kinetic constants of VEGFR2Δ50

| Substrate | $K_M$ (mM) | $k_{cat}$ (s$^{-1}$) | $k_{cat}/K_M$ (s$^{-1}$M$^{-1}$) |
|---|---|---|---|
| Forward Reaction | | | |
| MgATP | 0.153 | 13.3 | 87 × 10³ |
| poly($E_4Y$) | 2.1 | | 63 × 10² |
| Mg$^{2+}$ | 6.8 | | 20 × 10² |
| Reverse Reaction | | | |
| MgADP | 0.056 | 0.13 | 23 × 10² |
| P-poly($E_4Y$) | 1.0 | | 13 × 10¹ |

The VEGFR-2 KID sequence is hydrophilic and highly charged, containing 6 lysine, 5 arginine, 8 glutamic acid, and 5 aspartic acid residues (FIG. 1). Initially several protein constructs containing the VEGFR-2 catalytic domain with the entire KID were generated. After exhaustive attempts to crystallize these protein constructs failed to yield even marginal crystals, the VEGFR2Δ50 construct was created to test the idea that the highly charged KID was interfering with crystallization. As determined by dynamic light scattering this VEGFR2Δ50 construct, which eliminated 14 charged residues, exhibited markedly better stability to temperature and protein concentration than protein constructs containing the entire KID.

For crystallization, purified VEGFR2Δ50 was autophosphorylated in vitro by incubation with MgATP. Matrix-assisted laser desorption ionization (MALDI) and nanoelectrospray ionization (NanoESI) mass spectrometry analysis of full-length phosphorylated VEGFR2Δ50 (VEGFR2Δ50P) protein and tryptically digested peptides indicates phosphorylation of Y1059 using the autophosphorylation conditions described here. Crystals diffracting to 2.2 Å were obtained of VEGFR2Δ50P in an unligated state. The crystals belong to the orthorhombic space group P2$_1$2$_1$2$_1$ with one VEGFR2Δ50P molecule in the asymmetric unit. Initial crystallographic phases were determined by molecular replacement using the structure of the unphosphorylated kinase domain of FGFR1 (Mohammadi et al., 1996) as a search model. The correctness of the molecular replacement solution was cross-checked using a gold cyanide derivative. The derivative data, however, was not used for phase calculations of electron density maps used to build the model. The structure has been refined to an R-factor of 20.2% for 8–2.4 Å data (Fo>28). VEGFR2Δ50P residues for which backbone atoms were not modeled due to disorder include the N-terminal residues 806–819, residues 990–997 of the KID, residues 1048–1063 of the activation loop, and residues 1169–1171 of the C-terminus. Structure determination statistics are included in Table 2.

TABLE 2

VEGFRΔ50P structure determination statistics

| Data Set | Native (3) | Native (1) | Native (2) | KAu(CN)$_2$ |
|---|---|---|---|---|
| Data resolution (Å) | 15-2.2 | 20-3.0 | 15-2.4 | 15.3.1 |
| R$_{sym}$ (%) | 5.2$^a$ | 8.4 | 7.0 | 7.1 |
|  | (19.6)$^b$ | (19.2) | (21.9) | (19.5) |
| Completeness (%) | 93.0 | 97.5 | 98.8 | 96.5 |
|  | (81.0) | (98.4) | (98.8) | (95.0) |
| Temperature (° C.) | −186 | room (~21) | 4 | 4 |
| Unit cell a (A) | 95.41 | 97.10 | 98.52 | 97.71 |
| Unit cell b (A) | 96.04 | 96.94 | 96.50 | 96.97 |
| Unit cell c (A) | 38.22 | 38.63 | 38.56 | 38.52 |
| Refinement resolution (Å) | 8-2.4 | — | — | — |
| Refined R (%) | 20.2$^{c,d}$ | — | — | — |

$^a$R$_{sym}$ = ΣhklΣi|/i (hkl) − </(hkl)>|/ΣhklΣi/i (hkl)
$^b$Value in parenthesis is for highest (resolution shell)
$^c$R = Σhkl| |F$_o$(hkl)| − |F$_c$(hkl)| |/Σhkl|F$_o$(hkl)| where F$_o$ and F$_c$ are the observed and calculated structure factors, respectively (F$_o$ > 2δ)
$^d$Model includes 275 protein residues and 182 water molecules Overall Kinas Fold Analogous to previously reported structures of both serine/threonine and tyrosine protein kinases, VEGFR2Δ50P is folded into two lobes with catalysis of phosphotransfer taking place in a cleft between the two lobes (reviewed in Cox et al., 1994; Johnson et al., 1996) A C α trace of the VEGFR2Δ50P structure is shown in FIG. 2a. Kinase secondary structural elements are designated (FIG. 1) according to the convention originally given for cAPK (Knighton et al., 1991). The N-terminal lobe (approximately residues 820–920) folds into a twisted β sheet with one α helix (αC). The β structure comprises five antiparallel strands (β1–β5), three of which (β1–β3) are highly curved and curl over the other two strands (β4–β5). The larger C-terminal domain (approximately residues 921–313) contains two antiparallel β strands (β7–β8), which lie at the top of the C-terminal domain adjacent to the N-terminal β-sheet. Seven α-helices (αD, αE, αE-F, αG, αH, αI) form the remaining core of the C-terminal domain. Like other kinases, VEGFR2Δ50P contains two functionally important loop regions: the glycine-rich nucleotide binding loop (residues 841–846), the catalytic loop (residues 1026–1033) and the activation loop (residues 1046–1075) (FIGS. 1 and 2a).

Of the reported kinase structures, the VEGFR2Δ50P structure resembles most closely that of the catalytic domain of FGFR1 (Mohammadi et al., 1996; PDB entry 1FGK) with which it shares approximately 55% sequence identity (FIG. 1). Since the two molecules in the crystallographic asymmetric unit of the FGFR1 structure solution are very similar, comparisons to VEGFR2Δ50P will primarily be described only for FGFR1 molecule A. Least squares superposition of 82 Cα positions of (β1–β5) of the N-terminal lobe or 152 Cα positions residues (αD, αE, αF, αG, αH, αI) of the C-terminal lobe between FGFR1 and VEGFR2Δ50P result in respective rms deviations of 0.40 Å and 0.52 Å. A relative rotation of approximately 5° between the two lobes results in the interlobe cleft of VEGFR2Δ50P being slightly larger and more open. Measurement of distances between equivalent Cα's (K523 and R675 of FGFR1, S877 and R1080 of VEGFR2Δ50P) at the ends of the cleft reveal that this distance is 25.3 Å in VEGFR2Δ50P as compared to 23.2 Å in FGFR1. This is however a minor difference, as compared to much larger relative lobe rotations observed among kinase structures in various ligation and phosphorylation states (Johnson et al., (1996) *Cell* 85, 149–158). For example, the inter-lobe orientation seen here for VEGFR2Δ50P is in an approximately 20° more open conformation than that seen in the ternary complex structure of the phosphorylated kinase domain of IRK bound to the ATP analog AMP-PNP and a peptide substrate (Hubbard, (1997) *EMBO J.* 16, 5572–5581; PDB entry 1IR3) (FIG. 2c).

Figure 2B:
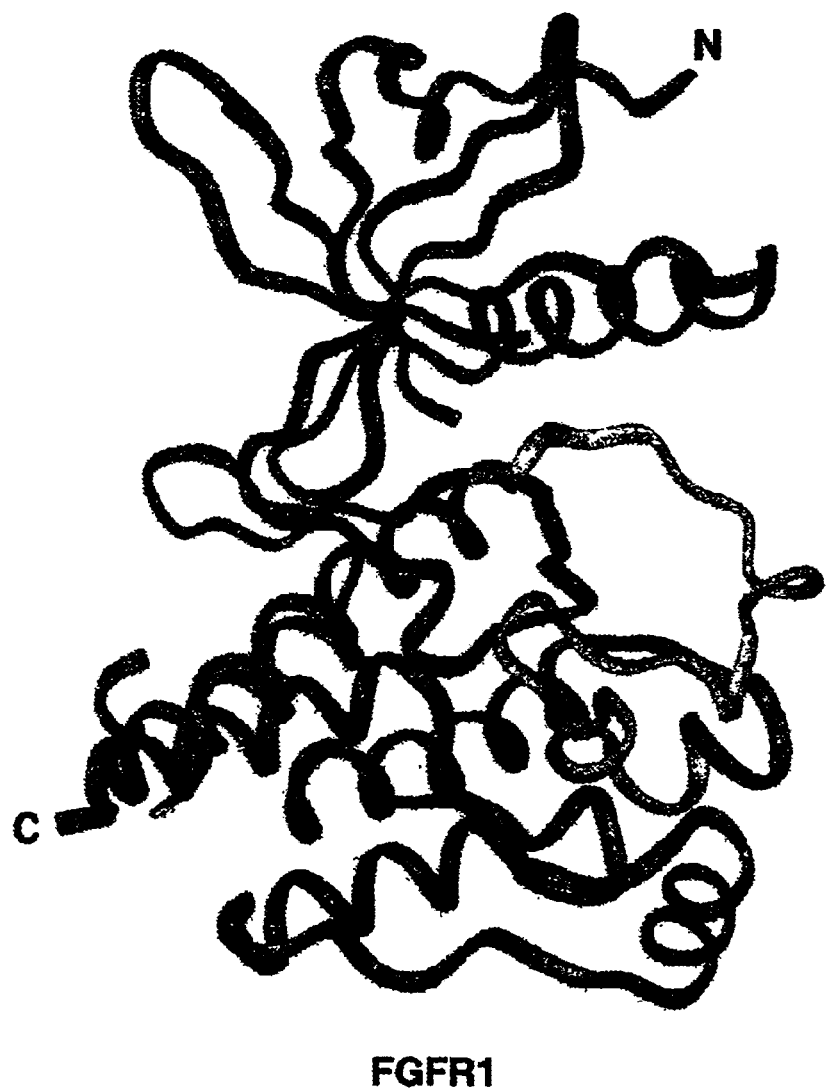
Figure 2C:

While the β-strand positions of the N-terminal lobe agree well between VEGFR2Δ50P and FGFR1, the structures do diverge significantly at the N-terminal residues preceding the first conserved region starting at residue W827 (FIG. 2a and 2b). The first 14 residues (M806–E819) of VEGFR2Δ50P are completely disordered and the next seven residues (L820–R826) form an extended loop structure. It is likely that residues 806–819 do not form part of the active kinase region but are instead part of, or are adjacent to, the juxtamembrane region of VEGFR-2. Residues 820–826 do seem to be part of the kinase domain, although a flexible one, as analogous residues are also ordered in the structures of FGFR1, IRK, and the non-receptor tyrosine kinase Lck (Yamaguchi and Hendrickson, (1996) *Nature* 384, 484–489). Other differences between the VEGFR2Δ50P structure and other kinase structures occur at the kinase insert domain and the activation loop (discussed below).

Catalytic Loop and ATP Binding Site

Figure 3A:
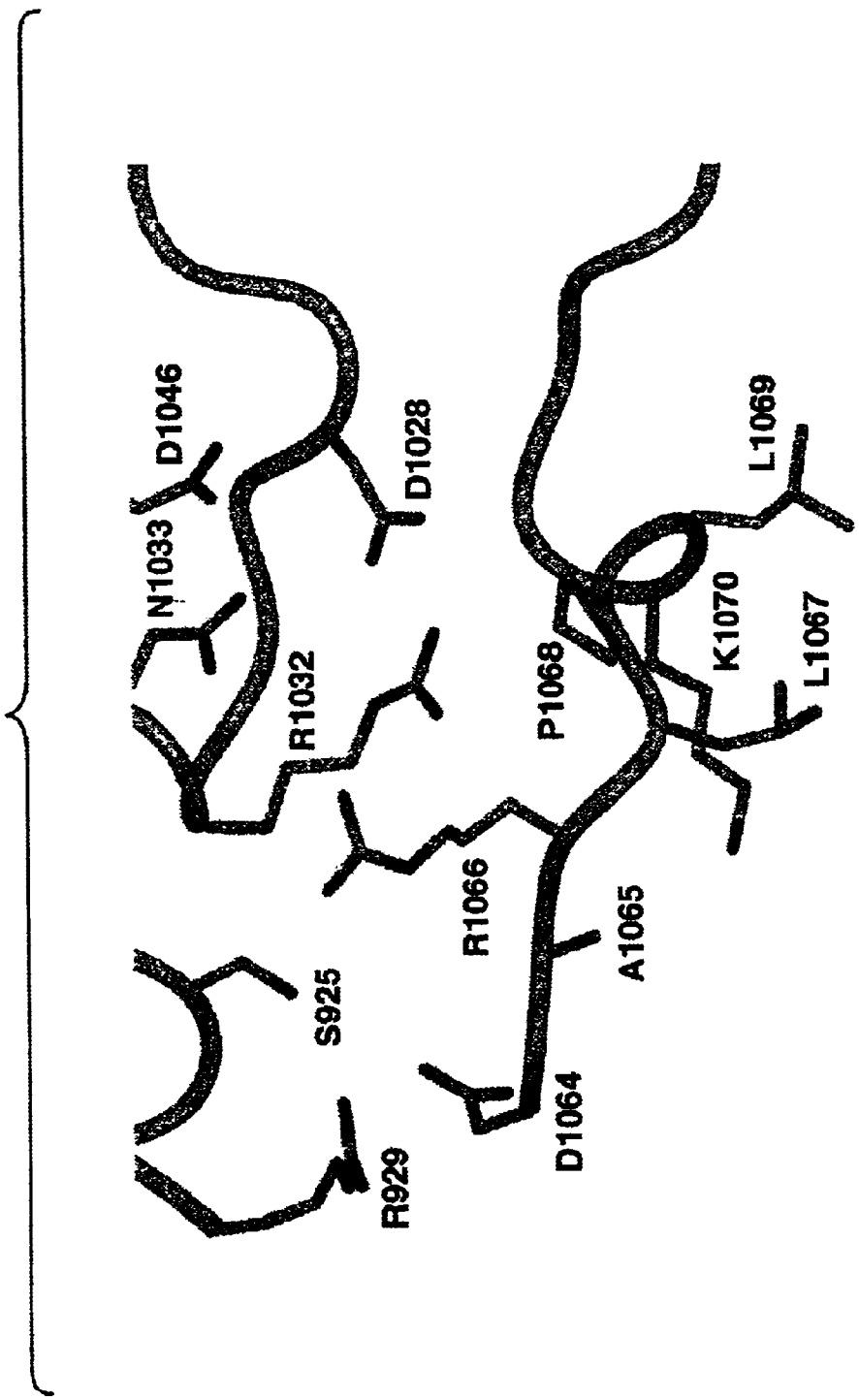
FIG. 3. Catalytic site of VEGFR2Δ50P and IRKP. Cross section of the catalytic site of (A) VEGFR2Δ50P and (B) IRKP (PDB entry 1IR3; Hubbard et al., 1997) structures. Atoms are colored by element type: carbon (green), oxygen (red), nitrogen (blue), sulfur (yellow), phosphorous (pink), and magnesium ion (orange). (A) includes only protein atoms. (B) includes protein atoms, AMP-PNP atoms, and $Mg^{2+}$ ions. Figure generated using INSIGHT II.
Figure 3B:
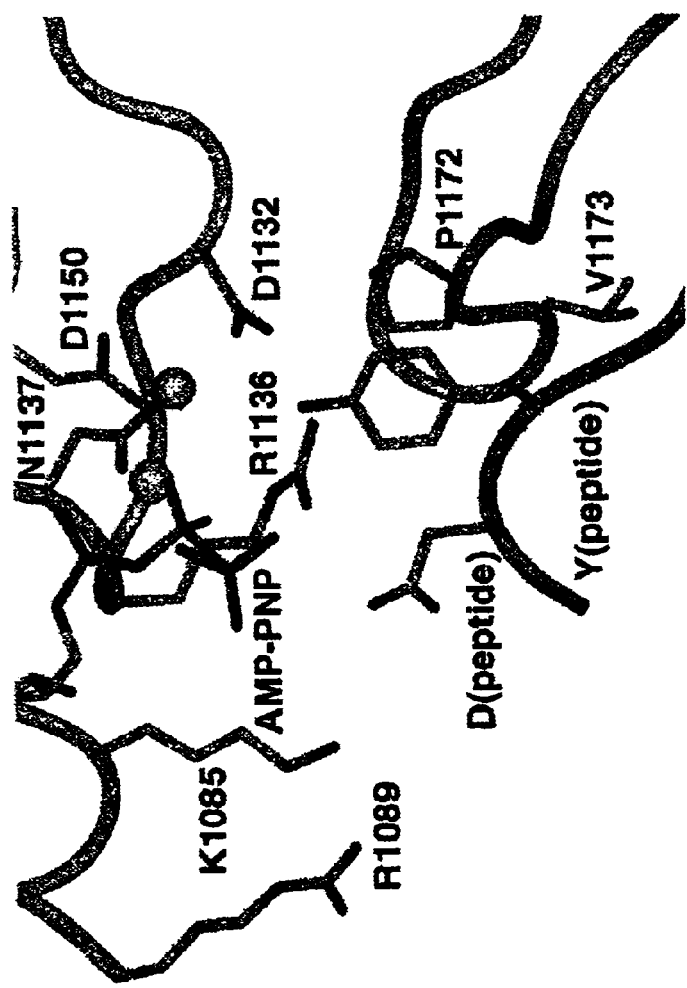

In protein kinases, the loop between αE and β7 has been termed the catalytic loop as it contains an invariant aspartic acid (D1028) that is believed to function as a catalytic base in the phosphotransfer reaction (Johnson et al., 1996). This aspartic acid is part of a stretch of residues (H1026–N1033) whose sequence HRDLAARN is highly conserved among protein tyrosine kinases. In VEGFR2Δ50P the backbone position and most sidechain positions of this loop are similar to those in the unliganded FGFR1 and ternary phosphorylated IRK (IRKP) complex structures. As seen in these previous structures the sidechain carboxylate of the catalytic loop aspartic acid (D1028) is hydrogen bonded to the sidechains of the conserved arginine (R1032) and asparagine (N1033) (FIG. 3).

The ATP binding site of protein kinases lies at the cleft between the N and C-terminal lobes (FIG. 2c). For VEGFR2Δ50P, the residues forming this site consist primarily of residues E917–N923, joining the two lobes, and residues L840–I849 which include parts of β1, β2, and the glycine-rich loop of G841–G846. The glycine-rich loop, also referred to as the nucleotide binding loop, is a flexible segment whose position differs among kinase structures in various activated and liganded states. In VEGFR2Δ50P this loop is fairly well ordered and all atoms could be modeled with the exception of the sidechains of R842 and F845. The relative position and conformation of this loop is similar to that observed in the unligated FGFR1 structure. However, this position is markedly different from that in the IRKP ternary complex structure in which the approximately 20° relative rotation of the N and C-terminal lobes results in the glycine-rich loop being 5 Å closer to the C-terminal lobe than in VEGFR2Δ50P structure.

Figure 4:
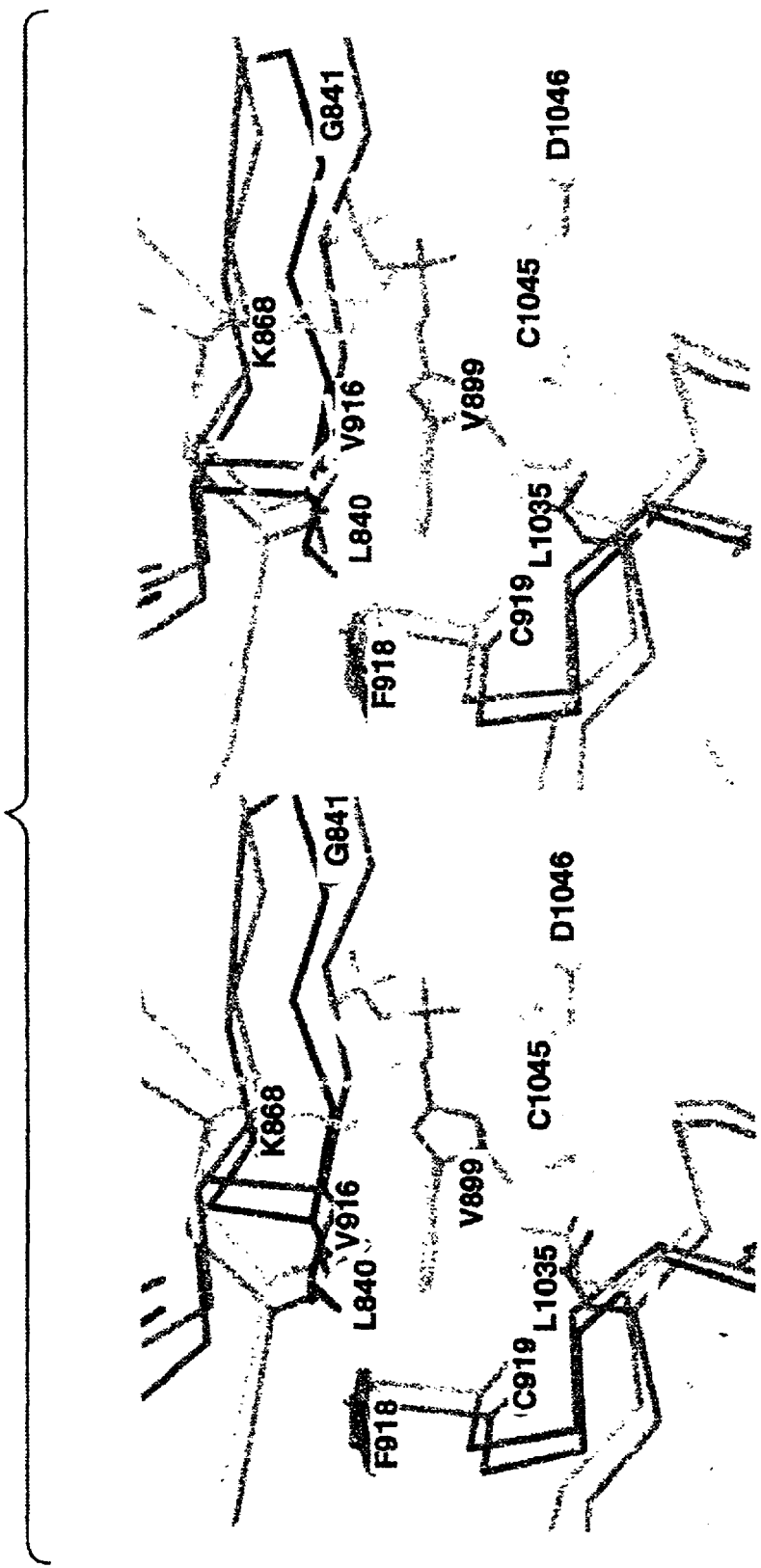
FIG. 4. Nucleotide binding site of VEGFR2Δ50P and FGFR1. Stereo view showing Cα trace and some sidechains of a superposition of the nucleotide binding sites of the VEGFR2Δ50P and the FGFR1-(AMP-PCP) complex (molecule B, Mohammadi et al., 1996) structures. The superposition was done using Cα positions of helices (D,E, F,G,H, and I) of the C-terminal lobes. Carbon atoms of VEGFR2Δ50P are shown in yellow and carbon atoms of FGFR1 are shown in purple. The coloring for other protein atoms is: oxygen (red), nitrogen (blue), and sulfur (green). The AMP-PCP in the FGFR1 structure is depicted in orange. Labels correspond to VEGFR2Δ50P residues. Figure created with Xfit (McRee et al., (1992) *J. Mol. Graph.* 10, 44–46.).

In reported kinase structures with bound ATP or an ATP analog, the adenine ring makes two conserved hydrogen bonds with the protein backbone. In the structure of FGFR1 with AMP-PCP bound (Mohammadi et al., 1996) these hydrogen bonds are between the adenine $NH_2$ and the backbone C=0 of E562 (E917 VEGFR2Δ50P) and between the adenine N1 and the backbone NH of A546 (C919 VEGFR2Δ50P). Although the structure presented here does not contain a bound nucleotide, the similarities in the positions of these backbone atoms to those in FGFR1 indicate that these hydrogen bonds would be formed in a VEGFR2Δ50P-ATP complex and therefore the adenine is expected to bind in a similar position (FIG. 4).

Variation in the ATP-binding sites of kinases involved in disease is of considerable importance in the design of selective ATP-competitive inhibitors as therapeutics. A comparison of the ATP binding sites of FGFR1 and VEGFR2Δ50P reveals that while the overall architecture of the site is conserved, several sequence differences result in differences in the shape of the accessible area for ligand binding. Specific sequence differences between FGFR1 and VEGFR-2 in this site include: V899 (I545 FGFR1), F918 (Y563 FGFR1), C919 (A564 FGFR1), and C1045 (A640 FGFR1) (FIG. 4). Similarly, comparison to the ternary IRKP complex structure reveals variation in the adenine site at V916 (M1076 IRK), F918(L1078), C919 (M1079 IRK), L1035 (M1139 IRK), and C1045 (G1149 IRK). Even greater sequence and structural variation in the adenine site is seen when the VEGFR2Δ50P structure is compared to serine/threonine kinase structures, suggesting that these differences are useful in the design of selective ATP-competitive inhibitors.

Activation Loop

Protein kinases contain a large flexible loop, referred to as the activation loop (A-loop) whose conformation is postulated to regulate kinase activity (FIG. 2). In many kinases the conformation of the AL is controlled by the phosphorylation of specific A-loop residues (Johnson et al., 1996). The loop can be generally defined as beginning with the conserved residues DFG and ending at the conserved APE sequence (Johnson et al., 1996). In VEGFR-2 this segment corresponds to D1046–E1075 and contains two tyrosines (Y1054 and Y1059). Both Y1054 and Y1059 were found to be autophosphorylation sites when the cytosolic domain of VEGFR-2 was expressed in *E. coli* (Dougher-Vermazen et al., 1994). Using the in vitro autophosphorylation protocol described here for VEGFR2Δ50, a stable phosphorylation site is indicated at Y1059, however no evidence of phosphorylation of Y1054 was detected.

In this unliganded VEGFR2Δ50P structure presented here, the A-loop appears quite mobile and interpretable electron density was not present for most of the central portion of the loop (G1048–G1063). This disorder is consistent with mobility of the A-loop deduced from other kinase structures. For example, of the two molecules in the asymmetric unit of the unphosphorylated FGFR1 kinase structure the center of the A-loop has relatively high temperature factors in molecule A and is completely disordered in molecule B. Although residues 1048–1063 could not be modeled in VEGFR2Δ50P, unambiguous electron density was present for residues D1064–E1075, clearly indicating that these residues adopt a conformation similar to that observed in the unphosphorylated FGFR1 structure. The segment of D1064–P1068 has an extended structure that lies adjacent to the catalytic residues D1028 and R1032 (FIG. 3a). Comparison to the structure of the (MgAMP-PNP)-peptide-IRKP complex structure indicates that the position of R1066–P1068 in this VEGFR2Δ50P structure is inhibitory to substrate binding. P1066 occupies equivalent space allocated to the tyrosine sidechain of the peptide substrate in the ternary IRK3P complex structure. The conformation of residues L1069–E1075 is similar to that in the ternary IRKP complex structure, however there is a complete directional change at P1068 (P1172 IRK) between the two structures. In the IRK structure residues N-terminal to this proline are directed toward αEF while in VEGFR2Δ50P they are directed toward αD on the opposite side of the protein (FIGS. 2 and 3).

Despite the phosphorylation of Y1059 prior to crystallization, the conformation seen here for residues D1064–P1068 is similar to the inhibitory conformation observed for analogous residues in the unphosphorylated FGFR1 structure. Y1059 in VEGFR2Δ50 corresponds to a relatively conserved phosphorylation site among protein tyrosine kinases. In the ternary IRKP complex structure and the phosphorylated lymphocyte kinase (Lck) structure (Yamaguchi and Hendrickson, 1996) the tyrosine at this position (Y1163 IRK, Y394 Lck) is phosphorylated and the A-loop has a non-inhibitory conformation similar to that observed in a phosphorylated cAPK ternary complex structure (Zheng et al., 1993). The interactions the phosphate group at this position makes with other protein residues are believed to help stabilize an A-loop conformation that allows substrate and ATP binding (Johnson et al., 1996; Hubbard, 1997). However, since this VEGFR2Δ50P structure described here does not exhibit a similar open A-loop conformation but rather has an inhibitory conformation with much of the loop disordered it is possible that the monophosphorylated A-loop of VEGFR2Δ50P exists in a dynamic equilibrium involving several conformations and that the conformation observed here is the one most favored in this crystal environment.

Kinase Insert Domain

The kinase insert domain occurs in the kinase C-terminal lobe and connects helices αD and αE. In VEGFR-2 this region corresponds to a 68 residue stretch from N933 to L1000 (FIG. 1). The lack of effect on intrinsic kinase activity (noted above) of deletion of residues T940–E989 is perhaps not surprising as the ends of the KID domain occur relatively far away (approximately 35–40 Å) from the catalytic site and on the opposite side of the protein from the position of the activation loop (FIG. 2). These results are consistent with those for the CSF-1 receptor kinase in which deletion of 58 of the 64 residues of the CSF-1 KID only decreased it's ability to phosphorylate a peptide substrate by 10% (Taylor et al., 1989). Deletion of the entire 98 residues of βPDGFR, however, resulted in an 80% decrease in kinase activity towards a peptide substrate (Severinsson et al., (1990) Mol. Cell. Biol. 10, 801–809). Thus, the present invention allows for the production of a synthetic catalytic linker which recognizes that the majority of KID is not required for catalysis but rather only a small number of residues must be present to form a linker between αD and αE so as to maintain a competent kinase structure.

Figure 5:
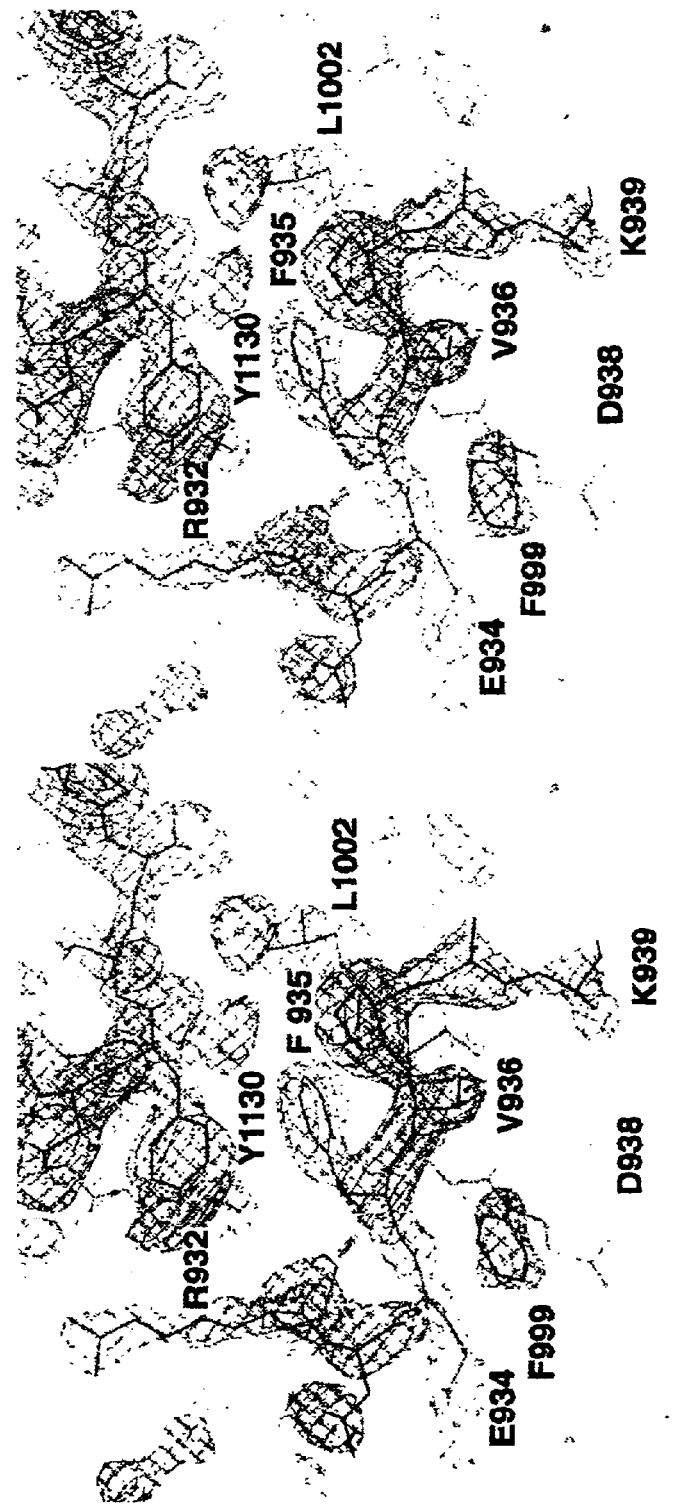
FIG. 5. Electron density map of the kinase insert domain area of VEGFR2Δ50P. Stereo view of a $2F_o$-$F_c$ map computed at 2.4 Å and contoured at 1.2δ and superimposed with the refined model. Carbon atoms are yellow, oxygen atoms red, and nitrogen atoms are blue. Water molecules are depicted as red crosses. Figure created with Xfit (McRee et al., 1992).
Figure 6:
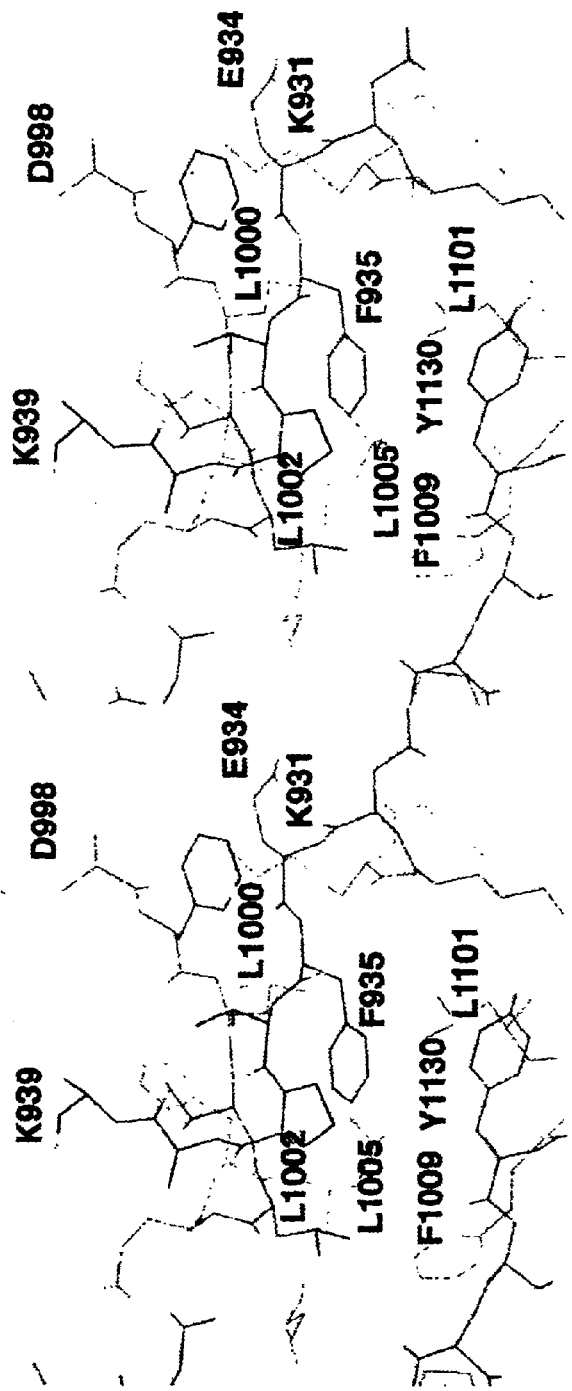
FIG. 6. Kinase insert domain of VEGFR2Δ50P. Stereo cross section showing the ordered residues of the kinase insert domain of VEGFR2Δ50P. Carbon atoms are yellow, oxygen atoms are red, nitrogen atoms are blue, and sulfur atoms are green. View is rotated roughly 180° from FIG. 5. Figure created with Xfit (McRee et al., 1992).

In the VEGFR2Δ50P structure following αD, residues N933–P937 form a loose turn and an extended strand whose ends are roughly perpendicular to the axes of αD and αI at the C-terminus. In different Fourier maps, the electron density is strong and clear for residues N933–P937 and becomes weak for Y938 and K939 (sidechains of Y938 and K939 are not modeled) (FIG. 5). The 50 residue deletion in VEGFR2Δ50 directly follows K939 so that the residue immediately C-terminal to K939 is V990, maintaining the residue numbering in full-length VEGFR-2. Residues V990–K997 are disordered and interpretable electron density begins again at D998. Residues D998–T1001 then form a short strand that joins αE at residue L1002 (FIGS. 5 and 6).

The two strands at the N-terminal and C-terminal ends of the KID form a pseudo two-stranded parallel β-sheet structure that is different from the conformations seen in this region of other kinase structures. The two ends of the KID thus make a variety of interactions which may help to stabilize the overall conformation and position of this domain in VEGFP-2. The sidechain of K931 makes an ionic interaction with the sidechain of E934 and also makes a hydrogen bond to the backbone carbonyl of D998 (FIG. 6). Hydrogen bonding interactions between the strands include: E934 backbone C=O to L1000 NH, V936 NH to L1000 C=O, and P937 C=O to L1002 NH. In addition to these polar interactions, the sidechains of F935, P937, and L1000 are involved in extensive hydrophobic contacts. The sidechain of F935 is nestled in a hydrophobic pocket formed by the sidechains of L928, P937, L1000, L1002, L1005, L1101, and Y1130 (FIGS. 5 and 6). The L1000 sidechain also packs against the sidechains of Y927, K931, H1004, and Y1008.

It has been found by the applicants that deletion of portions of the KID also impart other useful and desirable characteristics to the modified VEGFR-2 polyprotein. The modified polypeptide has exhibited greater stability when exposed to higher temperatures in solution than the wild-type protein. Additionally, the modified polypeptide has also exhibited improved solubility than the wild-type protein. It is apparent to those skilled in the art that these properties allow improvements in various commercial aspects of the present invention. Examples of potential uses for the modified proteins include high-throughput screening of potential ligands for the receptor by various methods including those based on gene-chip technology (Affymax, Inc,) phage-display peptide libraries (The Ph.D. Kit® by New England BioLabs, Inc.) as well as in depth analysis via FT-NMR.

It is therefore contemplated that the entire KID can be deleted and retain some catalytic activity in other related RTKs such as but not limited to PDGFα and β and other previously mentioned proteins. Furthermore, in one embodiment of the invention the entire KID is deleted and replaced with a synthetic catalytic linker of at least one amino acids such that both the catalytic activity and the crystallizability of the protein is retained.

Cloning of the PDGFRα Protein

In this example, the PDGFRα polyprotein is cloned using the methods outlined for VEGFR-2 above. The coding sequence for PDGFRα is derived from the sequence disclosed by Matsui, T., et al., (1989) *Science* 243: 800–804 (Accession No. 66814). PCR oligonucleotide primers are then made which code for residues located in the cytoplasmic domain and the catalytic domain of the protein. The catalytic domain of PDGFRα is shown starting at residue 689 (N) and ending at residue 791 (T) in FIG. 1.

The remainder of the cloning and purification steps would be similar to those disclosed for the VEGFR2Δ50 protein and use technology well known to those skilled in the art.

It is contemplated that other members of the RTK family and other uses for the data disclosed herein and are not limited by the examples shown.

What is claimed is:

1. A method for identifying compounds which interact with the kinase domain of a modified receptor tyrosine kinase (RTK) polypeptide, comprising the steps of:
   (a) expressing in a host cell an isolated DNA sequence or variant thereof which encodes a modified RTK gene construct, wherein said RTK gene construct contains an RTK kinase domain α helix D linked to RTK kinase domain α helix E by a truncated RTK kinase insert domain (KID), said host cell capable of producing a modified RTK polypeptide that retains kinase activity and which forms crystals suitable for x-ray crystallography, wherein the modified RTK polypeptide is vascular endothelial growth factor receptor-2 (VEGFR-2);
   (b) exposing said modified RTK polypeptide to said compound; and
   (c) evaluating the interaction between the modified RTK polypeptide and said compound.

2. A method for identifying compounds which interact with the kinase domain of a modified receptor tyrosine kinase (RTK) polypeptide, comprising the steps of:
   (a) expressing in a host cell an isolated DNA sequence or variant thereof which encodes a modified RTK gene construct wherein said RTK gene construct contains an RTK kinase domain α helix D linked to RTK kinase domain α helix E by a truncated RTK kinase Insert domain (KID), said host cell capable of producing a modified RTK polypeptide that retains kinase activity and which forms crystals suitable for x-ray crystallography, wherein the modified RTK polypeptide comprises the VEGFR2Δ50 polypeptide of SEQ ID NO: 5;
   (b) exposing said modified RTK polypeptide to said compound; and
   (c) evaluating the interaction between the modified RTK polypeptide and said compound.

* * * * *